United States Patent
Jooss et al.

(10) Patent No.: US 9,669,081 B2
(45) Date of Patent: Jun. 6, 2017

(54) METHODS AND COMPOSITIONS FOR TREATING PROSTATE CANCER OR INDUCING A HUMORAL IMMUNE RESPONSE AGAINST PROSTATE CANCER

(71) Applicant: ADURO GVAX INC., Berkeley, CA (US)

(72) Inventors: Karin Jooss, Bellevue, WA (US); Thomas Harding, San Francisco, CA (US); Minh Nguyen, San Francisco, CA (US); Kathryn E. Koprivnikar, Cupertino, CA (US)

(73) Assignee: ADURO GVAX, INC., Berkeley, CA (US)

(*) Notice: Subject to any disclaimer, the term of this patent is extended or adjusted under 35 U.S.C. 154(b) by 0 days.

(21) Appl. No.: 14/491,949

(22) Filed: Sep. 19, 2014

(65) Prior Publication Data
US 2016/0151472 A1    Jun. 2, 2016

Related U.S. Application Data

(62) Division of application No. 12/546,399, filed on Aug. 24, 2009, now Pat. No. 8,840,881.

(60) Provisional application No. 61/092,676, filed on Aug. 28, 2008.

(51) Int. Cl.
| | | |
|---|---|---|
| A01N 63/00 | (2006.01) | |
| A61K 39/00 | (2006.01) | |
| A61K 48/00 | (2006.01) | |
| A61K 35/13 | (2015.01) | |
| A61K 38/19 | (2006.01) | |
| A61K 35/12 | (2015.01) | |

(52) U.S. Cl.
CPC .......... *A61K 39/0011* (2013.01); *A61K 35/13* (2013.01); *A61K 38/193* (2013.01); *A61K 48/00* (2013.01); *A61K 2035/122* (2013.01); *A61K 2039/5152* (2013.01); *A61K 2039/5156* (2013.01); *A61K 2039/55522* (2013.01); *A61K 2039/575* (2013.01)

(58) Field of Classification Search
None
See application file for complete search history.

(56) References Cited

U.S. PATENT DOCUMENTS

| | | |
|---|---|---|
| 5,637,483 A | 6/1997 | Dranoff |
| 5,904,920 A | 5/1999 | Dranoff |
| 5,985,290 A | 11/1999 | Jaffee |
| 6,033,674 A | 3/2000 | Jaffee |
| 6,277,368 B1 | 8/2001 | Hiserodt |
| 6,350,445 B1 | 2/2002 | Jaffee |
| 6,464,973 B1 | 10/2002 | Levitsky |
| 7,939,271 B2 | 5/2011 | Jooss et al. |
| 2006/0057127 A1 | 3/2006 | Liu et al. |
| 2007/0059315 A1* | 3/2007 | Jaffee ............. A61K 39/0011 424/155.1 |
| 2007/0231298 A1 | 10/2007 | Li et al. |
| 2008/0075744 A1 | 3/2008 | Hiserodt et al. |
| 2009/0028857 A1 | 1/2009 | Li et al. |
| 2014/0050701 A1* | 2/2014 | Zhong ............. C07K 14/005 424/93.2 |

FOREIGN PATENT DOCUMENTS

| | | | |
|---|---|---|---|
| WO | WO00/26676 | 5/2000 | |
| WO | WO00/72686 | 12/2000 | |
| WO | WO 2004030615 A2 * | 4/2004 | ........... C07K 14/47 |
| WO | WO 2008/109030 A2 | 9/2008 | |

OTHER PUBLICATIONS

Dunphy et al., "New approaches to identification of antigenic candidates for future prostate cancer immunology," Update Cancer Therapeutics (2006)1:273-284.
EPO, Communication—extended European search report dated Dec. 27, 2011 for European patent app. No. 11165306.9.
GeneCards online database, FAM136A, GeneCards ID (GCID) GC02M070523, printed Apr. 11, 2012.
Phosphositeplus online database, FAM136A, Reference No. Q96C01 (UniProtKB), printed Apr. 11, 2012.
HPRD, Human Protein Reference Database (online), FAM136A, printed Apr. 11, 2012.
NCBI, National Center for Biotechnology Information (online), GenBank ID No. EAW99815.1, modified Feb. 4, 2010, submitted by Celera Genomics Sep. 2, 2005.
NCBI, National Center for Biotechnology Information (online), Reference Sequence NM032822.2, modified Mar. 26, 2012, replaced prior NCBI sequence on Jun. 7, 2008.
NCBI, National Center for Biotechnology Information (online), Reference Sequence NP116211.2, modified Mar. 26, 2012, originally uploaded Jun. 7, 2008.
PRNewswire online press release, Cell Genesys, "Cell Genesys reports association between immune response and patient survival in Phase 2 trial of GVAX . . . " Feb. 15, 2008.
PCT International Search Report, mailed Jun. 9, 2010, for International Application No. PCT/US2009/004865, filed Aug. 27, 2009.
PCT Written Opinion, mailed Jun. 9, 2010, for International Application No. PCT/US2009/004865, filed Aug. 27, 2009.
PCT International Preliminary Report on Patentability, issued Mar. 1, 2011, for International Application No. PCT/US2009/004865, filed Aug. 27, 2009.
Abe et al., 1995, "Antitumor effect induced by granulocyte/macrophage-colony-stimulating factor gene-modified tumor vaccination: comparison of adenovirus- and retrovirus-mediated genetic transduction." J. Canc. Res. Clin. Oncol. 121: 587-592.

(Continued)

*Primary Examiner* — Janice Li
(74) *Attorney, Agent, or Firm* — Acuity Law Group, P.C.; Michael Whittaker

(57) ABSTRACT

The present invention relates to prostate cancer markers, compositions comprising such markers, and methods of using such markers to induce or increase an immune response against prostate cancer. An immune response against the markers correlates with an immune response, in particular a humoral immune response, against prostate cancer cells which immune response is preferably associated with prophylaxis of prostate cancer, treatment of prostate cancer, and/or amelioration of at least one symptom associated with prostate cancer.

6 Claims, 27 Drawing Sheets

(56) References Cited

OTHER PUBLICATIONS

Figure 1:
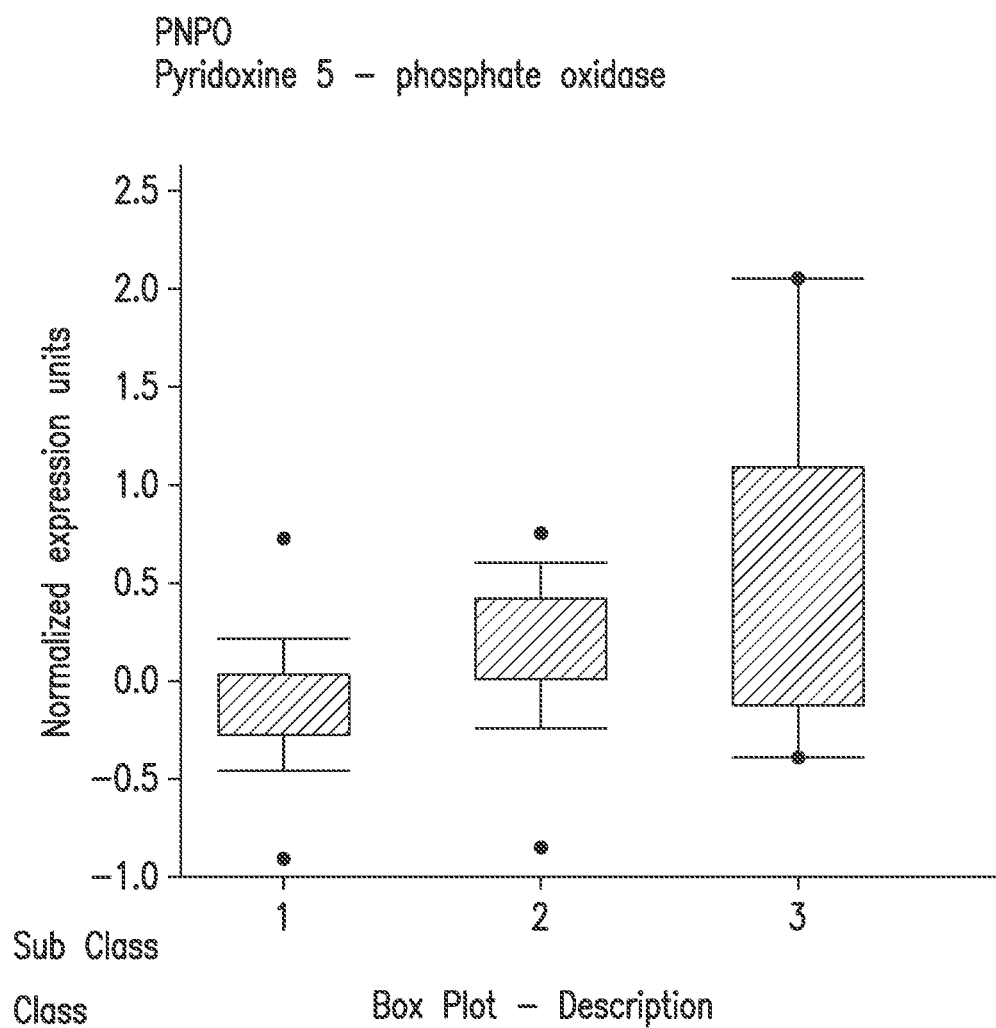

Adams et al., 1995, "Initial assessment of human gene diversity and expression patterns based upon 83 million nucleotides of cDNA sequence." Nature 377 (6547 SUPPL), 3-174.
Altschul et al., 1990, "Basic Local Alignment Search Tool." J. Mol. Biol. 215:403-410.
An et al., 2006, "A critical role for the histidine residues in the catalytic function of acyl-CoA: cholesterol acyltransferase catalysis: evidence for catalytic difference between ACAT1 and ACAT2." FEBS Lett. 580(11), 2741-2749.
Aoki et al., 1992, "Expression of murine interleukin 7 in a murine glioma cell line results in reduced tumorigenicity in vivo." Proc Natl Acad Sci USA. 89(9):3850-4.
Armstrong et al., 2002, "Cytokine modified tumor vaccines." Surg Oncol Clin N Am. 11(3):681-96.
Asano et al., 1997, "Conservation and diversity of eukaryotic translation initiation factor eIF3." J. Biol. Chem. 272(2):1101-1109.
Balakirev et al., 2003, "Otubains: a new family of cysteine proteases in the ubiquitin pathway." EMBO Rep. 4(5):517-522.
Bartee et al., 2004, "Down regulation of major histocompatibility complex class I by human ubiquitin ligases related to viral immune evasion proteins." J. Virol. 78(3): 109-1120.
Batzer et al., 1991, "Enhanced evolutionary PCR using oligonucleotides with inosine at the 3'-terminus." Nucleic Acid Res. 19:5081.
Bell et al., 1988, "Functional cooperativity between transcription factors UBF1 and SL1 mediates human ribosomal RNA synthesis." Science 241(4870):1192-1197.
Bennett et al., 1984, "Biochemical investigations on a patient with a defect in cytosolic acetoacetyl-CoA thiolase, associated with mental retardation." J. Inherit. Metab. Dis. 7(3):125-128.
Bilbe et al., 1992, "Restin: a novel intermediate filament-associated protein highly expressed in the Reed-Sternberg cells of Hodgkin's disease." EMBO J. 11(6):2103-2113.
Blank et al., 2005, "Interaction of PD-L1 on tumor cells with PD-1 on tumor-specific T cells as a mechanism of immune evasion: implications for tumor immunotherapy." Cancer Immunol. Immunother. 54:307-314.
Bodey et al., 2000, "Failure of Cancer Vaccines: The Significant Limitations of this Approach to Immunotherapy." Anticancer Res. 20(4):2665-76.
Bomont et al., 2005, "Unstable microtubule capture at kinetochores depleted of the centromere-associated protein CENP-F." EMBO J. 24(22):3927-3939.
Boon et al., 1997, "Cancer Tumor Antigens." Curr Opin Immunol. Oct. 1; 9(5):681-683.
Borello et al., 2002, "GM-CSF-based cellular vaccines: a review of the clinical experience." Growth Factor Rev. 13(2):185-93.
Bradford et al., 2006, "Cancer immunomics: using autoantibody signatures in the early detection of prostate cancer." Urol Oncol. May-Jun.;24(3):237-42.
Bruderer et al., 2004, "The AAA ATPase p97/VCP interacts with its alternative co-factors, Ufd1-Npl4 and p47, through a common bipartite binding mechanism." J Biol. Chem. 279(48):49609-16.
Burstein et al., 2005, "COMMD proteins, a novel family of structural and functional homologs of MURR1." J. Biol. Chem. 280(23):22222-32.
Cantrell et al., 1985, "Cloning, sequence, and expression of a human granulocyte/macrophage colony-stimulating factor." Proc. Natl. Acad. Sci. 82:6250-6254.
Cárcamo et al., 2006, "Galectin-8 binds specific beta1 integrins and induces polarized spreading highlighted by asymmetric lamellipodia in Jurkat T cells." Exp. Cell Res. 312(4):374-386.
Carlsson et al., 2007, "Affinity of galectin-8 and its carbohydrate recognition domains for ligands in solution and at the cell surface." Glycobiology 17(6):663-676.
Casiano et al., 2006, "Tumor-associated antigen arrays for the serological diagnosis of cancer." Mol. Cell. Proteomics. Oct.;5(10):1745-59.

Cha et al., 2006, "Inhibition of mixed-lineage kinase (MLK) activity during G2-phase disrupts microtubule formation and mitotic progression in HeLa cells." Cell. Signal. 18(1):93-104.
Chadee et al., 2004, "MLK3 is required for mitogen activation of B-Raf, ERK and cell proliferation." Nat. Cell Biol. 6(8):770-776.
Chang et al., 2000, "Immunogenetic Therapy of Human Melanoma Utilizing Autologous Tumor Cells Transduced to Secrete Granulocyte-Macrophage Colony-Stimulating Factor." Human Gene Therapy 11:839-850.
Chaudhuri et al.,. 1997, "Biochemical characterization of mammalian translation initiation factor 3 (eIF3). Molecular cloning reveals that p110 subunit is the mammalian homologue of *Saccharomyces cerevisiae* protein PrtI." J. Biol. Chem. 272(49):30975-83.
Chen et al., 1997, "Neuropilin-2, a novel member of the neuropilin family, is a high affinity receptor for the semaphorins Sema E and Sema IV but not Sema III." Neuron 19(3):547-559.
Chen et al., 1998, "Semaphorin-neuropilin interactions underlying sympathetic axon responses to class III semaphorins." Neuron 21(6):1283-1290.
Chen et al., 1997, "HEC binds to the seventh regulatory subunit of the 26 S proteasome and modulates the proteolysis of mitotic cyclins." J. Biol. Chem. 272(38):24081-24087.
Ciferri et al., 2005, "Architecture of the human ndc80-hcc1 complex, a critical constituent of the outer kinetochore." J. Biol. Chem. 280(32):29088-95.
Ciszak et al., 2006, "How dihydrolipoamide dehydrogenase-binding protein binds dihydrolipoamide dehydrogenase in the human pyruvate dehydrogenase complex." J. Biol. Chem. 281(1):648-55.
Coux et al., 1996, "Structure and functions of the 20S and 26S proteasomes." Annu. Rev. Biochem. 65:801-847.
Darrow et al., 1989, "The Role of HLA Class I Antigens in Recognition of Melanoma Cells by Tumor-Specific Cytotoxic T Lymphocytes." J. Immunol. 142:3329-35.
Defeo-Jones et al., 1991, "Cloning of cDNAs for cellular proteins that bind to the retinoblastoma gene product." Nature 352(6332):251-254.
DeLuca et al., 2006, "Kinetochore microtubule dynamics and attachment stability are regulated by Hec1." Cell 127(5):969-982.
DeLuca-Flaherty et al., 2006, "Uncoating protein (hsc70) binds a conformationally labile domain of clathrin light chain LCa to stimulate ATP hydrolysis." Cell 62(5):875-887.
Dou et al., 1996, "Cloning of human neuronatin gene and its localization to chromosome-20q 11.2-12: the deduced protein is a novel 'proteolipid'." Brain Res. 723(1-2):8-22.
Dou et al., 1996, "Structure and organization of the human neuronatin gene." Genomics 33(2):292-297.
Dranoff et al., 1993, "Vaccination of irradiated tumor cells engineered to secrete murine granulocyte-macrophage colony-stimulating factor stimulates potent, specific, and long-lasting anti-tumor immunity." PNAS 90:3539-3543.
Dunphy et al., 2005 , "Antigen-specific IgG elicited in subjects with prostate cancer treated withflt3 ligand." J. Immunother. May-Jun.;28(3):268-75.
Dworniczak et al., 1987, "Structure and expression of a human gene coding for a 71 kd heat shock 'cognate' protein." Nucleic Acids Res. 15(13):5181-5197.
Ermini et al., 2005, "Different glycoforms of the human GPI-anchored antigen CD52 associate differently with lipid microdomains in leukocytes and sperm membranes." Biochem. Biophys. Res. Commun. 338 (2):1275-1283.
Faber et al., 1998, "Huntingtin interacts with a family of WW domain proteins." Hum Mol Genet. 7(9):1463-74.
Fattaey et al., 1993, "Characterization of the retinoblastoma binding proteins RBP1 and RBP2." Oncogene 8(11):3149-3156.
Fearon et al., 1990, "Interleukin-2 Production by Tumor Cells Bypasses T Helper Function in the Generation of an Antitumor Response." Cell 60:397-403.
Feng et al., 2006, "CENP-F is a novel microtubule-binding protein that is essential for kinetochore attachments and affects the duration of the mitotic checkpoint delay." Chromosoma 115(4):320-329.
Feng et al., 2004, "The many faces of filamin: a versatile molecular scaffold for cell motility and signaling." Nat Cell Biol. 6(11):1034-38.

(56) References Cited

OTHER PUBLICATIONS

Filppula et al., 1998, "Delta3,5-delta2,4-dienoyl-CoA isomerase from rat liver. Molecular characterization." J. Biol. Chem. 273(1):349-355.
Forni et al., 1988, "Helper strategy in tumor immunology: Expansion of helper lymphocytes and utilization of helper lymphokines for experimental and clinical immunotherapy." Cancer and Met. Reviews 7:289-309.
Gallo et al., 1994, "Identification and characterization of SPRK, a novel src-homology 3 domain-containing proline-rich kinase with serine/threonine kinase activity." J. Biol. Chem. 269(21):15092-15100.
Gansbacher et al., 1990, "Retroviral Vector-mediated gamma interferon Gene Transfer into Tumor Cells Generates Potent and Long Lasting Antitumor Immunity." Cancer Res. 50:7820-7825.
Gansbacher et al., 1990, "Interleukin 2 Gene Transfer into Tumor Cells Abrogates Tumorigenicity and Induces Protective Immunity." J. Exp. Med. 172:1217-1224.
Gardiner et al., 2002, "Annotation of human chromosome 21 for relevance to Down syndrome: gene structure and expression analysis." Genomics 79(6):833-843.
Gasson, J., 1991, "Molecular Physiology of Granulocyte-Macrophage Colony-Stimulating Factor." Blood 77(6):1131-45.
Giger et al., 1998, "Neuropilin-2 is a receptor for semaphorin IV: insight into the structural basis of receptor function and specificity." Neuron 21(5):1079-1092.
Gilles et al., 1991, "Nucleoside diphosphate kinase from human erythrocytes. Structural characterization of the two polypeptide chains responsible for heterogeneity of the hexameric enzyme." J. Biol. Chem. 266 (14), 8784-8789.
Golumbeck et al., 1991, "Treatment of Established Renal Cancer by Tumor Cells Engineered to Secrete Interleukin-4." Science 254:713-716.
Gonzatti-Haces, et al., 1988, "Characterization of the TPR-MET oncogene p65 and the MET protooncogene p140 protein-tyrosine kinases." Proc. Natl. Acad. Sci. U.S.A. 85(1):21-25.
Granneman et al., 2003, "The human Imp3 and Imp4 proteins form a ternary complex with hMpp10, which only interacts with the U3 snoRNA in 60-80S ribonucleoprotein complexes." Nucleic Acids Res. 31(7):1877-1887.
Guo et al., 2004, "Identification and characterization of a novel cytoplasm protein ICF45 that is involved in cell cycle regulation." J. Biol. Chem. 279(51):53498-53505.
Halabi et al., 2003, "Prognostic model for predicting survival in men with HRPC." Journal of Clinical Oncology 21(7):1232-7.
Hammond et al., 2001, "In vitro selection and characterization of Bcl-X(L)-binding proteins from a mix of tissue-specific mRNA display libraries." J. Biol. Chem. 276(24):20898-20906.
Harding et al., 2006, "Humoral immune response induced to filamin B in patients with metastatic hormone-refractory GM-CSF-transduced allogenic prostate cancer vaccine (GVAX®)." Proceedings of the Annual Meeting of the Am. Association for Cancer Research 47:680, Abstract No. 2894.
Harding et al., 2007, "Identification of antibody responses induced in patients with metastatic hormone-refractory prostate cancer (HRPC) treated with a GM-CSF-transduced allogeneic prostate cancer therapy." Proceedings of the Annual Meeting of the Am. Association for Cancer Research 48:981, Abstract No. 4139.
Harrington et al., 2001, "Creation of genome-wide protein expression libraries using random activation of gene expression." Nat. Biotechnol. 19(5):440-445.
Hartmann et al., 1993, "A tetrameric complex of membrane proteins in the endoplasmic reticulum." Eur. J. Biochem. 214(2):375-381.
Hase et al., 2003, "Direct interaction with nup153 mediates binding of Tpr to the periphery of the nuclear pore complex." Mol. Biol. Cell 14(5):1923-1940.
Hiromasa et al., 2004, "Organization of the cores of the mammalian pyruvate dehydrogenase complex formed by E2 and E2 plus the E3-binding protein and their capacities to bind the E1 and E3 components." J. Biol. Chem. 279(8):6921-6933.

Hjelmqvist et al., 2002, "ORMDL proteins are a conserved new family of endoplasmic reticulum membrane proteins." Genome Biol. 3(6):1-16.
Hock et al., 1991, "Interleukin 7 Induces CD4+ T Cell-dependent Tumor Rejection." J. Exp. Med. 174:1291-1298.
Hom et al., 1991, "Common Expression of Melanoma Tumor-Associated Antigens Recognized by Human Tumor Infiltrating Lymphocytes: Analysis by Human Lymphocyte Antigen Restriction." J. Immunother. 10:153-164.
Huang et al., 1994, "Role of Bone Marrow-Derived Cells in Presenting MHC Class I-Restricted Tumor Antigens." Science 264:961-965.
Huang et al., 2003, "A specific splicing variant of SVH, a novel human armadillo repeat protein, is up-regulated in hepatocellular carcinomas." Cancer Res. Jul. 1;63(13):3775-82.
Huebner et al., 1985, "The Human Gene Encoding GM-CSF Is at 5q21-q32, the Chromosome Region Deleted in the 5q-Anomaly." Science 230(4731):1282-5.
Hurwitz et al., 1998, "CTLA-4 blockade synergizes with tumor-derived granulocyte-macrophage colony-stimulating factor for treatment of an experimental mammary carcinoma." Proc. Natl. Acad. Sci. U.S.A. 95:10067-10071.
Hurwitz et al., 2000, "Combination Immunotherapy of Primary Prostate Cancer in a Transegnic Mouse Model Using CTLA-4 Blockade," Cancer Research 60:2444-2448.
Imai et al., 2002,"Cloning and characterization of the highly expressed ETEA gene from blood cells of atopic dermatitis patients." Biochem. Biophys. Res. Commun. 297(5):1282-1290.
Inuzuka et al., 2005, "SERINC, an activity-regulated protein family, incorporates serine into membrane lipid synthesis." J. Biol. Chem. 280(42):35776-83.
Jaffee et al., 1995, "Gene Therapy: Its Potential Applications in the Treatment of Renal-Cell Carcinoma." Seminars in Oncology 22(1):81-91.
Jaffee et al., 2001, "Novel Allogeneic Granulocyte-Macrophage Colony-Stimulating Factor-Secreting Tumor Vaccine for Pancreatic Cancer: A Phase I Trial of Safety and Immune Activation." J. Clin. Oncol. 19:145-156.
Jantzen et al., 1990, "Nucleolar transcription factor hUBF contains a DNA-binding motif with homology to HMG proteins." Nature 344(6269):830-836.
Jindal et al., 1989, "Primary structure of a human mitochondrial protein homologous to the bacterial and plant chaperonins and to the 65-kilodalton mycobacterial antigen." Mol. Cell. Biol. 9(5)2279-83.
Kalies et al., 1996, "Membrane topology of the 12- and the 25-kDa subunits of the mammalian signal peptidase complex." J. Biol. Chem. 271(7):3925-3929.
Kamakaka et al., 1998, Sir- and silencer-independent disruption of silencing in Saccharomyces by Sas10p. Genetics 149(2):903-14.
Kang et al., 2004, "Genomic organization, tissue distribution and deletion mutation of human pyridoxine 5'-phosphate oxidase." Eur J Biochem. 271(12):2452-61.
Kawakami et al., 1992, "Shared Human Melanoma Antigens: Recognition by Tumor-Infiltrating Lymphocytes in HLA-A2.1-Transfected Melanomas." J. Immunol. 148:638-643.
Klein et al., 1976, "Properties of the K562 Cell Line, Derived from a Patient with Chronic Myeloid Leukemia." Int. J. Cancer 18:421-431.
Koe et al., 2001, "The large subunit of the mammalian mitochondrial ribosome. Analysis of the complement of ribosomal proteins present." J. Biol. Chem. 276(47):43958-69.
Kondo et al., 1997, "p47 is a cofactor for p97-mediated membrane fusion." Nature. 388(6637):75-8.
Krangel et al., 1987, "Structurally divergent human T cell receptor gamma proteins encoded by distinct C gamma genes." Science 237(4810):64-67.
Kreft et al., 2006, "Membrane topology of the yeast endoplasmic reticulum-localized ubiquitin ligase Doa10 and comparison with its human ortholog TEB4 (MARCH-VI)." J. Biol. Chem. 281(8):4646-4653.
Krull et al., 2004, "Nucleoporins as components of the nuclear pore complex core structure and Tpr as the architectural element of the nuclear basket." Mol. Biol. Cell 15(9):4261-4277.

(56) References Cited

OTHER PUBLICATIONS

Kubota et al., 1994, "Identification of six Tcp-1-related genes encoding divergent subunits of the TCP-1-containing chaperonin." Curr. Biol. 4(2):89-99.
Kume et al., 1991, "The glycine cleavage system. Molecular cloning of the chicken and human glycine decarboxylase cDNAs and some characteristics involved in the deduced protein structures." J. Biol. Chem. 266(5):3323-3329.
Kurochkin et al., 2001, "ALEXI, a novel human armadillo repeat protein that is expressed differentially in normal tissues and carcinomas." Biochem. Biophys. Res. Commun. 280:340-347.
Kurschner et al., 1998, "CIPP, a novel multivalent PDZ domain protein, selectively interacts with Kir4.0 family members, NMDA receptor subunits, neurexins, and neuroligins." Mol. Cell. Neurosci. 11(3),:161-172.
Lee et al., 1997, "Genetic Immunotherapy of Established Tumors with Adenovirus-Murine Granulocyte-Macrophage Colony-Stimulating Factor." Human Gene Therapy 8:187-193.
Lehner et al., 2004, "A protein interaction framework for human mRNA degradation," Genome Res. 14(7):1315-1323.
Lerman et al., 2000, "The 630-kb lung cancer homozygous deletion region on human chromosome 3p21.3: identification and evaluation of the resident candidate tumor suppressor genes. The International Lung Cancer Chromosome 3p21.3 Tumor Suppressor Gene Consortium." Cancer Res. 60(21):6116-6133.
Leung et al., 1996, "Cloning of novel kinectin splice variants with alternative C-termini: structure, distribution and evolution of mouse kinectin." Immunol. Cell Biol. Oct.;74(5)421-33.
Li et al., 1995, "Evidence for a regulated interaction between heterotrimeric G proteins and caveolin." J. Biol. Chem. 270(26):15693-15701.
Liao et al., 1995, "CENP-F is a protein of the nuclear matrix that assembles onto kinetochores at late G2 and is rapidly degraded after mitosis." J. Cell Biol. 130(3):507-518.
Lilley et al., 2005, "Multiprotein complexes that link dislocation, ubiquitination, and extraction of misfolded proteins from the endoplasmic reticulum membrane." Proc. Natl. Acad. Sci. U.S.A. 102(40):14296-14301.
Linstedt et al., 1993, "Giantin, a novel conserved Golgi membrane protein containing a cytoplasmic domain of at least 350 kDa." Mol. Biol. Cell 4(7):679-693.
Liou et al., 1997, "Elucidation of the subunit orientation in CCT (chaperonin containing TCP1) from the subunit composition of CCT5 micro-complexes." EMBO J. 16(14):4311-4316.
Little et al., 1992, "Molecular definition of an elusive third HLA-A9 molecule: HLA-A9.3." Immunogenetics 35(1):41-5.
Liu et al., 2005, "Investigating the allosterism of acyl-CoA:cholesterol acyltransferase (ACAT) by using various sterols: in vitro and intact cell studies." Biochem. J. 391(PT 2):389-397.
Lo et al., 2006, "PGAM5, a Bcl-XL-interacting Protein, Is a Novel Substrate for the Redox-regulated Keap1-dependent Ubiquitin Ligase Complex." J. Biol. Chem. 281(49):37893-37903.
Lozzio et al., 1975, "Human Chronic Myelogenous Leukemia Cell-Line With Positive Philadelphia Chromosome." Blood 45(3):321-334.
Mach et al., 2000, "Cytokine-secreting Tumor Cell Vaccines." Curr. Opin. Immunol. 12(5):571-5.
Mach et al., 2000, "Differences in Dendritic Cells Stimulated in vivo by Tumors Engineered to Secrete Granulocyte-Macrophage Colony-Stimulating Factor or Flt3-Ligand." Cancer Res. 60(12):3239-46.
Maeda et al., 2004, "The T cell receptor gamma chain alternate reading frame protein (TARP), a prostate-specific protein localized in mitochondria." J. Biol. Chem. 279(23):24561-24568.
Mao et al., 1997, "T-cell oncogene rhombotin-2 interacts with retinoblastoma-binding protein 2." Oncogene 14(13):1531-1539.
McNeel et al., 2000, "Antibody immunity to prostate cancer associated antigens can be detected in the serum of patients with prostate cancer." J Urol. 164(5):1825-9.
McNeil et al., 1990, "Anti-phospholipid antibodies are directed against a complex antigen that includes a lipid-binding inhibitor of coagulation: beta 2-glycoprotein 1 (apolipoprotein H)." Proc. Natl. Acad. Sci. U.S.A. 87(11):4120-24.
Methot et al., 1997, "The human homologue of the yeast Prt1 protein is an integral part of the eukaryotic initiation factor 3 complex and interacts with p170." J. Biol. Chem. 272(2):1110-1116.
Meyer et al., 1998, "The p47 co-factor regulates the ATPase activity of the membrane fusion protein, p97." FEBS Lett. 437(3):255-57.
Michel et al., 2005, "PATJ connects and stabilizes apical and lateral components of tight junctions in human intestinal cells." J. Cell. Sci. 118(PT 17):4049-4057.
Mina-Osorio et al., 2007, "A role for galectin-3 in CD13-mediated homotypic aggregation of monocytes." Biochem. Biophys. Res. Commun. 353(3):605-610.
Nagai et al., 1998, "Irradiated tumor cells adenovirally engineered to secrete granulocye/macrophage-colony-stimulating factor establish antitumor immunity and eliminate pre-existing tumors in syngeneic mice." Cancer Immunol. Immunother. 47:72-80.
Needleman et al., 1970, "A General Method Applicable to the Search for Similarities in the Amino Acid Sequence of Two Proteins." J. Mol. Biol. 48:443-453.
Nemunaitis et al., 2004, "Granulocyte-Macrophage Colony-Stimulating Factor Gene-Modified Autologous Tumor Vaccines in Non-Small-Cell Lung Cancer." J. Natl. Cancer Inst. 96(4):326-3.
Ngo et al., 1998, "Absence of pyridoxine-5'-phosphate oxidase (PNPO) activity in neoplastic cells: isolation, characterization, and expression of PNPO cDNA." Biochemistry 37(21):7741-8.
N'Guyen et al., 1985, "The HLA-AW24 gene: sequence, surroundings and comparison with the HLA-A2 and HLA-A3 genes."Immunogenetics 21(5):479-89.
Oettgen et al., 1991, The History of Cancer Immunotherapy, Biologic Therapy of Cancer, Chap. 6, pp. 87-119; Devita et al. (eds.).
Ohtsuka et al., 1985, "An Alternative Approach to Deoxyoligonucleotides as Hybridization Probes by Insertion of Deoxyinosine at Ambiguous Codon Positions." J. Biol. Chem. 260:2605-2608.
Padovani et al., 2006, "Energetics of interaction between the G-protein chaperone, MeaB, and B12-dependent methylmalonyl-CoA mutase." J. Biol. Chem. 281(26):17838-17844.
Pan et al., 2007, "Neuropilin-1 binds to VEGF121 and regulates endothelial cell migration and sprouting." J. Biol. Chem. 282(33):24049-24056.
Pang et al., 1995, "Prostate Tissue Specificity of a Prostate-Specific Antigen Promoter Isolated from a Patient with Prostate Cancer." Hum. Gene Ther. 6(11):1417-1426.
Pearson et al., Improved Tools for Biological Sequence Comparison. Proc. Nat'l. Acad. Sci. USA 85:2444-2448 (1988).
Pelicci et al., 1987, "Molecular diversity of the human T-gamma constant region genes." Science 237(4818):1051-1055.
Peters et al., 2003, "RNA editing and regulation of *Drosophila* 4f-rnp expression by sas-10 antisense readthrough mRNA transcripts." RNA. 9(6)698-710.
Pierre et al., 1994, Molecular characterization of two functional domains of CLIP-170 in vivo J. Cell. Sci. 107(PT 7):1909-1920.
Pierre et al., 1992, "CLIP-170 links endocytic vesicles to microtubules." Cell 70(6):887-900.
Player et al., 2003, "Identification of TDE2 gene and its expression in non-small cell lung cancer." Int. J. Cancer 107(2):238-243.
Pons et al., 1988, "Cloning and cDNA sequence of the dihydrolipoamide dehydrogenase component human alpha-ketoacid dehydrogenase complexes." Proc. Natl. Acad. Sci. U.S.A. 85(5):1422-1426.
Popowicz et al., 2006, "Filamins: promiscuous organizers of the cytoskeleton." Trends Biochem Sci. 31(7):411-9.
Porgador et al., 1994, "Immunotherapy of Tumor Metastasis via Gene Therapy." Nat. Immun. 13(2-3):113-30.
Qin et al., 2006, "Development of a "reverse capture" autoantibody microarray for studies of antigen-autoantibody profiling." Proteomics. (6)3199-3209.
Raz et al., 1991, "Molecular cloning and chromosomal mapping of a human galactoside-binding protein." Cancer Res. 51(8):2173-2178.

(56) References Cited

OTHER PUBLICATIONS

Reymond et al., 2001, "From PREDs and open reading frames to cDNA isolation: revisiting the human chromosome 21 transcription map." Genomics 78(1-2):46-54.
Robertson, SP, 2004, "Molecular pathology of filamin A: diverse phenotypes, many functions." Clin Dysmorphol. Jul.;13(3):123-31.
Roobol et al., 1995, "Cytoplasmic chaperonin complexes enter neurites developing in vitro and differ in subunit composition within single cells." J. Cell. Sci. 108(PT 4):1477-1488.
Rosengard et al., 1989, "Reduced Nm23/Awd protein in tumor metastasis and aberrant *Drosophila* development." Nature 342(6246):177-180.
Rossolini et al., 1994, "Use of Deoxyinosine-containing primers vs degenerate primers for polymerase chain reactioni based on ambiguous sequence information." Mol. Cell. Probes 8:91-98.
Sahin et al., 1995, "Human neoplasms elicit multiple specific immune responses in the autologous host." Proc Natl Acad Sci U S A. Dec. 5;92(25):11810-3.
Salgia et al., 2003 , "Vaccination with Irradiated Autologous Tumor Cells Engineered to Secrete Granulocyte-Macrophage Colony-Stimulating Factos Augments Antitumor Immunity in Some Patients with Metastatic Non-Small-Cell Lung Carcinoma." J. Clin. Oncol. 21:624-30.
Scharf et al., 1998, "Identification of a candidate modifying gene for spinal muscular atrophy by comparative genomics." Nat. Genet. Sep.;20(1):83-6.
Scherer et al., 1997, "Association of phosphofructokinase-M with caveolin-3 in differentiated skeletal myotubes. Dynamic regulation by extracellular glucose and intracellular metabolites." J. Biol. Chem. 272(33):20698-20705.
Schram et al., 1987, "Human peroxisomal 3-oxoacyl-coenzyme A thiolase deficiency." Proc. Natl. Acad. Sci. U.S.A. 84(8):2494-2496.
Seelig et al., 1994, "Macrogolgin—a new 376 kD Golgi complex outer membrane protein as target of antibodies in patients with rheumatic diseases and HIV infections." J. Autoimmun. 7(1):67-91.
Seko et al., 2003, "Activation of RhoA and inhibition of myosin phosphatase as important components in hypertension in vascular smooth muscle." Circ. Res. 92(4):411-418.
Silverman et al., 2004, "Human Rif1, ortholog of a yeast telomeric protein, is regulated by ATM and 53BPI and functions in the S-phase checkpoint." Genes Dev. 18(17):2108-2119.
Simons et al., 1997, "Bioactivity of Autologous Renal Cell Carcinoma Vaccines Generated by ex Vivo Granulocyte-Macrophage Colony-Stimulating Factor Gene Transfer." Cancer Res. 57:1537-46.
Simons et al., 1999, "Induction of Immunity to Prostate Cancer Antigens: Results of a Clinical Trial of Vaccination with Irradiated Autologous Prostate Tumor Cells Engineered to Secrete Granulocyte-Macrophage Colony-Stimulating Factor using ex Vivo Gene Transfer." Cancer Res. 59:5160-5168.
Simpson et al., 2000, "Systematic subcellular localization of novel proteins identified by large-scale cDNA sequencing." EMBO Rep. 1(3):287-292.
Smith et al., 1981, "Comparison of Biosequences." Adv. Appl. Math. 2:482-489.
Sohda et al., 1994, "Molecular cloning and sequence analysis of a human 372-kDA protein localized in the Golgi complex." Biochem. Biophys. Res. Commun. 205(2):1399-1408.
Soiffer et al., 2003, "Molecular Cloning and Sequence Analysis of a Human 372-kDA Protein Localized in the Golgi Complex." J. Clin. Oncol. 21:3343-50.
Soiffer et al., 1998, "Vaccination with Irradiated, Autologous Melanoma Cells Engineered to Secrete Granulocyte-Macrophage Colony-Stimulating Factor by Adenoviral-Mediated Gene Transfer Augments Antitumor Immunity in Patients with Metastatic Melanoma." Proc. Natl. Acad. Sci. U.S.A. 95:13141-13146.
Soker et al., 1998, "Neuropilin-1 is expressed by endothelial and tumor cells as an isoform-specific receptor for vascular endothelial growth factor." Cell 92(6):735-745.

Song et al., 1995, "Association of a RING finger protein with the cytoplasmic domain of the human type-2 tumor necrosis factor receptor." Biochem. J. 309(PT 3):825-829.
Sonnichsen et al., 1998, "A role for giantin in docking COPI vesicles to Golgi membranes." J. Cell Biol. 140(5):1013-1021.
Strausberg et al., 2002, "Mammalian Gene Collection Program Team. Generation and initial analysis of more than 15,000 full-length human and mouse cDNA sequences." Proc. Natl. Acad. Sci. U.S.A. Dec. 24;99(26):16899-903.
Sueishi et al., 2000, "The forkhead-associated domain of Ki-67 antigen interacts with the novel kinesin-like protein Hk1p2." J. Biol. Chem. 275(37):28888-28892.
Suzuki et al., 2001, "Structural compensation for the deficit of rRNA with proteins in the mammalian mitochondrial ribosome. Systematic analysis of protein components of the large ribosomal subunit from mammalian mitochondria." J. Biol. Chem. 276(24):21724-21736.
Takahashi et al., 1998, "Semaphorins A and E act as antagonists of neuropilin-1 and agonists of neuropilin-2 receptors." Nat. Neurosci. 1(6):487-493.
Tang et al., 1996, "Molecular cloning of caveolin-3, a novel member of the caveolin gene family expressed predominantly in muscle." J. Biol. Chem. 271(4):2255-2261.
Tassi et al., 1999, "Human JIK, a novel member of the STE20 kinase family that inhibits JNK and is negatively regulated by epidermal growth factor." J. Biol. Chem. 274(47):33287-33295.
Teng et al., 1991, "Long-term Inhibition of Tumor Growth by Tumor Necrosis Factor in the Absence of Cachexia or T-cell Immunity." PNAS 88:3535-3539.
Thomas et al., 2004, "Mesothelin-specific CD8+ T Cell Responses Provide Evidence of In vivo Cross-Priming by Antigen-Presenting Cells in Vaccinated Pancreatic Cancer Patients." J. Exp. Med. 200(3):297-306.
Tijssen, P, 1993, Laboratory Techniques in Biochemistry and Molecular Biology—Hybridization with Nucleic Acid Probes part 1 chapter 2, "Overview of principles of hybridization and the strategy of nucleic acid probe assays." Elsevier, New York.
Townsley et al., 1997, "Dominant-negative cyclin-selective ubiquitin carrier protein E2-C/UbcH10 blocks cells in metaphase." Proc. Natl. Acad. Sci. U.S.A. 94(6):2362-2367.
Trauger et al., 2002, "Kinetic mechanism for human Rho-Kinase II (ROCK-II)." Biochemistry 41(28):8948-8953.
Tsurumi et al., 1996, "cDNA cloning and functional analysis of the p97 subunit of the 26S proteasome, a polypeptide identical to the type-1 tumor-necrosis-factor-receptor-associated protein-2/55.11." Eur. J. Biochem. 239(3):912-921.
Twells et al., The sequence and gene characterization of a 400-kb candidate region for IDDM4 on chromosome 11q13, Genomics 72: 231-242, 2001.
Usui et al., 1997, "cDNA cloning and mRNA expression analysis of the human neuronatin. High level expression in human pituitary gland and pituitary adenomas." J. Mol. Neurosci. 9(1):55-60.
Vaccaro et al., 2001, "Distinct binding specificity of the multiple PDZ domains of INADL, a human protein with homology to INAD from *Drosophila melanogaster*." J. Biol. Chem. 276(45):42122-42130.
Valdmanis et al., 2007, "Mutations in the KIAA0196 Gene at the SPG8 Locus Cause Hereditary Spastic Paraplegia." Am J Hum Genet. Jan.;80(1):152-61.
Valentin et al., 1992, "The distribution of the CDW52 molecule on blood cells and characterization of its involvement in T cell activation." Transplantation 54(1):97-104.
van Elsas et al., 1999, "Combination Immunotherapy of B16 Melanoma Using Anti-Cytotoxic T Lymphocyte-associated Antigen 4 (CTLA-4) and Granulocyte/Macrophase Colony-Stimulating Factor (GM-CSF)-producing Vaccines Induces Rejection of Subcutaneous and Metastatic Tumors Accompanied by Autoimmune Depigmentation." J. Exp. Med. 190(3):355-366.
Varambally et al., 2005, "Integrative genomic and proteomic analysis of prostate cancer reveals signatures of metastatic progression." Cancer Cell. Nov.;8(5):393-406.

(56) References Cited

OTHER PUBLICATIONS

Venner et al., 1990, "Nucleotide sequences and novel structural features of human and Chinese hamster hsp60 (chaperonin) gene families." DNA Cell Biol. 9(8):545-552.

Voit et al., 1995, "Activation of mammalian ribosomal gene transcription requires phosphorylation of the nucleolar transcription factor UBF." Nucleic Acids Res. 23(14):2593-2599.

Wang et al., 2005, "Autoantibody signatures in prostate cancer." N Engl J Med. Sep. 22;353(12):1224-35.

Wang et al., 1999, "Oligomeric complexes involved in translocation of proteins across the membrane of the endoplasmic reticulum." FEBS Lett. 457(3):316-322.

Watanabe et al., 2006, "CD52 is a novel costimulatory molecule for induction of CD4+ regulatory T cells." Clin. Immunol. 120(3):247-259.

Westendorf et al., 1998, "M phase phosphoprotein 10 is a human U3 small nucleolar ribonucleoprotein component." Mol. Biol. Cell 9(2):437-449.

Witke et al., 1998, "In mouse brain profilin I and profilin II associate with regulators of the endocytic pathway and actin assembly." EMBO J. 17(4):967-976.

Wong et al., 1996, "Involvement of p90rsk in neurite outgrowth mediated by the cell adhesion molecule LI." J. Biol. Chem. 271(30):18217-18223.

Xing et al., 1996, "Coupling of the RAS-MAPK pathway to gene activation by RSK2, a growth factor-regulated CREB kinase." Science 273(5277):959-963.

Xu et al., 2004, "Human Rif1 protein binds aberrant telomeres and aligns along anaphase midzone microtubules." J. Cell Biol. 167(5):819-830.

Ye et al., 2001, "The AAA ATPase Cdc48/p97 and its partners transport proteins from the ER into the cytosol." Nature. Dec. 6;414(6864):652-6.

Ye, Y et al., 2005, "Inaugural Article: Recruitment of the p97 ATPase and ubiquitin ligases to the site of retrotranslocation at the endoplasmic reticulum membrane." Proc. Natl. Acad. Sci. U.S.A. 102(40):14132-14138.

Yu et al., 2007, "Galectin-3 interaction with Thomsen-Friedenreich disaccharide on cancer-associated MUC1 causes increased cancer cell endothelial adhesion." J. Biol. Chem. 282(1):773-781.

Zanin-Zhorov et al., 2006, "Heat shock protein 60 enhances CD4+ CD25+ regulatory T cell function via innate TLR2 signaling." J. Clin. Invest. 116(7):2022-2032.

Zhang et al., 2000, "Cloning of DPK, a novel dendritic cell-derived protein kinase activating the ERK1/ERK2 and JNK/SAPK pathways." Biochem. Biophys. Res. Commun. 274(3):872-879.

Zhao et al., 1995, "RSK3 encodes a novel pp90rsk isoform with a unique N-terminal sequence: growth factor-stimulated kinase function and nuclear translocation." Mol. Cell. Biol. 15(8):4353-4363.

* cited by examiner

FIG. 3A: G-9803 Trial Design
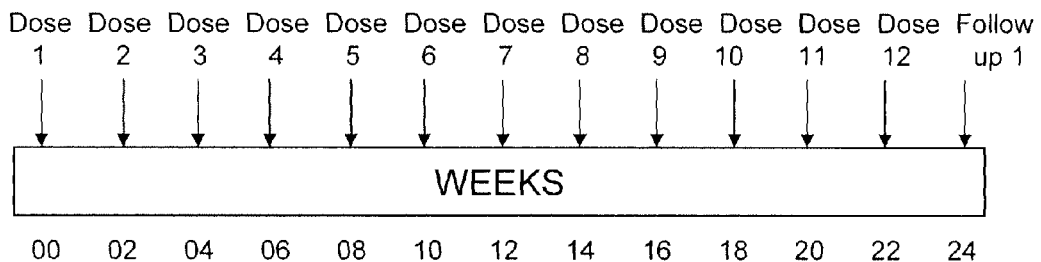
Metastatic low dose (500/100 q2 wks – Low Dose) n=24
Metastatic high dose (500/300 q2 wks – High Dose) n=10
PSA-rising low dose (500/100 q2 wks – Low Dose) n=21
FIG. 3B: G-0010 Trial Design
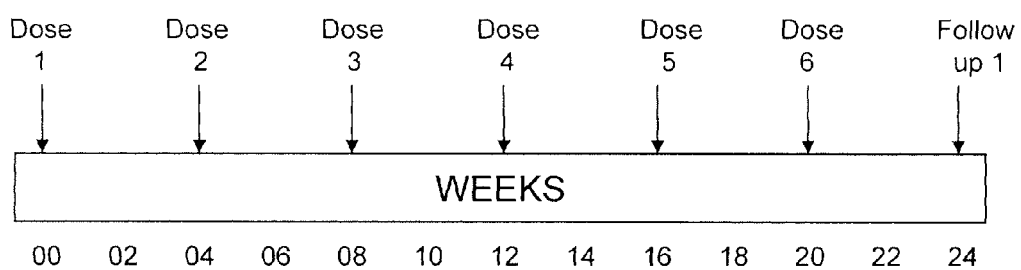
Dose 1 (100 q4 wks x6 – Low Dose) n=3
Dose 2A (200 q4 wks x6 – Low Dose) n=29
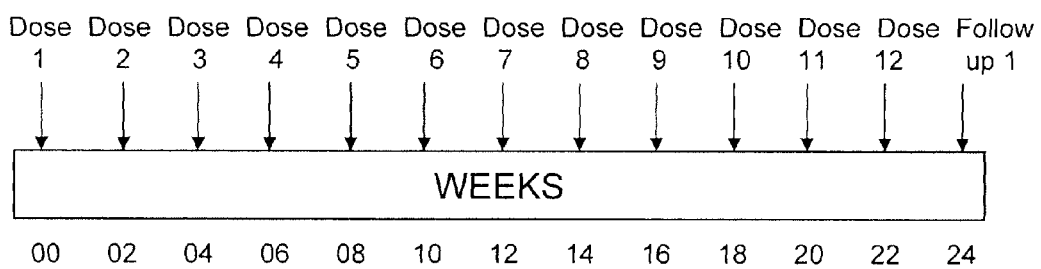
Dose 2B (200 q2 wks x12 – Mid Dose) n=24
Dose 3/4 (300 q2 wks x12 – High Dose) n=3
(500/300 q2 wks – High Dose) n=19

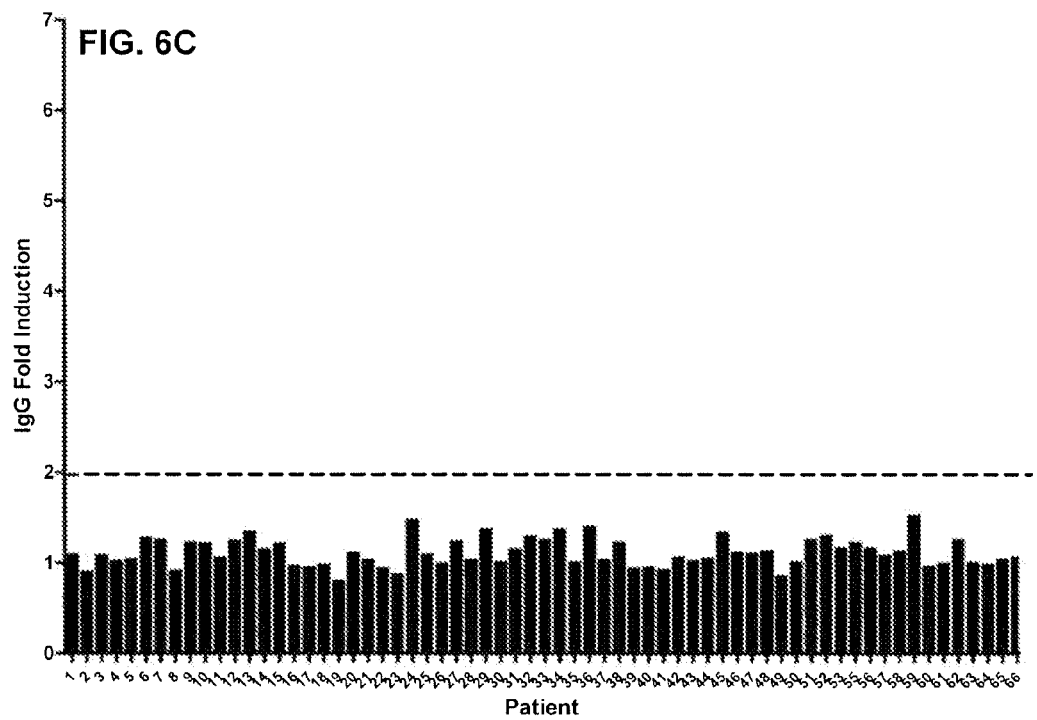
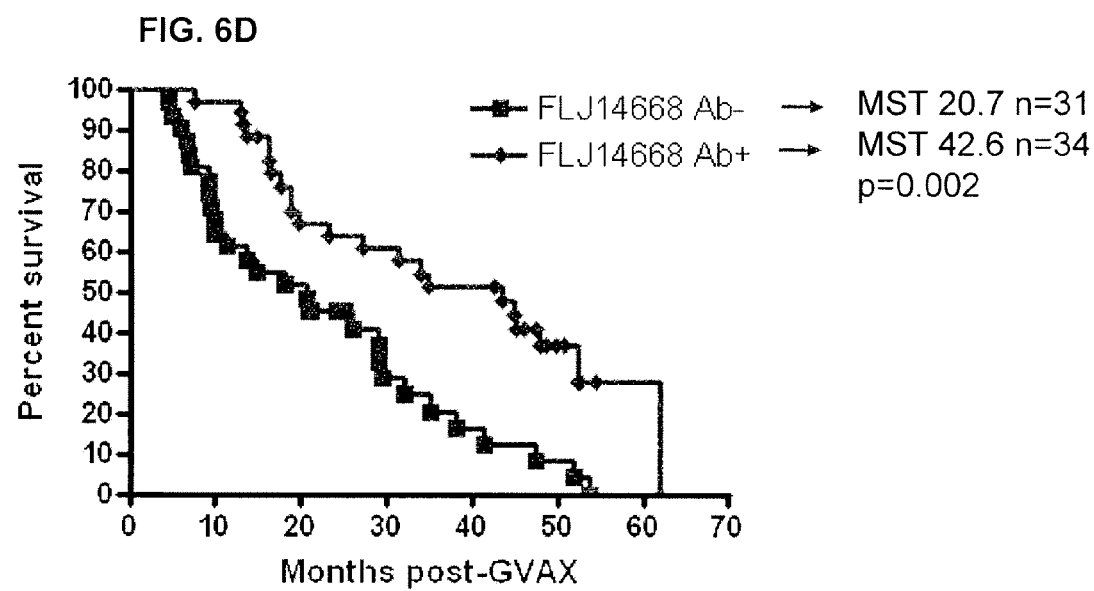

5.60 ±0.46 n=37    9.62 ±1.13
n=29              p=0.000777

5.16 ±0.49 n=32    9.44 ±0.96
n=34              p=0.0002

MST=34 months, n=36
MST=21 months, n=33
p=0.0503; HR=0.5999

METHODS AND COMPOSITIONS FOR TREATING PROSTATE CANCER OR INDUCING A HUMORAL IMMUNE RESPONSE AGAINST PROSTATE CANCER

This application is a divisional of application Ser. No. 12/546,399, filed Aug. 24, 2009, now U.S. Pat. No. 8,840,881, issued Sep. 23, 2014, which claims the benefit of U.S. Provisional Application No. 61/092,676, filed Aug. 28, 2008, all of which are hereby incorporated in their entirety including all tables, figures, and claims.

1. FIELD OF THE INVENTION

The present invention relates to prostate cancer markers, compositions comprising such markers, and methods of using such markers and compositions to induce or increase an immune response against prostate cancer. An immune response against the markers correlates with an immune response, in particular a humoral immune response, against prostate cancer cells which immune response is preferably associated with prophylaxis of prostate cancer, treatment of prostate cancer, and/or amelioration of at least one symptom associated with prostate cancer.

2. BACKGROUND

The immune system plays a critical role in the pathogenesis of a wide variety of cancers. When cancers progress, it is widely believed that the immune system either fails to respond sufficiently or fails to respond appropriately, allowing cancer cells to grow. Currently, standard medical treatments for cancer including chemotherapy, surgery, radiation therapy and cellular therapy have clear limitations with regard to both efficacy and toxicity. To date, these approaches have met with varying degrees of success dependent upon the type of cancer, general health of the patient, stage of disease at the time of diagnosis, etc. Improved strategies that combine specific manipulation of the immune response to cancer in combination with standard medical treatments may provide a means for enhanced efficacy and decreased toxicity.

One therapeutic approach to cancer treatment involves the use of genetically modified tumor cells which express cytokines locally at the vaccine site. Activity has been demonstrated in tumor models using a variety of immunomodulatory cytokines, including IL-4, IL-2, TNF-alpha, G-CSF, IL-7, IL-6 and GM-CSF, as described in Golumbeck P T et al., Science 254:13-716, 1991; Gansbacher B et al., J. Exp. Med. 172:1217-1224, 1990; Fearon E R et al., Cell 60:397-403, 1990; Gansbacher B et al., Cancer Res. 50:7820-25, 1990; Teng M et al., PNAS 88:3535-3539, 1991; Columbo M P et al., J. Exp. Med. 174:1291-1298, 1991; Aoki et al., Proc Natl Acad Sci USA. 89(9):3850-4, 1992; Porgador A, et al., Nat Immun. 13(2-3):113-30, 1994; Dranoff G et al., PNAS 90:3539-3543, 1993; Lee C T et al., Human Gene Therapy 8:187-193, 1997; Nagai E et al., Cancer Immunol. Immunother. 47:2-80, 1998 and Chang A et al., Human Gene Therapy 11:839-850, 2000, respectively. The use of autologous cancer cells as vaccines to augment anti-tumor immunity has been explored for some time. See, e.g., Oettgen et al., "The History of Cancer Immunotherapy", In: Biologic Therapy of Cancer, Devita et al. (eds.) J. Lippincot Co., pp 87-199, 1991; Armstrong T D and Jaffee E M, Surg Oncol Clin N Am. 11(3):681-96, 2002; and Bodey B et al., Anticancer Res 20(4):2665-76, 2000).

Several phase I/II human trials using GM-CSF-secreting autologous or allogeneic tumor cell vaccines have been performed (Simons et al. Cancer Res 1999 59:5160-8; Soiffer et al. Proc Natl Acad Sci USA 1998 95:13141-6; Simons et al. Cancer Res 1997 57:1537-46; Jaffee et al. J Clin Oncol 2001 19:145-56; Salgia et al. J Clin Oncol 2003 21:624-30; Soiffer et al. J Clin Oncol 2003 21:3343-50; Nemunaitis et al. J Natl Cancer Inst. 2004 Feb. 18 96(4): 326-31; Borello and Pardoll, Growth Factor Rev. 13(2): 185-93, 2002; and Thomas et al., J. Exp. Med. 200(3)297-306, 2004).

Administration of genetically modified GM-CSF-expressing cancer cells to a patient results in an immune response and preliminary clinical efficacy against prostate and other cancers has been demonstrated in Phase I/II clinical trails. However, there remains a need for improved methods and compositions for increasing the effectiveness of such therapies.

These and other needs are provided by the present invention.

3. SUMMARY

The present invention provides prostate cancer markers, compositions comprising such markers, and methods of using such markers to induce or increase an immune response against prostate cancer. An immune response against the markers correlates with an immune response, in particular a humoral immune response, against prostate cancer cells which immune response is preferably associated with prophylaxis of prostate cancer, treatment of prostate cancer, and/or amelioration of at least one symptom associated with prostate cancer.

Thus, in a first aspect, the invention provides a composition for the treatment of prostate cancer in a subject, the composition comprising one or more populations of cells genetically modified to express the coding sequence for a cytokine and the coding sequence of one or more prostate tumor-associated antigens selected from the group consisting of HLA-A24, FLJ14668, Cardiolipin, Neuronatin (NNAT), Selenoprotein (SELS), HIG1 domain family, member 2A (HIGD2A), Signal sequence receptor, gamma (SSR3) and Neuropilin 2 (NRP2). In some embodiments, the composition comprises one or more populations of cells genetically modified to express the coding sequence for a cytokine and the coding sequence of one, two, three, four, five, six, seven or eight prostate tumor-associated antigens selected from the group consisting of HLA-A24, FLJ14668, Cardiolipin, NNAT, SELS, HIGD2A, SSR3 and NRP2.

In another aspect, the invention provides a method for the treatment of prostate cancer in a subject, comprising administering a composition to a subject with prostate cancer, the composition comprising one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a cytokine and the coding sequence of one, two, three, four, five, six, seven or eight prostate tumor-associated antigens selected from the group consisting of HLA-A24, FLJ14668, Cardiolipin, NNAT, SELS, HIGD2A, SSR3 and NRP2.

In another aspect, the invention provides a method for inducing a de novo immune response in a subject against one or more prostate tumor-associated antigens, comprising administering a composition to a subject with prostate cancer, the composition comprising one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a cytokine and the coding sequence of one, two, three, four, five, six, seven or eight prostate tumor-associated antigens selected from the group consisting of HLA-A24, FLJ14668, Cardiolipin, NNAT, SELS, HIGD2A, SSR3 and NRP2.

In another aspect, the invention provides a method for increasing an immune response in a subject against one or more prostate tumor-associated antigens, comprising administering a composition to a subject with prostate cancer, the composition comprising one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a cytokine and the coding sequence of one, two, three, four, five, six, seven or eight prostate tumor-associated antigens selected from the group consisting of HLA-A24, FLJ14668, Cardiolipin, NNAT, SELS, HIGD2A, SSR3 and NRP2.

In some embodiments, the subject is a mammal. In some embodiments, the subject is a human. In some embodiments, the immune response is a humoral immune response. In some embodiments, the immune response is a cellular immune response.

In some embodiments, the genetically modified cells are rendered proliferation incompetent by irradiation.

In some embodiments, administration of the composition comprising one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2 results in enhanced therapeutic efficacy relative to administration of a composition comprising a single population of cells genetically modified to express the coding sequence for a cytokine or the coding sequence of one or more said prostate tumor-specific antigens alone. In some embodiments, enhanced therapeutic efficacy is measured by increased overall survival time. In some embodiments, enhanced therapeutic efficacy is measured by increased progression-free survival. In some embodiments, enhanced therapeutic efficacy is measured by decreased tumor size.

In some embodiments of the compositions described herein, the same population of cells is genetically modified to express the coding sequence for a cytokine and one or more prostate tumor-associated antigens selected from the group consisting of HLA-A24, FLJ14668, Cardiolipin, NNAT, SELS, HIGD2A, SSR3 and NRP2. In some embodiments, the population of genetically modified cells are autologous. In some embodiments, the population of genetically modified cells are allogeneic. In some embodiments, the population of genetically modified cells are bystander cells.

In some embodiments of the compositions and methods provided herein, two different populations of cells are genetically modified to express the coding sequence for a cytokine and one or more prostate tumor-associated antigens selected from the group consisting of HLA-A24, FLJ14668, Cardiolipin, NNAT, SELS, HIGD2A, SSR3 and NRP2. In some embodiments, one of the populations of genetically modified cells are autologous. In some embodiments, one of the populations of genetically modified cells are allogeneic. In some embodiments, one of the population of genetically modified cells are bystander cells. In some embodiments of the compositions described herein, a first population of cells comprise tumor cells genetically modified to express the coding sequence of a cytokine, and a second population of cells comprise bystander cells genetically modified to express the coding sequence for one or more prostate tumor-associated antigens selected from the group consisting of HLA-A24, FLJ14668, Cardiolipin, NNAT, SELS, HIGD2A, SSR3 and NRP2. In some embodiments, the tumor cells are autologous cells. In some the embodiments, the tumor cells are allogeneic cells.

In some embodiments of the compositions and methods provided herein, the cytokine expressed by the cytokine-expressing population of genetically modified cells is selected from the group consisting of interferon alpha (IFN-a), interferon beta (IFN-), interferon gamma (IFN-y), interleukin-1 (IL-1), IL-2, IL-3, IL-4, IL-5, IL-6, IL-7, IL-8, IL-9, IL-10, IL-11, IL-12, tumor necrosis factor alpha (TNF-a), tumor necrosis factor beta (TNF-), erythropoietin (EPO), MIP3A, intracellular adhesion molecule (ICAM), macrophage colony stimulating factor (M-CSF), granulocyte colony stimulating factor (GCSF), and granulocyte-macrophage colony stimulating factor (GM-CSF). In particular embodiments, the cytokine is GM-CSF.

In some embodiments, the composition comprising one or more populations of cells genetically modified to express the coding sequence for a cytokine and the coding sequence of one, two, three, four, five, six, seven or eight prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a cytokine and the coding sequence of one prostate tumor-associated antigen selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a C)lokine and the coding sequence of two prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a c)lokine and the coding sequence of three prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a c)lokine and the coding sequence of four prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a c)lokine and the coding sequence of five prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a cytokine and the coding sequence of six prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a c)lokine and the coding sequence of seven prostate tumor-associated antigens selected from the group consisting of HLA-A24, FLJ14668, Cardiolipin, NNAT, SELS, HIGD2A, SSR3 and NRP2. In some embodiments, the composition comprises one or more populations of cells genetically modified to express the coding sequence for a c)lokine and the coding sequence of eight prostate tumor-associated antigens selected from the group consisting of HLA-A24, FLJ14668, Cardiolipin, NNAT, SELS, HIGD2A, SSR3 and NRP2.

In some embodiments, the composition comprises one or more populations of cells genetically modified to express the coding sequence for a c)lokine and the coding sequence of HLA-A24. In some embodiments, the composition comprises one or more populations of cells genetically modified to express the coding sequence for a cytokine and the coding sequence of FLJ14668. In some embodiments, the composition comprises one or more populations of cells genetically modified to express the coding sequence for a cytokine and the coding sequence of Cardiolipin. In some embodiments, the composition comprises one or more populations of cells genetically modified to express the coding sequence for a C)lokine and the coding sequence of NNAT. In some embodiments, the composition comprises one or more populations of cells genetically modified to express the coding sequence for a cytokine and the coding sequence of SELS. In some embodiments, the composition comprises one or more populations of cells genetically modified to express the coding sequence for a cytokine and the coding sequence of HIGD2A. In some embodiments, the composition comprises one or more populations of cells genetically modified to express the coding sequence for a cytokine and the coding sequence of SSR3. In some embodiments, the composition comprises one or more populations of cells genetically modified to express the coding sequence for a cytokine and the coding sequence of NRP2.

In some embodiments, the composition comprises one or more populations of cells genetically modified to express the coding sequence for a cytokine and the coding sequence of HLA-A24 and FLJ14668. In some embodiments, the composition comprises one or more populations of cells genetically modified to express the coding sequence for a cytokine and the coding sequence of HLA-A24 and Cardiolipin. In some embodiments, the composition comprises one or more populations of cells genetically modified to express the coding sequence for a cytokine and the coding sequence of HLA-A24 and NNAT. In some embodiments, the composition comprises one or more populations of cells genetically modified to express the coding sequence for a cytokine and the coding sequence of HLA-A24 and SELS. In some embodiments, the composition comprises one or more populations of cells genetically modified to express the coding sequence for a cytokine and the coding sequence of HLA-A24 and HIGD2A. In some embodiments, the composition comprises one or more populations of cells genetically modified to express the coding sequence for a cytokine and the coding sequence of HLA-A24 and SSR3. In some embodiments, the composition comprises one or more populations of cells genetically modified to express the coding sequence for a cytokine and the coding sequence of HLA-A24 and NRP2. In some embodiments, the composition comprises one or more populations of cells genetically modified to express the coding sequence for a cytokine and the coding sequence of FLJ14668 and Cardiolipin. In some embodiments, the composition comprises one or more populations of cells genetically modified to express the coding sequence for a cytokine and the coding sequence of FLJ14668 and NNAT. In some embodiments, the composition comprises one or more populations of cells genetically modified to express the coding sequence for a cytokine and the coding sequence of FLJ14668 and SELS. In some embodiments, the composition comprises one or more populations of cells genetically modified to express the coding sequence for a cytokine and the coding sequence of FLJ14668 and HIGD2A. In some embodiments, the composition comprises one or more populations of cells genetically modified to express the coding sequence for a cytokine and the coding sequence of FLJ14668 and SSR3. In some embodiments, the composition comprises one or more populations of cells genetically modified to express the coding sequence for a cytokine and the coding sequence of FLJ14668 and NRP2. In some embodiments, the composition comprises one or more populations of cells genetically modified to express the coding sequence for a cytokine and the coding sequence of Cardiolipin and NNAT. In some embodiments, the composition comprises one or more populations of cells genetically modified to express the coding sequence for a cytokine and the coding sequence of Cardiolipin and SELS. In some embodiments, the composition comprises one or more populations of cells genetically modified to express the coding sequence for a cytokine and the coding sequence of Cardiolipin and HIGD2A. In some embodiments, the composition comprises one or more populations of cells genetically modified to express the coding sequence for a cytokine and the coding sequence of Cardiolipin and SSR3. In some embodiments, the composition comprises one or more populations of cells genetically modified to express the coding sequence for a cytokine and the coding sequence of Cardiolipin and NRP2. In some embodiments, the composition comprises one or more populations of cells genetically modified to express the coding sequence for a cytokine and the coding sequence of NNAT and SELS. In some embodiments, the composition comprises one or more populations of cells genetically modified to express the coding sequence for a cytokine and the coding sequence of NNAT and HIGD2A. In some embodiments, the composition comprises one or more populations of cells genetically modified to express the coding sequence for a cytokine and the coding sequence of NNAT and SSR3. In some embodiments, the composition comprises one or more populations of cells genetically modified to express the coding sequence for a cytokine and the coding sequence of NNAT and NRP2. In some embodiments, the composition comprises one or more populations of cells genetically modified to express the coding sequence for a cytokine and the coding sequence of SELS and HIGD2A. In some embodiments, the composition comprises one or more populations of cells genetically modified to express the coding sequence for a cytokine and the coding sequence of SELS and SSR3. In some embodiments, the composition comprises one or more populations of cells genetically modified to express the coding sequence for a cytokine and the coding sequence of SELS and NRP2. In some embodiments, the composition comprises one or more populations of cells genetically modified to express the coding sequence for a cytokine and the coding sequence of HIGD2A and SSR3. In some embodiments, the composition comprises one or more populations of cells genetically modified to express the coding sequence for a cytokine and the coding sequence of HIGD2A and NRP2. In some embodiments, the composition comprises one or more populations of cells genetically modified to express the coding sequence for a cytokine and the coding sequence of SSR3 and NRP2.

In some embodiments, the composition comprises one or more populations of cells genetically modified to express the coding sequence for a cytokine and the coding sequence of HLA-A24 FLJ14668 and Cardiolipin. In some embodiments, the composition comprises one or more populations of cells genetically modified to express the coding sequence for a cytokine and the coding sequence of HLA-A24, FLJ14668 and NNAT. In some embodiments, the composition comprises one or more populations of cells genetically modified to express the coding sequence for a cytokine and the coding sequence of HLA-A24, FLJ14668 and SELS. In some embodiments, the composition comprises one or more populations of cells genetically modified to express the coding sequence for a cytokine and the coding sequence of HLA-A24, FLJ14668 and HIGD2A. In some embodiments, the composition comprises one or more populations of cells genetically modified to express the coding sequence for a cytokine and the coding sequence of HLA-A24, FLJ14668 and SSR3. In some embodiments, the composition comprises one or more populations of cells genetically modified to express the coding sequence for a cytokine and the coding sequence of HLA-A24, FLJ14668 and NRP2. In some embodiments, the composition comprises one or more populations of cells genetically modified to express the coding sequence for a cytokine and the coding sequence of HLA-A24. Cardiolipin and NNAT. In some embodiments, the composition comprises one or more populations of cells genetically modified to express the coding sequence for a cytokine and the coding sequence of HLA-A24, Cardiolipin and SELS. In some embodiments, the composition comprises one or more populations of cells genetically modified to express the coding sequence for a cytokine and the coding sequence of HLA-A24, Cardiolipin and HIGD2A, In some embodiments, the composition comprises one or more populations of cells genetically modified to express the coding sequence for a cytokine and the coding sequence of HLA-A24, Cardiolipin and SSR3. In some embodiments, the composition comprises one or more populations of cells genetically modified to express the coding sequence for a cytokine and the coding sequence of HLA-A24, Cardiolipin and NRP2. In some embodiments, the composition comprises one or more populations of cells genetically modified to express the coding sequence for a cytokine and the coding sequence of HLA-A24, NNAT and SELS. In some embodiments, the composition comprises one or more populations of cells genetically modified to express the coding sequence for a cytokine and the coding sequence of HLA-A24, NNAT and HIGD2A. In some embodiments, the composition comprises one or more populations of cells genetically modified to express the coding sequence for a cytokine and the coding sequence of HLA-A24, NNAT and SSR3. In some embodiments, the composition comprises one or snore populations of cells genetically modified to express the coding sequence for a cytokine and the coding sequence of HLA-A24, NNAT and NRP2. In some embodiments, the composition comprises one or more populations of cells genetically modified to express the coding sequence for a cytokine and the coding sequence of HLA-A24, SELS and HIGD2A. In some embodiments, the composition comprises one or more populations of cells genetically modified to express the coding sequence for a cytokine and the coding sequence of HLA-A24, SELS and SSR3. In some embodiments, the composition comprises one or more populations of cells genetically modified to express the coding sequence for a cytokine and the coding sequence of HLA-A24, SELS and NRP2. In some embodiments, the composition comprises one or more populations of cells genetically modified to express the coding sequence for a cytokine and the coding sequence of HLA-A24, HIGD2A and SSR3. In some embodiments, the composition comprises one or more populations of cells genetically modified to express the coding sequence for a cytokine and the coding sequence of HLA-A24, HIGD2A and NRP2. In some embodiments, the composition comprises one or more populations of cells genetically modified to express the coding sequence for a cytokine and the coding sequence of HLA-A24, SSR3 and NRP2.

In some embodiments, the composition comprises one or more populations of cells genetically modified to express the coding sequence for a cytokine and the coding sequence of FLJ14668, Cardiolipin and NNAT. In some embodiments, the composition comprises one or more populations of cells genetically modified to express the coding sequence for a cytokine and the coding sequence of FLJ14668, Cardiolipin and SELS. In some embodiments, the composition comprises one or more populations of cells genetically modified to express the coding sequence for a cytokine and the coding sequence of FLJ14668, Cardiolipin and HIGD2A. In some embodiments, the composition comprises one or more populations of cells genetically modified to express the coding sequence for a cytokine and the coding sequence of FLJ14668, Cardiolipin and SSR3. In some embodiments, the composition comprises one or more populations of cells genetically modified to express the coding sequence for a cytokine and the coding sequence of FLJ14668, Cardiolipin and NRP2. In some embodiments, the composition comprises one or more populations of cells genetically modified to express the coding sequence for a cytokine and the coding sequence of FLJ14668, NNAT and SELS. In some embodiments, the composition comprises one or more populations of cells genetically modified to express the coding sequence for a cytokine and the coding sequence of FLJ14668, NNAT and HIGD2A. In some embodiments, the composition comprises one or more populations of cells genetically modified to express the coding sequence for a cytokine and the coding sequence of FLJ14668, NNAT and SSR3. In some embodiments, the composition comprises one or more populations of cells genetically modified to express the coding sequence for a cytokine and the coding sequence of FLJ14668, NNAT and NRP2. In some embodiments, the composition comprises one or more populations of cells genetically modified to express the coding sequence for a cytokine and the coding sequence of FLJ14668, SELS and HIGD2A. In some embodiments, the composition comprises one or more populations of cells genetically modified to express the coding sequence for a cytokine and the coding sequence of FLJ14668, SELS and SSR3. In some embodiments, the composition comprises one or more populations of cells genetically modified to express the coding sequence for a cytokine and the coding sequence of FLJ14668, SELS and NRP2. In some embodiments, the composition comprises one or more populations of cells genetically modified to express the coding sequence for a cytokine and the coding sequence of FLJ14668, HIGD2A and SSR3. In some embodiments, the composition comprises one or more populations of cells genetically modified to express the coding sequence for a cytokine and the coding sequence of FLJ14668, HIGD2A and NRP2. In some embodiments, the composition comprises one or more populations of cells genetically modified to express the coding sequence for a cytokine and the coding sequence of FLJ14668, SSR3 and NRP2.

In some embodiments, the composition comprises one or more populations of cells genetically modified to express the coding sequence for a cytokine and the coding sequence of Cardiolipin, NNAT and SELS. In some embodiments, the composition comprises one or more populations of cells genetically modified to express the coding sequence for a cytokine and the coding sequence of Cardiolipin, NNAT and HIGD2A. In some embodiments, the composition comprises one or more populations of cells genetically modified to express the coding sequence for a cytokine and the coding sequence of Cardiolipin, NNAT and SSR3. In some embodiments, the composition comprises one or more populations of cells genetically modified to express the coding sequence for a cytokine and the coding sequence of Cardiolipin, NNAT and NRP2. In some embodiments, the composition comprises one or more populations of cells genetically modified to express the coding sequence for a cytokine and the coding sequence of Cardiolipin, SELS and HIGD2A. In some embodiments, the composition comprises one or more populations of cells genetically modified to express the coding sequence for a cytokine and the coding sequence of Cardiolipin, SELS and SSR3. In some embodiments, the composition comprises one or more populations of cells genetically modified to express the coding sequence for a cytokine and the coding sequence of Cardiolipin, SELS and NRP2. In some embodiments, the composition comprises one or more populations of cells genetically modified to express the coding sequence for a cytokine and the coding sequence of Cardiolipin. HIGD2A and SSR3. In some embodiments, the composition comprises one or more populations of cells genetically modified to express the coding sequence for a cytokine and the coding sequence of Cardiolipin, HIGD2A and NRP2. In some embodiments, the composition comprises one or more populations of cells genetically modified to express the coding sequence for a cytokine and the coding sequence of Cardiolipin, SSR3 and NRP2.

In some embodiments, the composition comprises one or more populations of cells genetically modified to express the coding sequence for a cytokine and the coding sequence of NNAT, SELS and HIGD2A. In some embodiments, the composition comprises one or more populations of cells genetically modified to express the coding sequence for a cytokine and the coding sequence of NNAT, SELS and SSR3. In some embodiments, the composition comprises one or more populations of cells genetically modified to express the coding sequence for a cytokine and the coding sequence of NNAT, SELS and NRP2. In some embodiments, the composition comprises one or more populations of cells genetically modified to express the coding sequence for a cytokine and the coding sequence of NNAT, HIGD2A and SSR3. In some embodiments, the composition comprises one or more populations of cells genetically modified to express the coding sequence for a cytokine and the coding sequence of NNAT, HIGD2A and NRP2. In some embodiments, the composition comprises one or more populations of cells genetically modified to express the coding sequence for a cytokine and the coding sequence of NNAT, SSR3 and NRP2.

In some embodiments, the composition comprises one or more populations of cells genetically modified to express the coding sequence for a cytokine and the coding sequence of SELS, HIGD2A and SSR3. In some embodiments, the composition comprises one or more populations of cells genetically modified to express the coding sequence for a cytokine and the coding sequence of SELS, HIGD2A and NRP2. In some embodiments, the composition comprises one or more populations of cells genetically modified to express the coding sequence for a cytokine and the coding sequence of SELS, SSR3 and NRP2.

In some embodiments, the composition comprises one or more populations of cells genetically modified to express the coding sequence for a cytokine and the coding sequence of HIGD2A, SSR3 and NRP2.

In some embodiments, the composition comprises one or more populations of cells genetically modified to express the coding sequence for a cytokine and the coding sequence of HLA-A24, FLJ14668, Cardiolipin and NNAT. In some embodiments, the composition comprises one or more populations of cells genetically modified to express the coding sequence for a cytokine and the coding sequence of HLA-A24, FLJ14668, Cardiolipin and SELS. In some embodiments, the composition comprises one or more populations of cells genetically modified to express the coding sequence for a cytokine and the coding sequence of HLA-A24, FLJ14668, Cardiolipin and HIGD2A. In some embodiments, the composition comprises one or more populations of cells genetically modified to express the coding sequence for a cytokine and the coding sequence of HLA-A24, FLJ14668, Cardiolipin and SSR3. In some embodiments, the composition comprises one or more populations of cells genetically modified to express the coding sequence for a cytokine and the coding sequence of HLA-A24, FLJ14668, Cardiolipin and NRP2.

In some embodiments, the composition comprises one or more populations of cells genetically modified to express the coding sequence for a cytokine and the coding sequence of HLA-A24. Cardiolipin, NNAT and SELS. In some embodiments, the composition comprises one or more populations of cells genetically modified to express the coding sequence for a cytokine and the coding sequence of HLA-A24. Cardiolipin, NNAT and HIGD2A. In some embodiments, the composition comprises one or more populations of cells genetically modified to express the coding sequence for a cytokine and the coding sequence of HLA-A24, Cardiolipin, NNAT and SSR3. In some embodiments, the composition comprises one or more populations of cells genetically modified to express the coding sequence for a cytokine and the coding sequence of HLA-A24, Cardiolipin, NNAT and NRP2.

In some embodiments, the composition comprises one or more populations of cells genetically modified to express the coding sequence for a cytokine and the coding sequence of HLA-A24, NNAT, SELS and HIGD2A. In some embodiments, the composition comprises one or more populations of cells genetically modified to express the coding sequence for a cytokine and the coding sequence of HLA-A24, NNAT, SELS and SSR3. In some embodiments, the composition comprises one or more populations of cells genetically modified to express the coding sequence for a cytokine and the coding sequence of HLA-A24, NNAT, SELS and NRP2.

In some embodiments, the composition comprises one or more populations of cells genetically modified to express the coding sequence for a cytokine and the coding sequence of HLA-A24, SELS, HIGD2A and SSR3. In some embodiments, the composition comprises one or more populations of cells genetically modified to express the coding sequence for a cytokine and the coding sequence of HLA-A24, SELS, HIGD2A and NRP2.

In some embodiments, the composition comprises one or more populations of cells genetically modified to express the coding sequence for a cytokine and the coding sequence of HLA-A24, HIGD2A, SSR3 and NRP2.

In some embodiments, the composition comprises one or more populations of cells genetically modified to express the coding sequence for a cytokine and the coding sequence of FLJ14668, Cardiolipin, NNAT and SELS. In some embodiments, the composition comprises one or more populations of cells genetically modified to express the coding sequence for a cytokine and the coding sequence of FLJ14668, Cardiolipin, NNAT and HIGD2A. In some embodiments, the composition comprises one or more populations of cells genetically modified to express the coding sequence for a cytokine and the coding sequence of FLJ14668, Cardiolipin, NNAT and SSR3. In some embodiments, the composition comprises one or more populations of cells genetically modified to express the coding sequence for a cytokine and the coding sequence of FLJ14668, Cardiolipin, NNAT and NRP2.

In some embodiments, the composition comprises one or more populations of cells genetically modified to express the coding sequence for a cytokine and the coding sequence of Cardiolipin, NNAT, SELS and HIGD2A. In some embodiments, the composition comprises one or more populations of cells genetically modified to express the coding sequence for a cytokine and the coding sequence of Cardiolipin, NNAT, SELS and SSR3. In some embodiments, the composition comprises one or more populations of cells genetically modified to express the coding sequence for a cytokine and the coding sequence of Cardiolipin, NNAT, SELS and NRP2.

In some embodiments, the composition comprises one or more populations of cells genetically modified to express the coding sequence for a cytokine and the coding sequence of NNAT, SELS, HIGD2A and SSR3. In some embodiments, the composition comprises one or more populations of cells genetically modified to express the coding sequence for a cytokine and the coding sequence of NNAT, SELS, HIGD2A and NRP2.

In some embodiments, the composition comprises one or more populations of cells genetically modified to express the coding sequence for a cytokine and the coding sequence of SELS, HIGD2A, SSR3 and NRP2.

In some embodiments, the composition comprises one or more populations of cells genetically modified to express the coding sequence for a cytokine and the coding sequence of HLA-A24, FLJ14668, Cardiolipin, NNAT and SELS. In some embodiments, the composition comprises one or more populations of cells genetically modified to express the coding sequence for a cytokine and the coding sequence of HLA-A24, FLJ14668, Cardiolipin, NNAT and HIGD2A. In some embodiments, the composition comprises one or more populations of cells genetically modified to express the coding sequence for a cytokine and the coding sequence of HLA-A24, FLJ14668, Cardiolipin, NNAT and SSR3. In some embodiments, the composition comprises one or more populations of cells genetically modified to express the coding sequence for a cytokine and the coding sequence of HLA-A24, FLJ14668, Cardiolipin, NNAT and NRP2.

In some embodiments, the composition comprises one or more populations of cells genetically modified to express the coding sequence for a cytokine and the coding sequence of FLJ14668, Cardiolipin, NNAT, SELS and HIGD2A. In some embodiments, the composition comprises one or more populations of cells genetically modified to express the coding sequence for a cytokine and the coding sequence of FLJ14668, Cardiolipin, NNAT, SELS and SSR3. In some embodiments, the composition comprises one or more populations of cells genetically modified to express the coding sequence for a cytokine and the coding sequence of FLJ14668, Cardiolipin, NNAT, SELS and NRP2.

In some embodiments, the composition comprises one or more populations of cells genetically modified to express the coding sequence for a cytokine and the coding sequence of Cardiolipin, NNAT, SELS, HIGD2A and SSR3. In some embodiments, the composition comprises one or more populations of cells genetically modified to express the coding sequence for a cytokine and the coding sequence of Cardiolipin, NNAT, SELS, HIGD2A and NRP2.

In some embodiments, the composition comprises one or more populations of cells genetically modified to express the coding sequence for a cytokine and the coding sequence of NNAT, SELS, HIGD2A, SSR3 and NRP2.

In some embodiments, the composition comprises one or more populations of cells genetically modified to express the coding sequence for a cytokine and the coding sequence of HLA-A24, FLJ14668, Cardiolipin, NNAT, SELS and HIGD2A. In some embodiments, the composition comprises one or more populations of cells genetically modified to express the coding sequence for a cytokine and the coding sequence of HLA-A24, FLJ14668, Cardiolipin, NNAT, SELS and SSR3. In some embodiments, the composition comprises one or more populations of cells genetically modified to express the coding sequence for a cytokine and the coding sequence of HLA-A24, FLJ14668, Cardiolipin, NNAT, SELS and NRP2.

In some embodiments, the composition comprises one or more populations of cells genetically modified to express the coding sequence for a cytokine and the coding sequence of FLJ14668, Cardiolipin, NNAT, SELS, HIGD2A and SSR3. In some embodiments, the composition comprises one or more populations of cells genetically modified to express the coding sequence for a cytokine and the coding sequence of FLJ14668, Cardiolipin, NNAT, SELS, HIGD2A and NRP2.

In some embodiments, the composition comprises one or more populations of cells genetically modified to express the coding sequence for a cytokine and the coding sequence of Cardiolipin, NNAT, SELS, HIGD2A, SSR3 and NRP2.

In some embodiments, the composition comprises one or more populations of cells genetically modified to express the coding sequence for a cytokine and the coding sequence of HLA-A24, FLJ14668, Cardiolipin, NNAT, SELS, HIGD2A and SSR3. In some embodiments, the composition comprises one or more populations of cells genetically modified to express the coding sequence for a cytokine and the coding sequence of HLA-A24, FLJ14668, Cardiolipin, NNAT, SELS, HIGD2A and NRP2.

In some embodiments, the composition comprises one or more populations of cells genetically modified to express the coding sequence for a cytokine and the coding sequence of FLJ14668, Cardiolipin, NNAT, SELS, HIGD2A, SSR3 and NRP2.

In some embodiments, the composition comprises one or more populations of cells genetically modified to express the coding sequence for a cytokine and the coding sequence of HLA-A24, FLJ14668, Cardiolipin, NNAT, SELS, HIGD2A and SSR3.

In some embodiments, the composition comprises one or more populations of cells genetically modified to express the coding sequence for a cytokine and the coding sequence of HLA-A24, FLJ14668, Cardiolipin, NNAT, SELS, HIGD2A, SSR3 and NRP2.

In some embodiments of the compositions and methods provided herein, the composition further comprises a tyrosine kinase inhibitor selected from the group consisting of gefitimib, erolotinib and imatinib.

In some embodiments of the compositions and methods provided herein, the composition further comprises an additional cancer therapeutic agent. In some embodiments, the additional cancer therapeutic agent is an anti-CTLA4 antibody. In some embodiments, the one or more populations off cells of the cellular immunotherapy composition are further genetically modified to express an anti-CTLA-4 antibody. In some embodiments, the additional cancer therapeutic agent is an anti-PD-1 antibody. In some embodiments, the one or more populations of cells of the cellular immunotherapy composition are further genetically modified to express an anti-PD-1 antibody.

The invention further provides kits comprising one or more populations of cells genetically modified to express the coding sequence for a cytokine and the coding sequence of one or more prostate tumor-associated antigens selected from the group consisting of HLA-A24, FLJ14668, Cardiolipin, Neuronatin (NNAT). Selenoprotein (SELS), HIG1 domain family, member 2A (HIGD2A), Signal sequence receptor, gamma (SSR3) and Neuropilin 2 (NRP2), for use according to the description provided herein.

The invention further provides methods of making a composition comprising one or more populations of cells genetically modified to express the coding sequence for a cytokine and the coding sequence of one or more prostate tumor-associated antigens selected from the group consisting of HLA-A24, FLU 14668, Cardiolipin, NNAT, SELS, HIGD2A, SSR3 and NRP2. The methods comprise obtaining one or more population of cells and modifying the one or more population of cells by introducing into the cells: (i) a nucleic acid molecule comprising a nucleic acid sequence encoding a cytokine operably linked to a promoter: (ii) one or more nucleic acid molecules comprising a nucleic acid sequence encoding a prostate tumor-associated antigen selected from the group consisting of HLA-A24, FLJ14668, Cardiolipin, NNAT, SELS, HIGD2A, SSR3 and NRP2; and (iii) a nucleic acid molecule comprising a nucleic acid sequence encoding a selectable marker operably linked to a promoter.

4. BRIEF DESCRIPTION OF THE FIGURES

FIG. 1 presents the expression patterns of PNPO with increasing prostate cancer disease grade derived from the Oncomine database. In FIG. 1, Class 1: Normal prostate (n=41), Class 2: Prostate cancer (n=62) Class 3: Lymph node metastasis (n=9), P-value: 1.25E-5, and Correlation=0.408.

Figure 2:
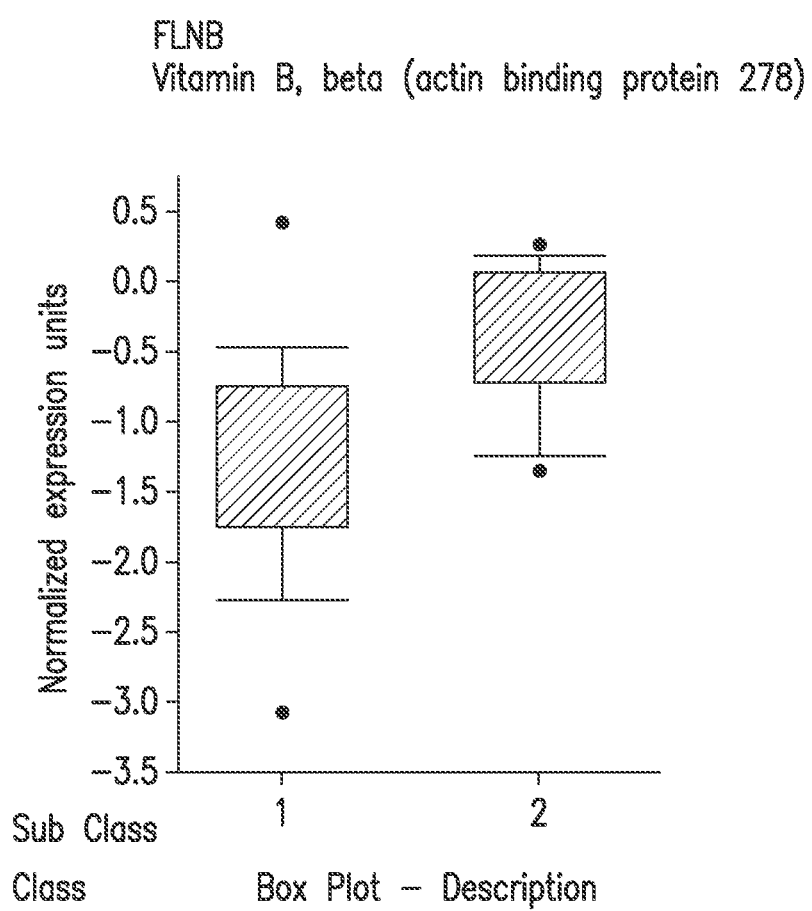

FIG. 2 presents the expression patterns of FLNB with increasing prostate cancer disease grade derived from the Oncomine database. In FIG. 2, Class 1: Prostate carcinoma (n=59), Class 2: Metastatic prostate cancer (n=20), and P-value: 4.6E-7.

FIG. 3A presents the trial design for the G-9803 Phase II GVAX immunotherapy clinical trial in chemotherapy-naive patients with hormone-refractory prostate cancer (n=55). The trial enrolled PSA-rising patients, who were treated with low-dose GVAX immunotherapy; as well as metastatic patients, who were treated with both low and high-dose GVAX immunotherapy.

FIG. 3B presents the trial design for the G-0010 Phase II GVAX immunotherapy clinical trial in chemotherapy-naive patients with hormone-refractory prostate cancer (HRPC) (n=80). The trial enrolled metastatic patients, who were treated with low, mid and high-dose GVAX immunotherapy.

Figure 4A:
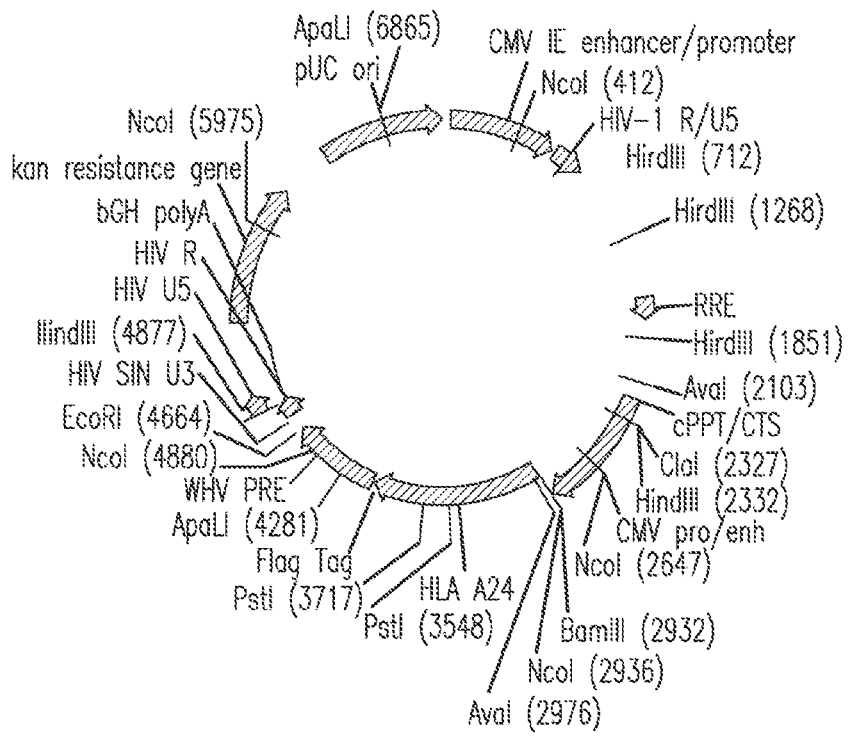

FIG. 4A presents a plasmid map of pKCCMVHLA-A2402Flag.

Figure 4B:
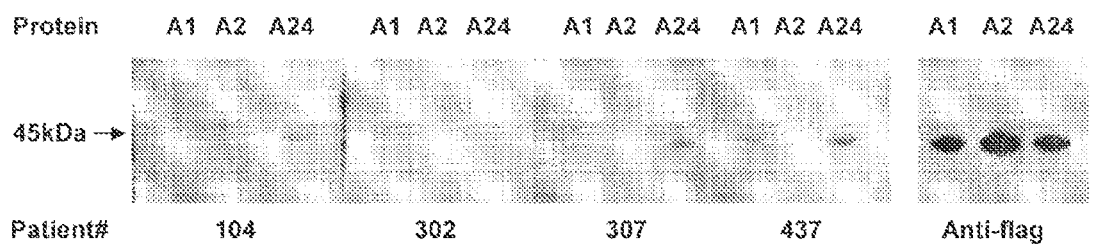

FIG. 4B presents representative blots of HLA-A24 probed with post-vaccination serum from immuno-positive G-0010 patients treated with GVAX immunotherapy for prostate cancer. Serum was diluted 1:500.

Figure 4C:
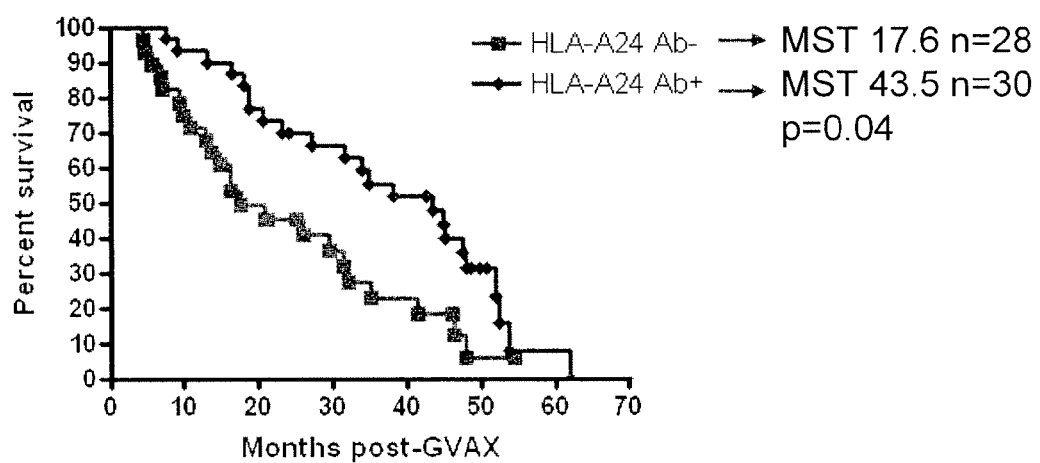

FIG. 4C presents a correlation of HLA-A24 Ab induction with survival in G-0010 patients following GVAX immunotherapy. MST=median survival time.

Figure 5A:
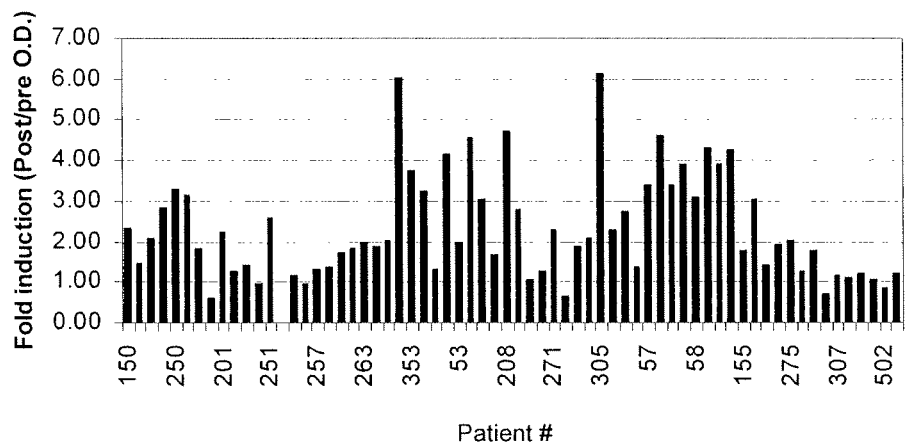

FIG. 5A presents the fold-induction of OUTB2 antibody titer in G-0010 patients following GVAX immunotherapy for prostate cancer.

Figure 5B:
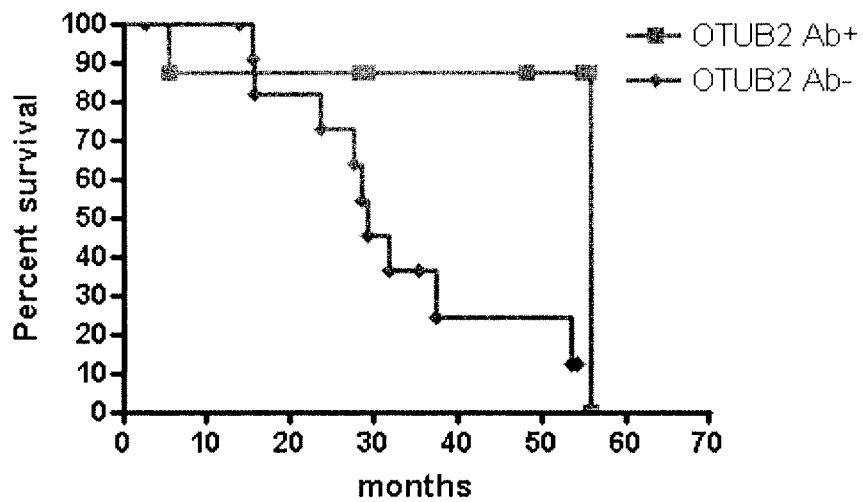

FIG. 5B presents a correlation of OUTB2 Ab induction with survival in G-9803 patients following GVAX immunotherapy. MST=median survival time.

Figure 6A:
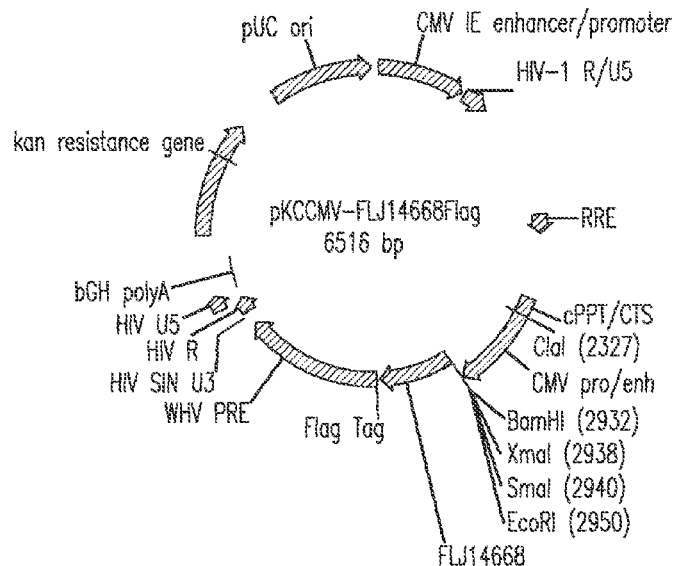

FIG. 6A presents a plasmid map of pKCCMVHLA-A2402Flag.

Figure 6B:
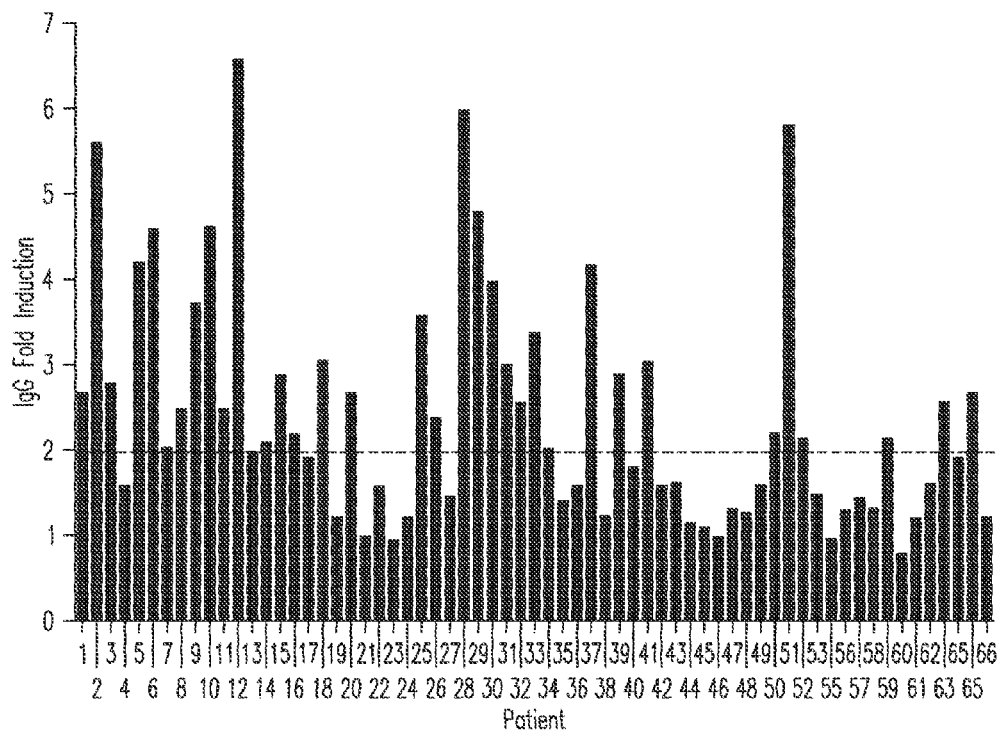

FIG. 6B presents the fold-induction of FLJ14668 antibody titer in G-0010 patients following GVAX immunotherapy for prostate cancer.

FIG. 6C presents the fold-induction of tetanus toxoid IgG/IgM antibodies in G-0010 patients.

FIG. 6D presents a correlation of FLJ14668 Ab induction with survival in G-0010 patients following GVAX immunotherapy. MST=median survival time.

Figure 6E:
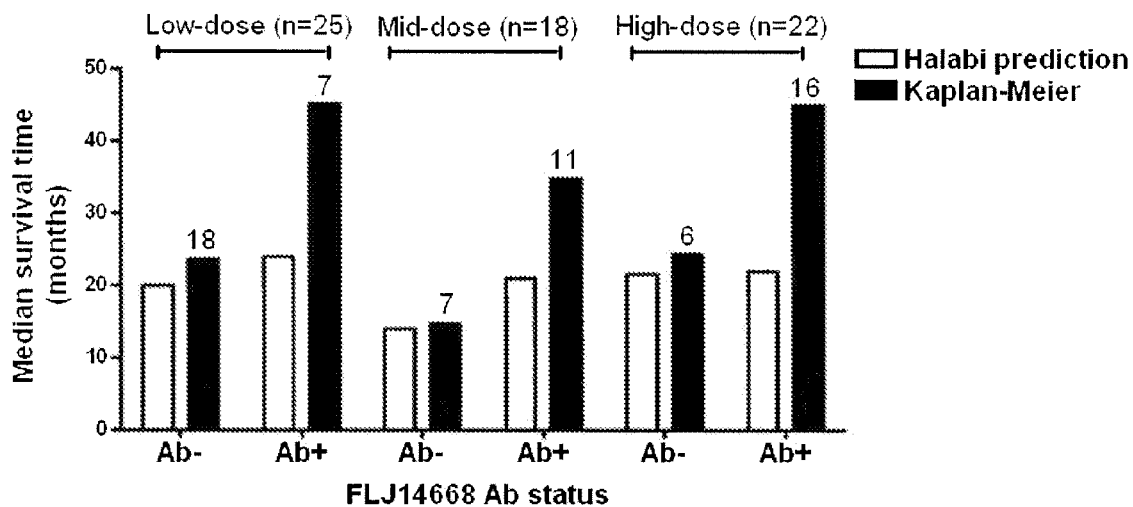

FIG. 6E presents a comparison of predicted and actual survival in FLJ14668 antibody positive and negative patient populations in G-0010.

Figure 6F:
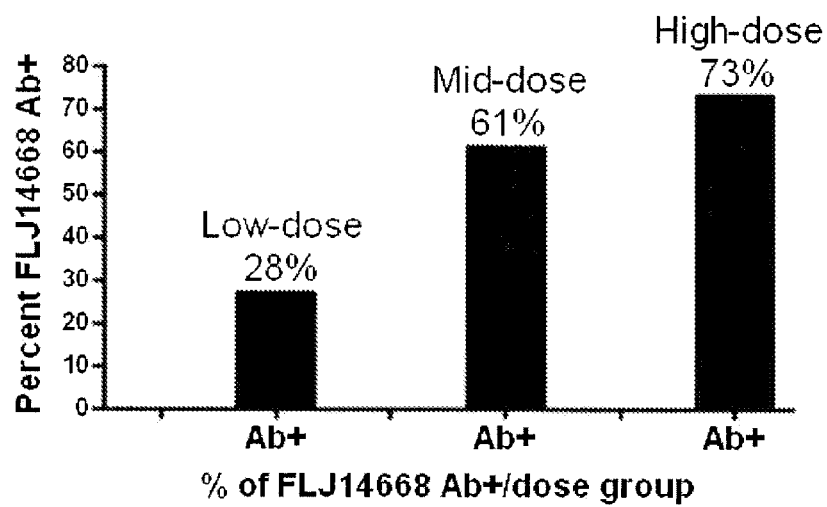

FIG. 6F presents G-0010 FLJ14668 antibody dose-response.

Figure 7A:
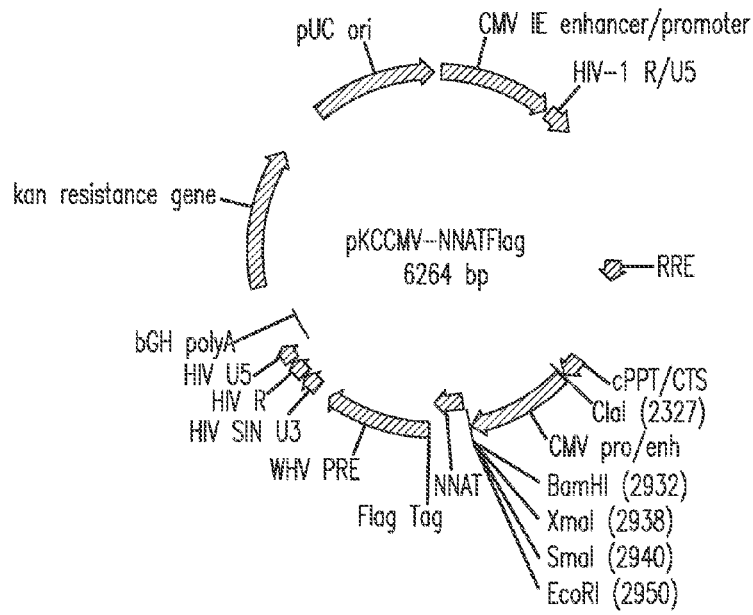

FIG. 7A presents plasmid map of pKCCMV-NNATFlag.

Figure 7B:
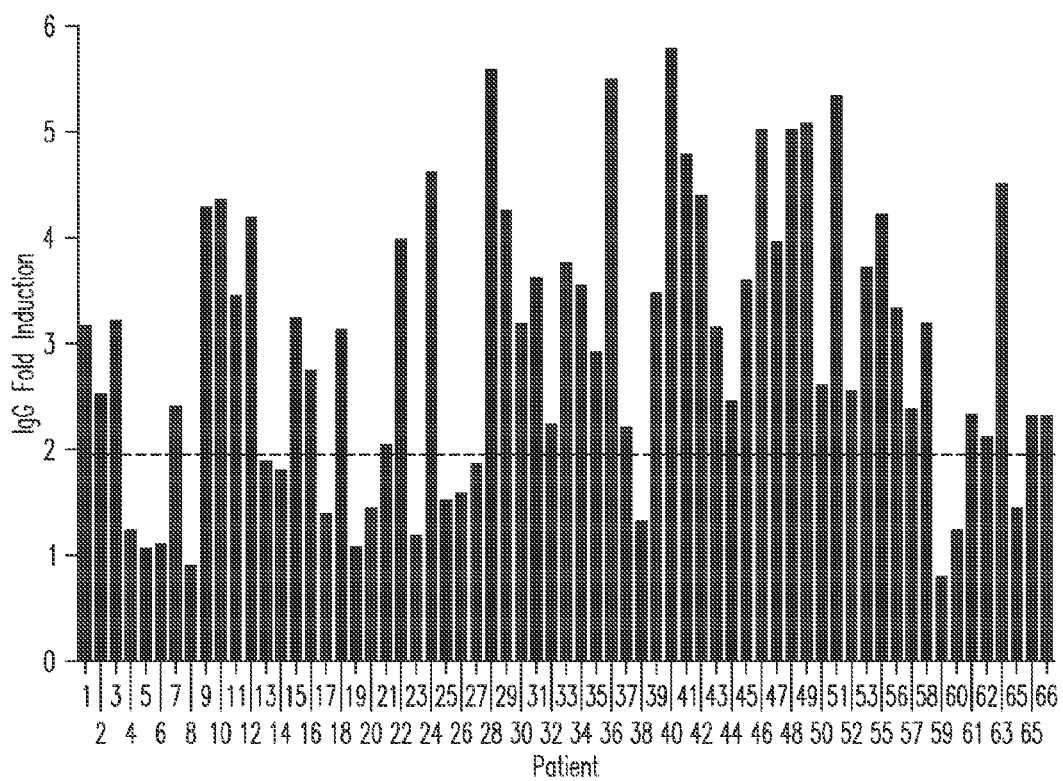

FIG. 7B presents the fold-induction of NNAT IgG/IgM antibodies in G-0010 patients.

Figure 7C:
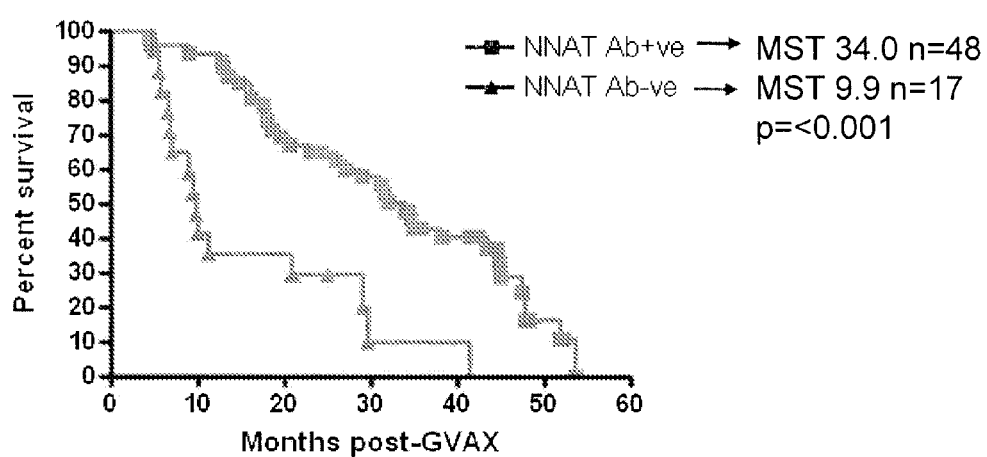

FIG. 7C presents the association of NNAT Ab immune response and survival in G-0010.

Figure 8A:
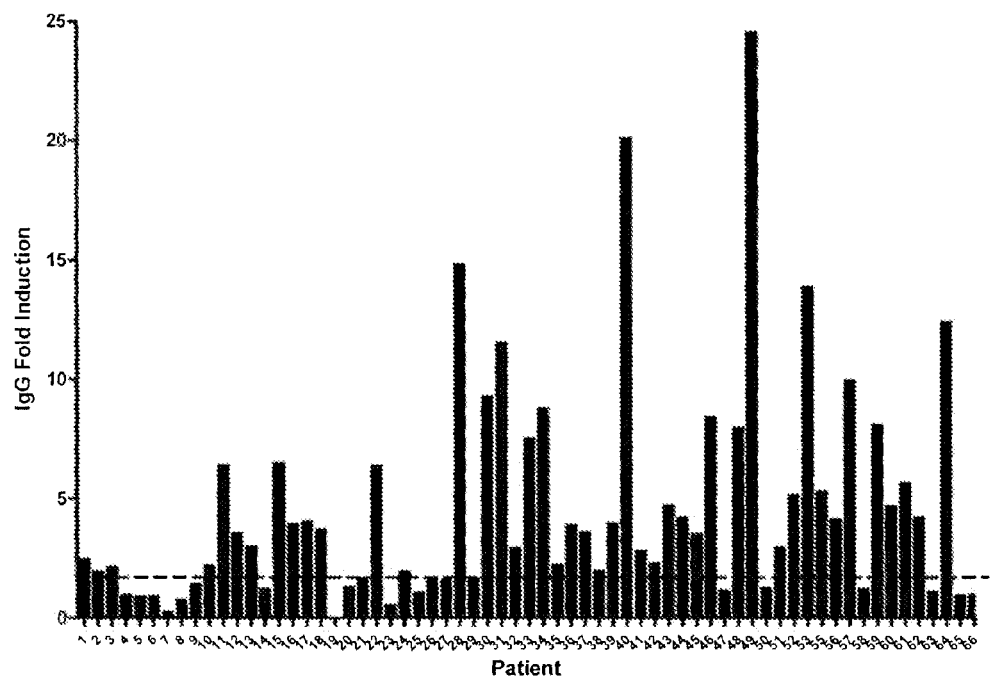

FIG. 8A presents the fold-induction of Cardiolipin IgG/IgM antibodies in G-OOI0 patients.

Figure 8B:
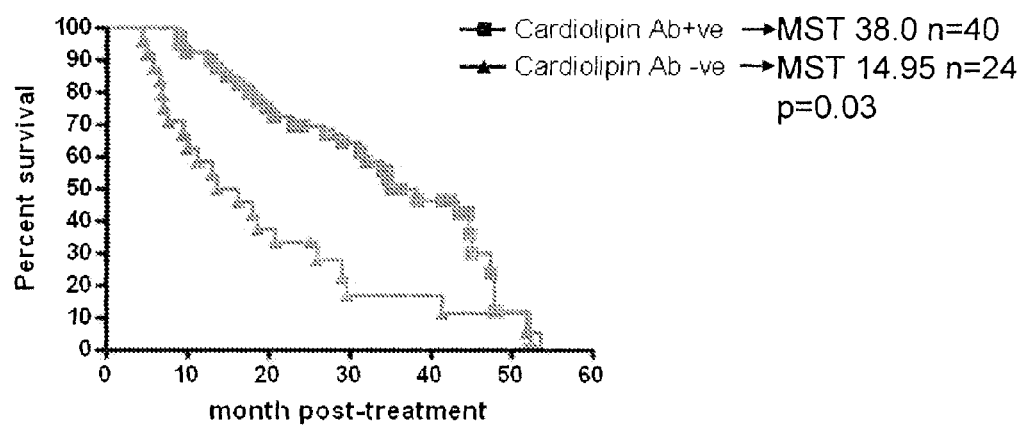

FIG. 8B presents the association of Cardiolipin Ab immune response and survival in G-0010.

Figure 9:
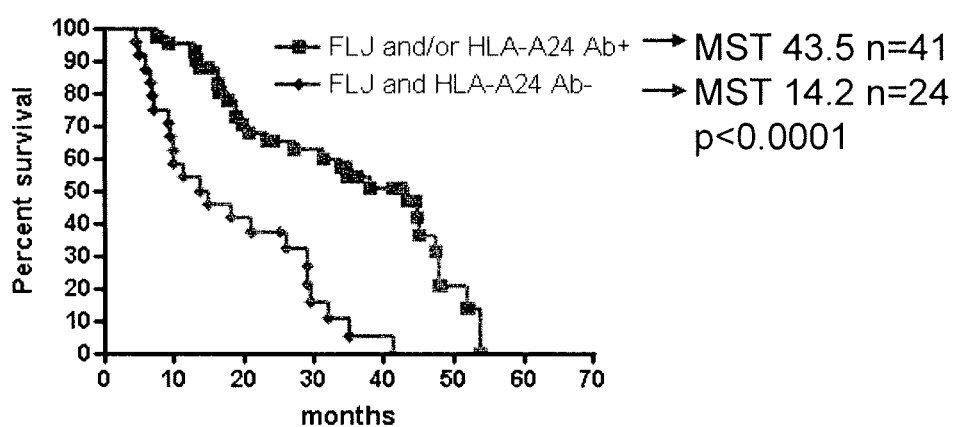

FIG. 9 presents the association of HLA-A24 and/or FLJ14668 immune response and survival in G-0010.

Figure 10:
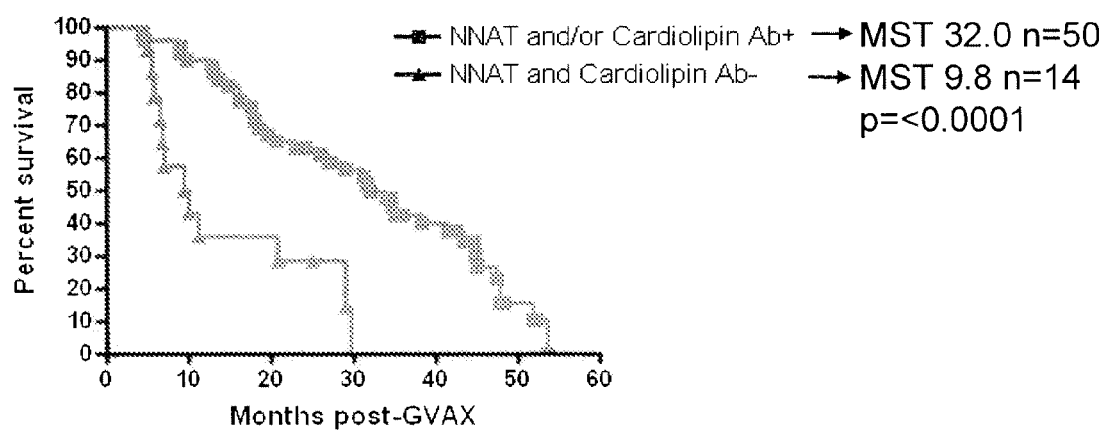

FIG. 10 presents the association of NNAT and/or Cardiolipin immune response and survival in G-0010

Figure 11:
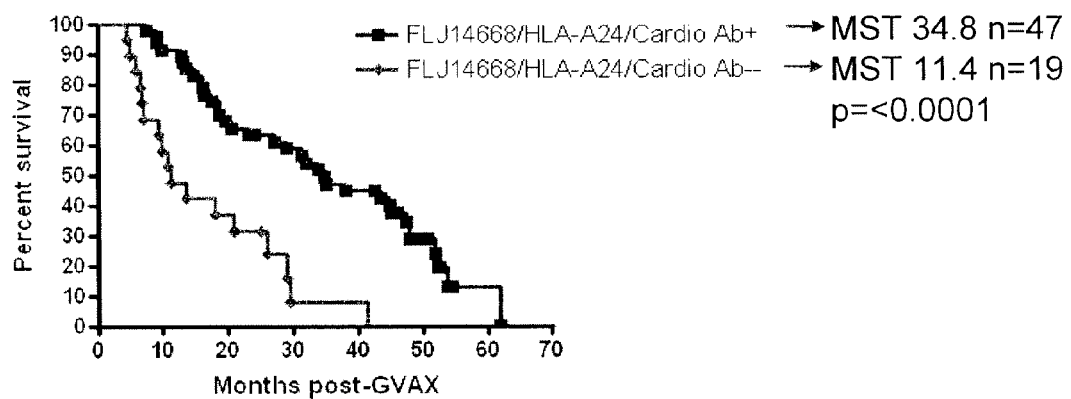

FIG. 11 presents the association of FLJ14668 and/or HLA-A24 and/or Cardiolipin immune response and survival in G-0010.

Figure 12A:
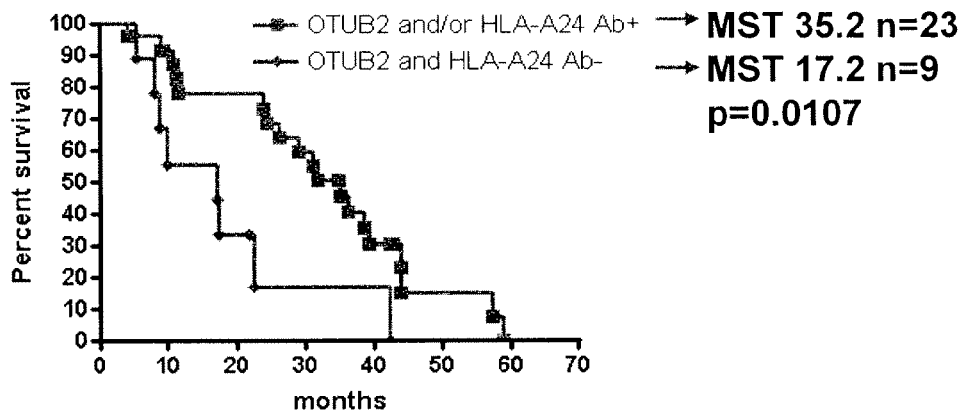

FIG. 12A presents a correlation of HLA-A24 and/or OUTB2 Ab induction with survival in G-9803 metastatic hormone refractory prostate cancer (HRPC) patients following GVAX immunotherapy. MST=median survival time.

Figure 12B:
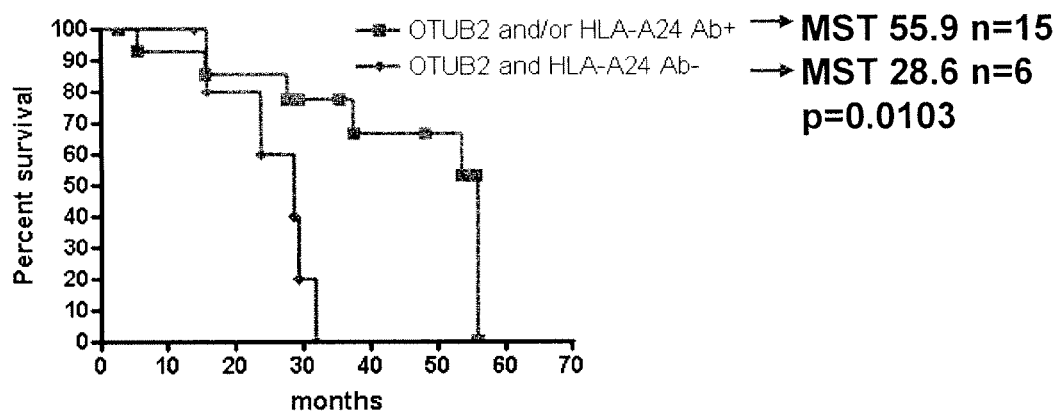

FIG. 12B presents a correlation of HLA-A24 and/or OUTB2 Ab induction with survival in G-9803 PSA-rising HPRC patients following GVAX immunotherapy. MST=median survival time.

Figure 12C:
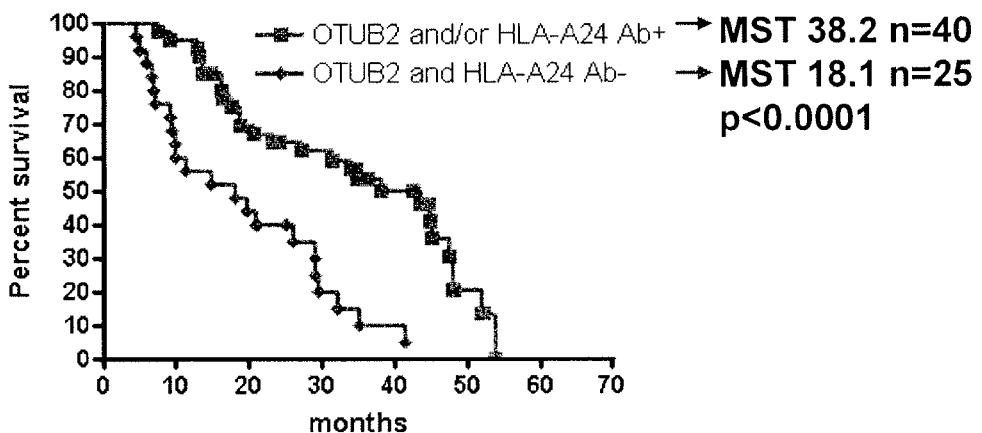

FIG. 12C presents a correlation of HLA-A24 and/or OUTB2 Ab induction with survival in G-0010 metastatic HPRC patients following GVAX immunotherapy. MST=median survival time.

Figure 13A:
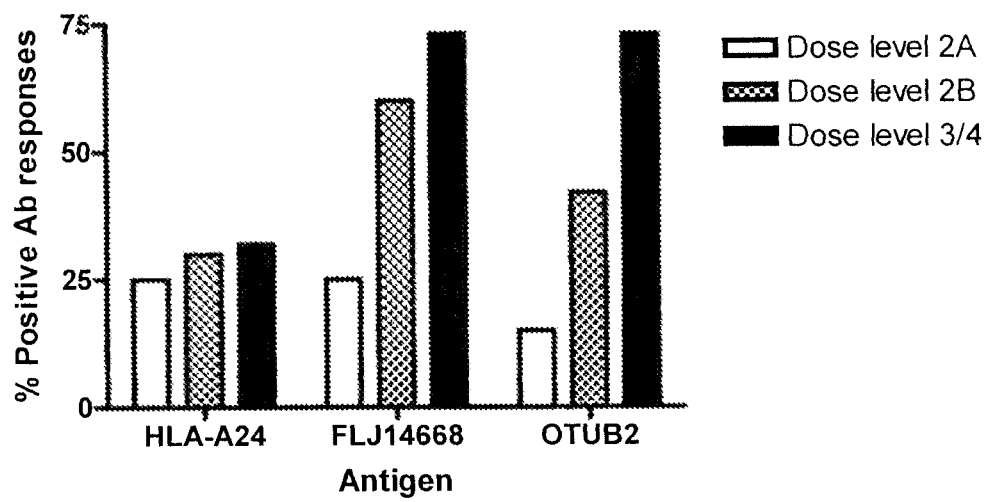

FIG. 13A presents the effect of GVAX immunotherapy dose level on HLA-A24, FLJ14668 and OUTB2 antibody induction in G-0010 patients.

Figure 13B:
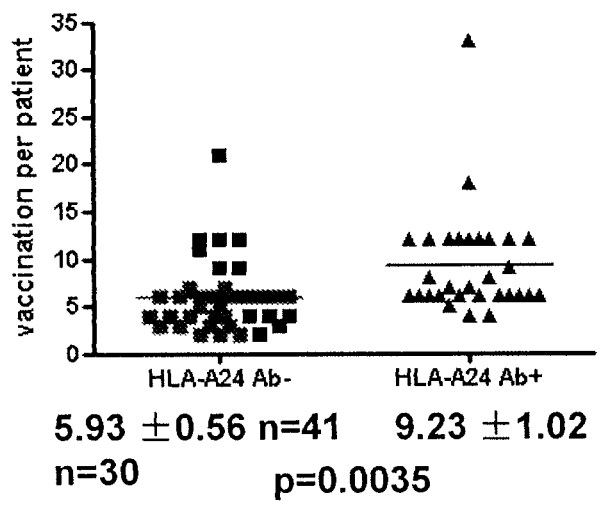

FIG. 13B presents the effect of the number of GVAX vaccinations per patient on HLA-A24 antibody induction in G-0010 patients.

Figure 13C:
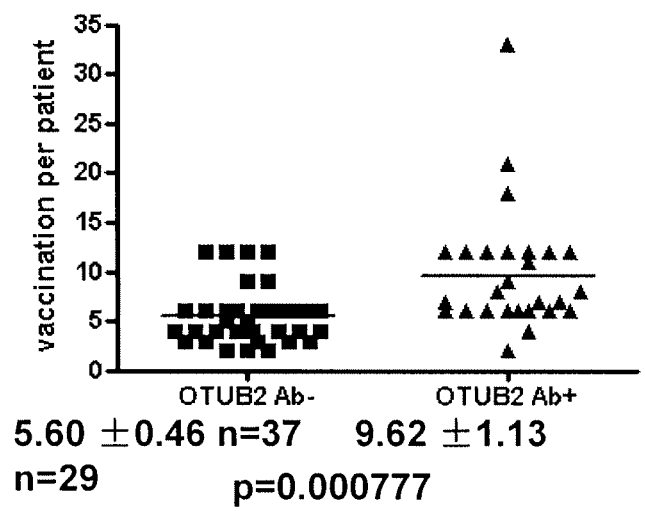

FIG. 13C presents the effect of the number of GVAX vaccinations per patient on OUTB2 antibody induction in G-OO10 patients.

Figure 13D:
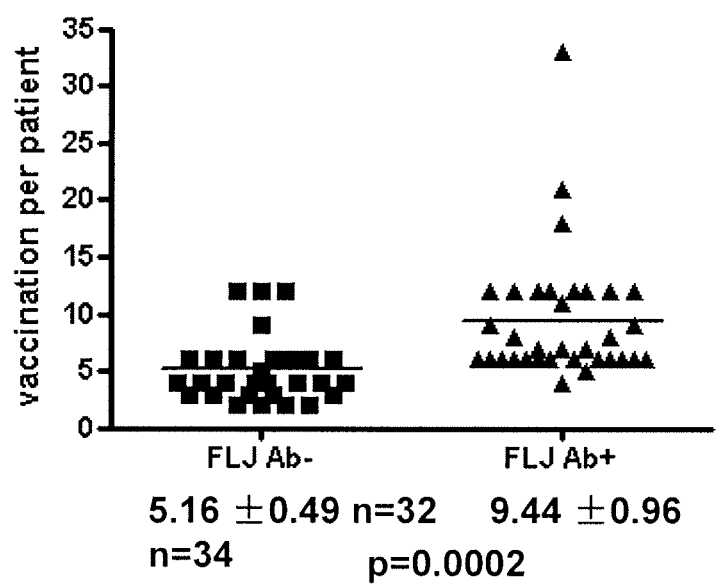

FIG. 13D presents the effect of the number of GVAX vaccinations per patient on FLJ14668 antibody induction in G-0010 patients.

Figure 14:
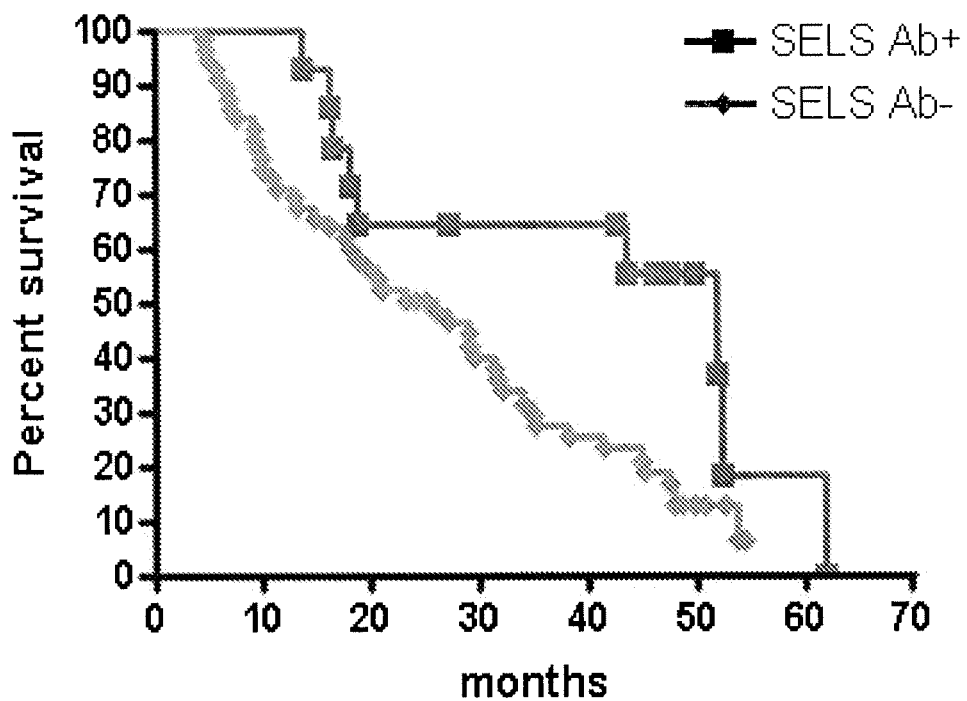

FIG. 14 presents a correlation of SELS Ab induction with survival in G-0010 patients following GVAX immunotherapy. MST=median survival time.

Figure 15A:
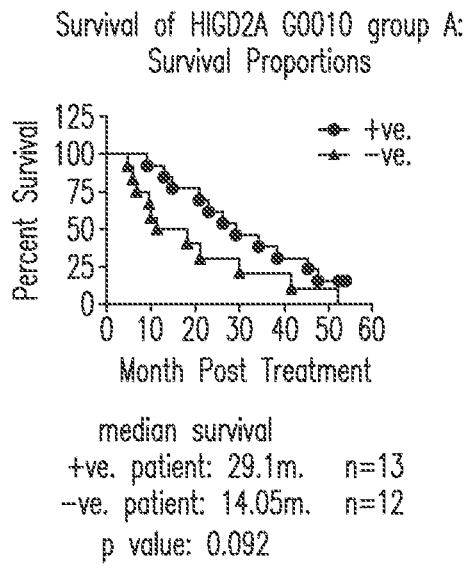
Figure 15B:
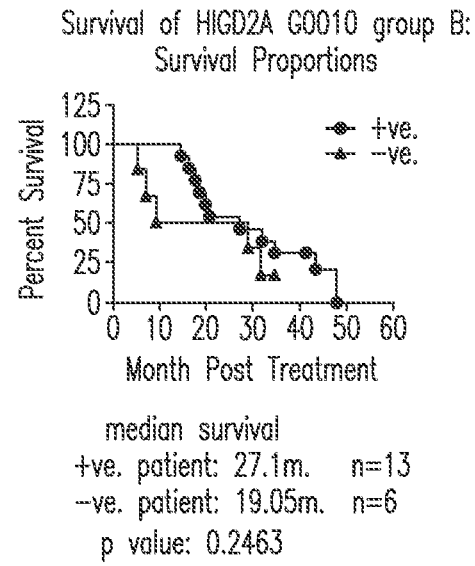
Figure 15C:
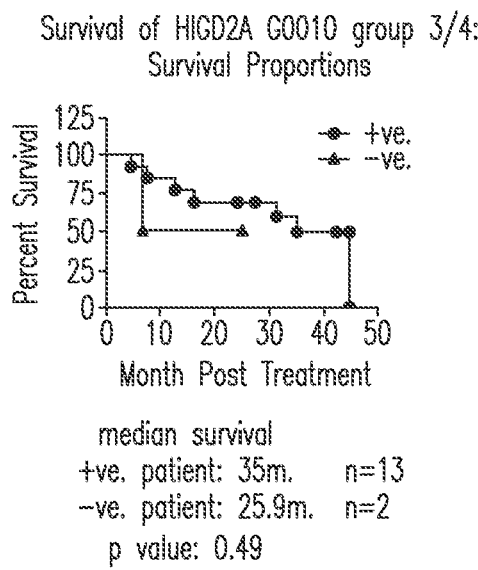
Figure 15D:
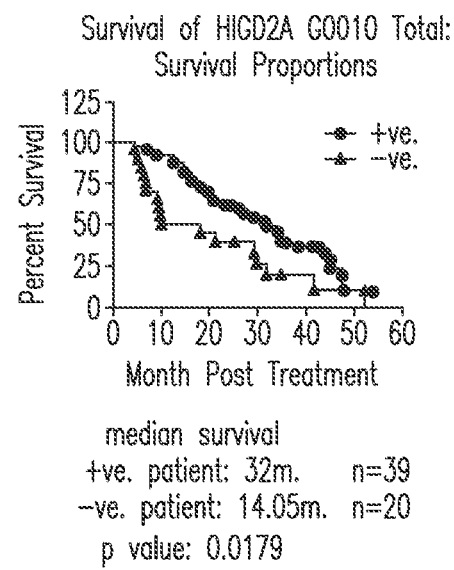

FIG. 15A presents a correlation of SELS Ab induction with survival in G-0010 Group A patients following GVAX immunotherapy. MST=median survival time. FIG. 15B presents a correlation of SELS Ab induction with survival in G-0010 Group B patients following GVAX immunotherapy. MST=median survival time. FIG. 15C presents a correlation of SELS Ab induction with survival in G-0010 Group 3/4 patients following GVAX immunotherapy. MST=median survival time. FIG. 15D presents a correlation of SELS Ab induction with survival in all G-0010 patients following GVAX immunotherapy. MST=median survival time.

Figure 16A:
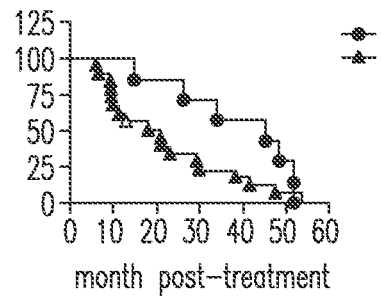
Figure 16B:
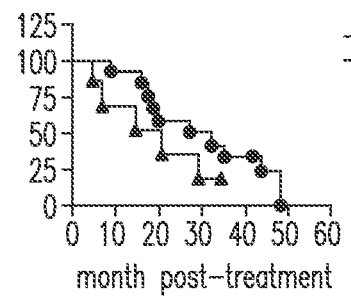
Figure 16C:
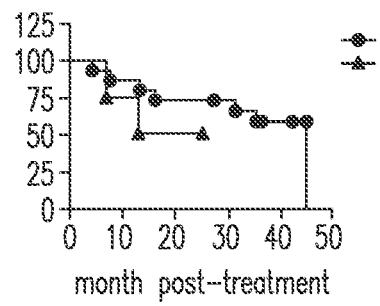
Figure 16D:
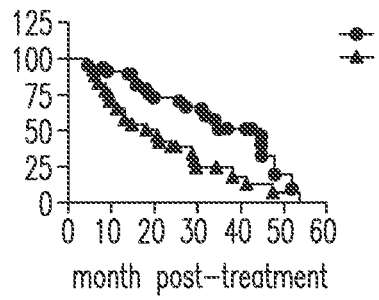

FIG. 16A presents a correlation of SSR3 Ab induction with survival in G-0010 Group A patients following GVAX immunotherapy. MST=median survival time. FIG. 16B presents a correlation of SSR3 Ab induction with survival in G-0010 Group B patients following GVAX immunotherapy. MST=median survival time. FIG. 16C presents a correlation of SSR3 Ab induction with survival in G-0010 Group 3/4 patients following GVAX immunotherapy. MST=median survival time. FIG. 16D presents a correlation of SSR3 Ab induction with survival in all G-0010 patients following GVAX immunotherapy. MST=median survival time.

Figure 17:
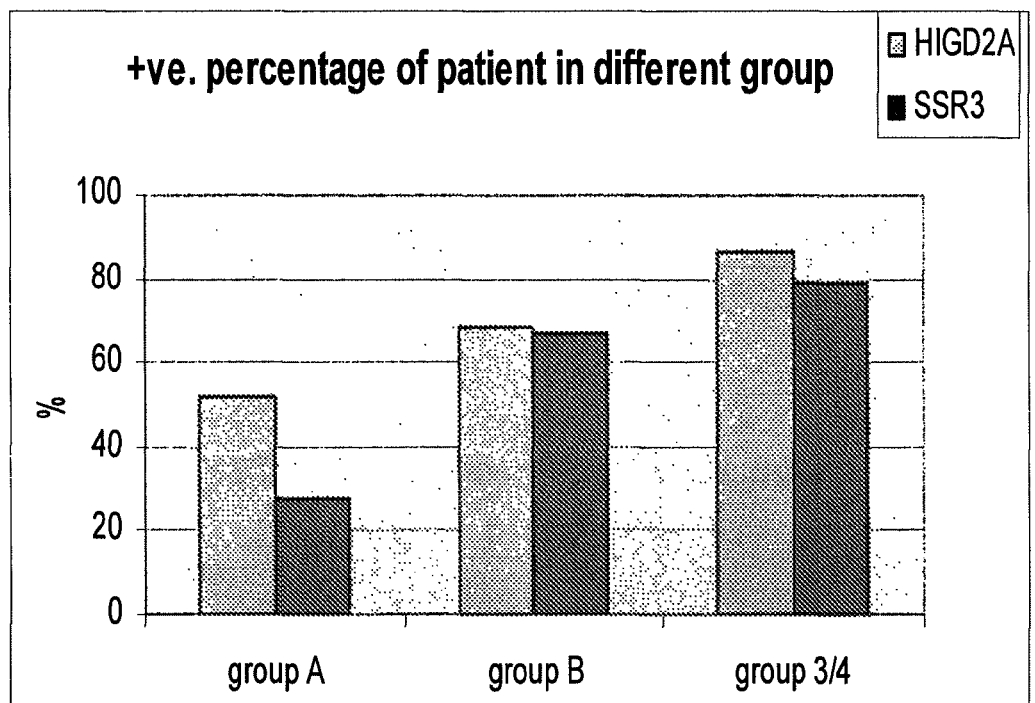

FIG. 17 presents the percentage of patients in groups A, B, and 3/4, respectively, with induction of HIGD2A or SSR3 Ab following GVAX immunotherapy.

Figure 18:
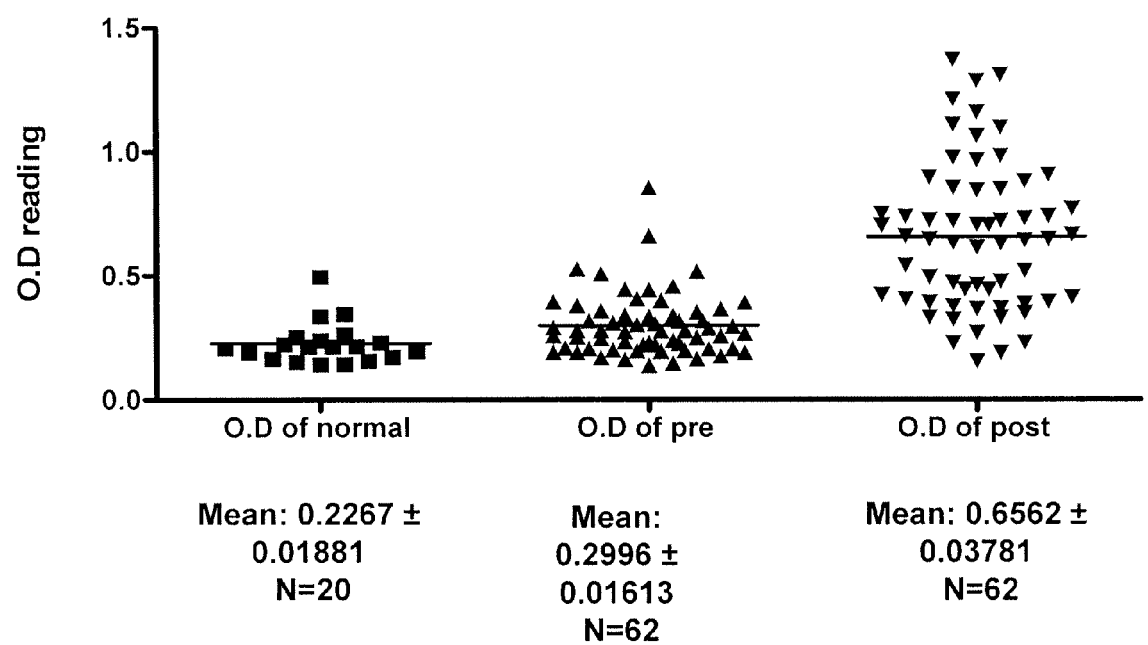

FIG. 18 presents an O.D. comparison of SSR3 Ab titer in normal (untreated) subjects, in patients before GVAX immunotherapy ("pre"), and in patients following GVAX immunotherapy ("post").

Figure 19:
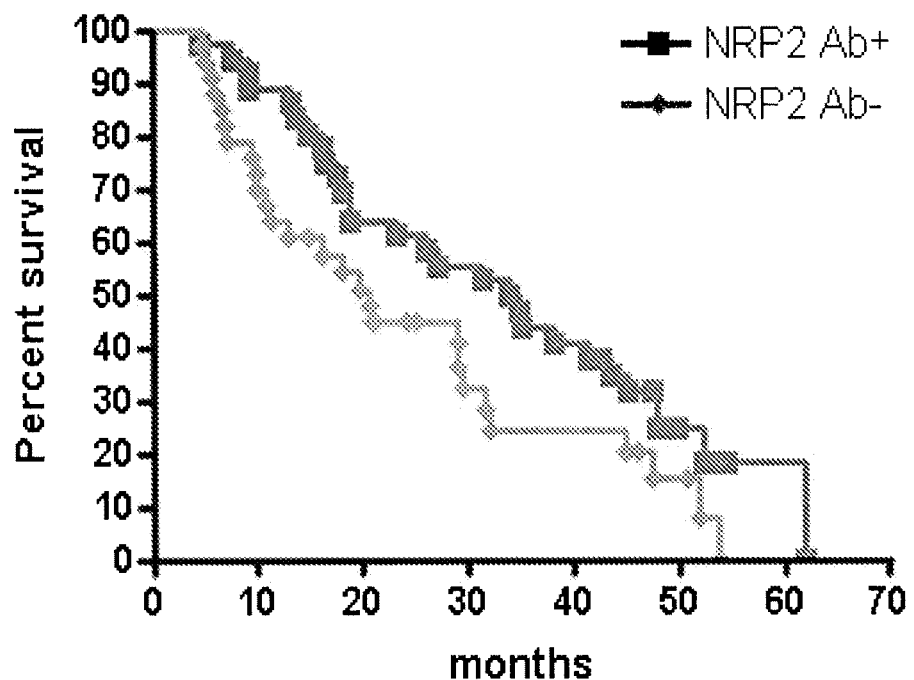

FIG. 19 presents a correlation of NRP2 Ab induction with survival in G-0010 patients following GVAX immunotherapy. MST=median survival time.

Figure 20A:
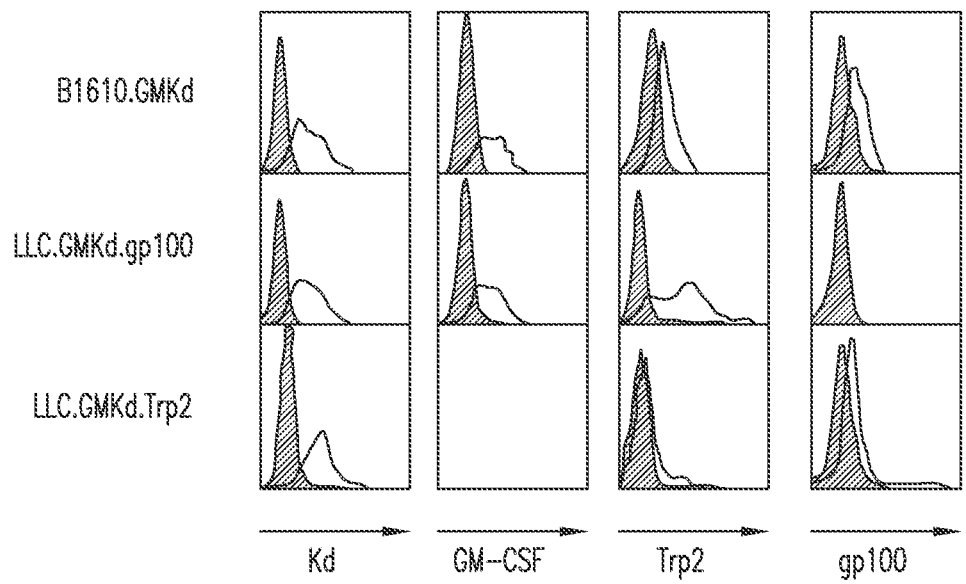

FIG. 20A presents flow cytometry analyses of expression of the GM-CSF and the B16-associated antigens Trp2 and gp100 by Lewis Lung Carcinoma (LLC) cells modified to secrete GM-CSF and to over-express either of the two B16-associated antigens Trp2 (LLC.GMKd.Trp2) and gp1OO (LLC.GMKd.gp100). The expression levels of GM-CSF on unmodified B16F10 cells (negative control) are represented by the shaded histogram. The open histograms represent GM-CSF expression levels of the B16F1O.GMKd, LLC.GMKd.gp1OO, and LLC.GM-Kd.Trp2 cells. For Trp2 and gp1OO expression, the antibody isotype control is represented by shaded histograms and specific antibodies against Trp2 and gp100 are represented by open histograms.

Figure 20B:
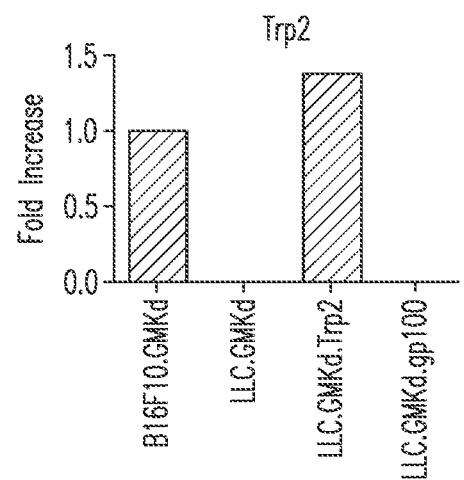
Figure 20C:
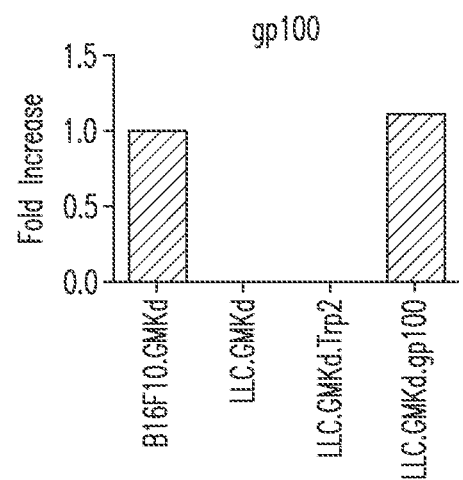

FIG. 20B presents a PCR analysis of the fold increase in gene copies of the melanoma-associated antigen Trp2 in the cells designated B16F10.GMKd, LLC.GMKd, LLC.GM-Kd.Trp2, and LLC.GMKd.gp100. FIG. 20C presents a PCR analysis of the fold increase in gene copies of the melanoma-associated antigen gp100 in the cells designated B16F10.GMKd, LLC.GMKd, LLC.GMKd.Trp2, and LLC.GMKd.gp100.

Figure 21A:
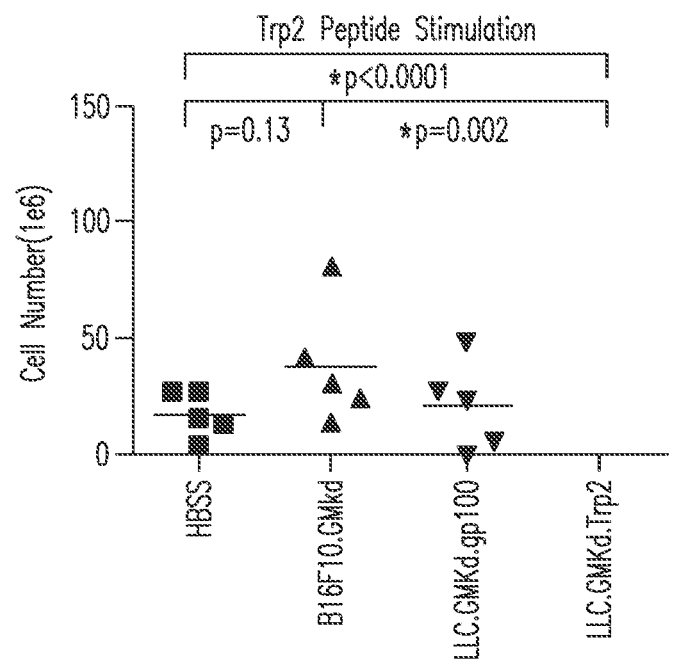
Figure 21B:
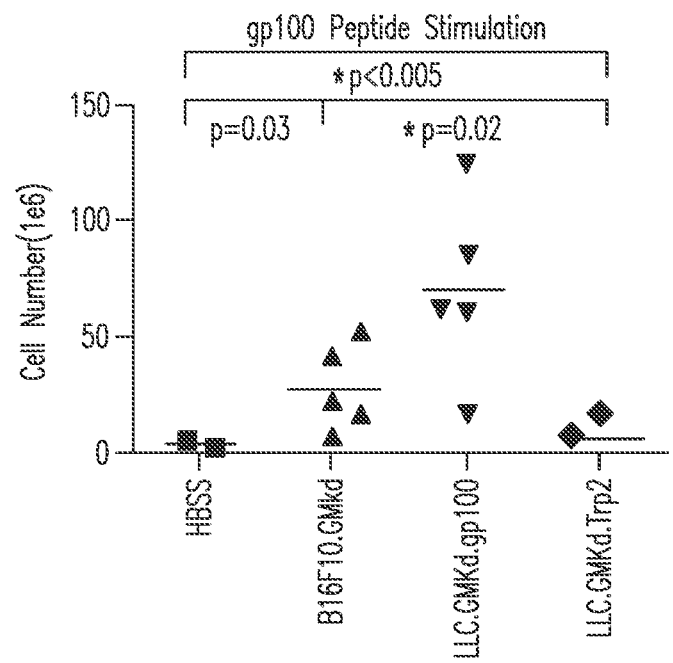

FIG. 21A presents Trp2 specific T-cell responses induced by administration of lentivirus modified LLC cell lines. B16F10 tumor-bearing C57BL/6 animals were immunized on day 3 after tumor cell implantation (2×10E5 cells) with 3×10E6 allogeneic GM-C SF-secreting B16F10 cells (B16F10.GMKd) as multivalent antigen immunotherapy or with GM-CSF-secreting LLC cells modified to over-express either of the two B16-associated antigens Trp2 (LLC.GM-Kd.Trp2) or gp100 (LLC.GMKd.gp 100) as single B16 antigen-specific immunotherapies. FIG. 21B presents gp100 specific T-cell responses induced by administration of lentivirus modified LLC cell lines. B16F10 tumor-bearing C57BL/6 animals were immunized on day 3 after tumor cell implantation (2×10E5 cells) with 3×10E6 allogeneic GM-C SF-secreting B16F10 cells (B16F10.GMKd) as multivalent antigen immunotherapy or with GM-CSF-secreting LLC cells modified to over-express either of the two B16-associated antigens Trp2 (LLC.GMKd.Trp2) or gp100 (LLC.G-MKd.gp 100) as single B16 antigen-specific immunotherapies.

Figure 22:
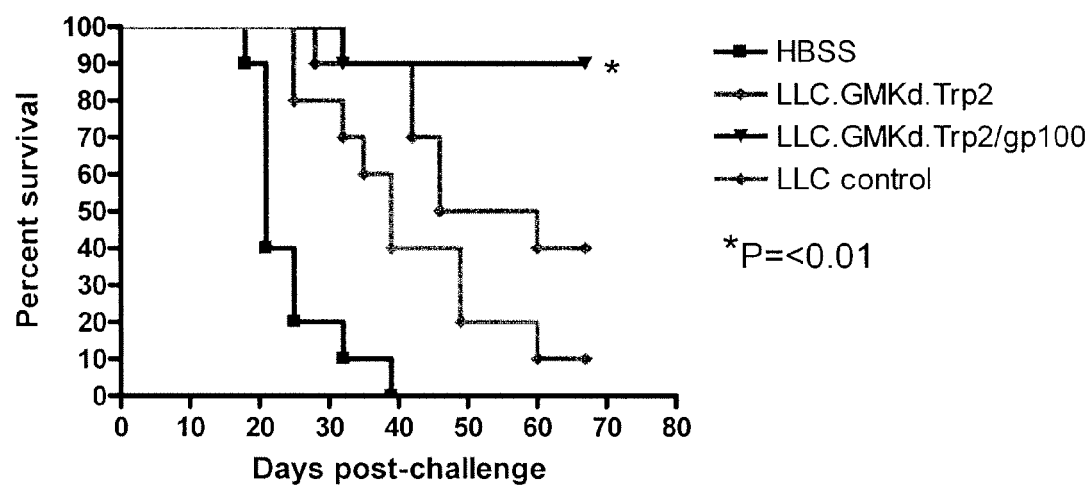

FIG. 22 presents survival data of mice immunized with GM-CSF-secreting Lewis Lung Carcinoma (LLC) cells modified to express one or two of B16-associated antigens. Trp2 (LLC.GMKd.Trp2) and Trp2/gp100 (LLC.GM-Kd.Trp2/gp100) and challenged with a lethal dose of live B16F10 cells.

5. DETAILED DESCRIPTION OF THE INVENTION

The present invention provides prostate cancer markers, compositions comprising such markers, and methods of using such markers to induce or increase an immune response against prostate cancer. The markers, compositions, immunoglobulins, and methods are useful, for example, for inducing or increasing an immune response, in particular a humoral immune response, against prostate cancer cells which immune response is preferably associated with prophylaxis of prostate cancer, treatment of prostate cancer, and/or amelioration of at least one symptom associated with prostate cancer.

Without intending to be bound to any particular theory or mechanism of action, it is believed that one aspect of the immune response induced by therapy with genetically modified tumor cells that express a cytokine and a prostate tumor-associated antigen is an immune response against certain polypeptides expressed by the genetically modified tumor cell and/or cells from the tumor afflicting the subject. It is also believed that this immune response plays an important role in the effectiveness of this therapy to treat, e.g., prostate cancer.

5.1 Definitions

By the term "cytokine" or grammatical equivalents, herein is meant the general class of hormones of the cells of the immune system, including lymphokines, monokines, and others. The definition includes, without limitation, those hormones that act locally and do not circulate in the blood, and which, when used in accord with the present invention, will result in an alteration of an individual's immune response. The term "cytokine" or "cytokines" as used herein refers to the general class of biological molecules, which affect cells of the immune system. The definition is meant to include, but is not limited to, those biological molecules that act locally or may circulate in the blood, and which, when used in the compositions or methods of the present invention serve to regulate or modulate an individual's immune response to cancer. Exemplary cytokines for use in practicing the invention include, but are not limited to, interferon-alpha (IFN-alpha), IFN-beta, and IFN-gamma, interleukins (e.g., IL-1 to IL-29, in particular, IL-2, IL-7, IL-12, IL-15 and IL-18), tumor necrosis factors (e.g., TNF-alpha and TNF-beta), erythropoietin (EPO), MIP3a, ICAM, macrophage colony stimulating factor (M-CSF), granulocyte colony stimulating factor (G-CSF) and granulocyte-macrophage colony stimulating factor (GM-CSF).

As used herein, the terms "cancer", "cancer cells", "neoplastic cells", "neoplasia", "tumor", and "tumor cells" (used interchangeably) refer to cells that exhibit relatively autonomous growth, so that they exhibit an aberrant growth phenotype or aberrant cell status characterized by a significant loss of control of cell proliferation. A tumor cell may be a hyperplastic cell, a cell that shows a lack of contact inhibition of growth in vitro or in vivo, a cell that is incapable of metastasis in vivo, or a cell that is capable of metastasis in vivo. Neoplastic cells can be malignant or benign. It follows that cancer cells are considered to have an aberrant cell status. "Tumor cells" may be derived from a primary tumor or derived from a tumor metastases. The "tumor cells" may be recently isolated from a patient (a "primary tumor cell") or may be the product of long term in vitro culture.

The term "primary tumor cell" is used in accordance with the meaning in the art. A primary tumor cell is a cancer cell that is isolated from a tumor in a mammal and has not been extensively cultured in vitro.

The term "antigen from a tumor cell" and "tumor antigen" and "tumor cell antigen" and "rumor-associated antigen" may be used interchangeably herein and refer to any protein, peptide, carbohydrate or other component derived from or expressed by a tumor cell which is capable of eliciting an immune response. The definition is meant to include, but is not limited to, whole tumor cells, tumor cell fragments, plasma membranes taken from a tumor cell, proteins purified from the cell surface or membrane of a tumor cell, unique carbohydrate moieties associated with the cell surface of a tumor cell or tumor antigens expressed from a vector in a cell. The definition also includes those antigens from the surface of the cell, which require special treatment of the cells to access.

The term "genetically modified tumor cell" as used herein refers to a composition comprising a population of cells that has been genetically modified to express a transgene, and that is administered to a patient as part of a cancer treatment regimen. The genetically modified tumor cell vaccine comprises tumor cells which are "autologous" or "allogeneic" to the patient undergoing treatment or "bystander cells" that are mixed with tumor cells taken from the patient. Generally, the genetically modified tumor cell is of the same general type of tumor cell as is afflicting the patient, e.g., if the patient is afflicted with metastatic prostate cancer, the genetically modified tumor cell is also a metastatic prostate cancer cell. A GM-CSF-expressing genetically modified tumor cell vaccine may be referred to herein as "GVAX"®. Autologous and allogeneic cancer cells that have been genetically modified to express a cytokine, e.g., GM-CS, followed by readministration to a patient for the treatment of cancer are described in U.S. Pat. Nos. 5,637,483, 5,904,920, 6,277,368 and 6,350,445, each of which is expressly incorporated by reference herein. A form of GM-CSF-expressing genetically modified cancer cells or a "cytokine-expressing cellular vaccine" for the treatment of pancreatic cancer is described in U.S. Pat. Nos. 6,033,674 and 5,985,290, both of which are expressly incorporated by reference herein. A universal immunomodulatory cytokine-expressing bystander cell line is described in U.S. Pat. No. 6,464,973, expressly incorporated by reference herein.

The term "enhanced expression" as used herein, refers to a cell producing higher levels of a particular protein than would be produced by the naturally occurring cell or the parental cell from which it was derived. Cells may be genetically modified to increase the expression of a cytokine, such as GM-CSF, or a prostate tumor-associated antigen. The expression of cytokine or tumor antigen may be increased using any method known in the art, such as genetically modifying promoter regions of genomic sequences or genetically altering cellular signaling pathways to increase production of the cytokine or tumor antigen. Also, cells can be transduced with a vector coding for the cytokine or tumor antigen, or immunogenic fragments thereof.

By the term "systemic immune response" or grammatical equivalents herein is meant an immune response which is not localized, but affects the individual as a whole, thus allowing specific subsequent responses to the same stimulus.

As used herein, the term "proliferation-incompetent" or "inactivated" refers to cells that are unable to undergo multiple rounds of mitosis, but still retain the capability to express proteins such as cytokines or tumor antigens. This may be achieved through numerous methods known to those skilled in the art, Embodiments of the invention include, but are not limited to, treatments that inhibit at least about 95%, at least about 99% or substantially 100% of the cells from further proliferation. In one embodiment, the cells are irradiated at a dose of from about 50 to about 200 rads/min or from about 120 to about 140 rads/min prior to administration to the mammal. Typically, when using irradiation, the levels required are 2,500 rads, 5,000 rads, 10,000 rads, 15,000 rads or 20,000 rads. In several embodiments of the invention the cells produce beta-filamin or immunogenic fragment thereof, two days after irradiation, at a rate that is at least about 10%, at least about 20%, at least about 50% or at least about 100% of the pre-irradiated level, when standardized for viable cell number. In one embodiment of the invention, cells are rendered proliferation incompetent by irradiation prior to administration to the subject.

By the term "individual", "subject" or grammatical equivalents thereof is meant any one individual mammal.

By the term "reversal of an established tumor" or grammatical equivalents herein is meant the suppression, regression, or partial or complete disappearance of a pre-existing tumor. The definition is meant to include any diminution in the size, potency or growth rate of a pre-existing tumor.

The terms "treatment", "therapeutic use", or "medicinal use" as used herein, shall refer to any and all uses of the claimed compositions which remedy a disease state or symptom, or otherwise prevent, hinder, retard, or reverse the progression of disease or other undesirable symptoms in any way whatsoever.

The term "administered" refers to any method that introduces the cells of the invention (e.g. cancer vaccine) to a mammal. This includes, but is not limited to, intradermal, parenteral, intramuscular, subcutaneous, intraperitoneal, intranasal, intravenous (including via an indwelling catheter), intratumoral, via an afferent lymph vessel, or by another route that is suitable in view of the patient's condition. The compositions of this invention may be administered to the subject at any site. For example, they can be delivered to a site that is "distal" to or "distant" from the primary tumor.

The term "induced immune response" or "de novo immune response" as used herein means that a specific immune activation is detectable (e.g. detection of a B-cell and/or T-cell response). An example of an induced immune response is detection of an amount of an antibody that binds an antigen which is not detected prior to administration of a cytokine-expressing cellular vaccine of the invention.

The term "increased immune response" as used herein means that a detectable increase of a specific immune activation is detectable (e.g. an increase in B-cell and/or T-cell response). An example of an increased immune response is an increase in the amount of an antibody that binds an antigen which is detected a tower level prior to administration of a cytokine-expressing cellular vaccine of the invention. Another example, is an increased cellular immune response. A cellular immune response involves T cells, and can be observed in vitro (e.g. measured by a Chromium release assay) or in vivo. An increased immune response is typically accompanied by an increase of a specific population of immune cells.

By the term "retarding the growth of a tumor" is meant the slowing of the growth rate of a tumor, the inhibition of an increase in tumor size or tumor cell number, or the reduction in tumor cell number, tumor size, or numbers of tumors.

The term "inhibiting tumor growth" refers to any measurable decrease in tumor mass, tumor volume, amount of tumor cells or growth rate of the tumor. Measurable decreases in tumor mass can be detected by numerous methods known to those skilled in the art. These include direct measurement of accessible tumors, counting of tumor cells (e.g. present in blood), measurements of tumor antigens (e.g. Prostate Specific Antigen (PSA), Alphafeltoprotein (AFP) and various visualization techniques (e.g. MRI, CAT-scan and X-rays). Decreases in the tumor growth rate typically correlates with longer survival time for a mammal with cancer.

By the term "therapeutically effective amount" or grammatical equivalents herein refers to an amount of an agent, e.g., a cytokine-expressing cellular vaccine of the invention, that is sufficient to modulate, either by stimulation or suppression, the immune response of an individual. This amount may be different for different individuals, different tumor types, and different preparations. The "therapeutically effective amount" is determined using procedures routinely employed by those of skill in the art such that an "improved therapeutic outcome" results.

As used herein, the terms "improved therapeutic outcome" and "enhanced therapeutic efficacy," relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria including an increase in life expectancy or an improvement in quality of life (as further described herein)

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine G).

Stringent hybridization conditions" and "stringent wash conditions" in the context of nucleic acid hybridization experiments such as Southern and Northern hybridizations are sequence dependent, and are different under different environmental parameters. Longer sequences hybridize at higher temperatures. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays" Elsevier, New York. Generally, highly stringent hybridization and wash conditions are selected to be about 5° C. to 20° C. (preferably 5° C.) lower than the thermal melting point ($T_m$) for the specific sequence at a defined ionic strength and pH. Typically, under highly stringent conditions a probe will hybridize to its target subsequence, but to no other unrelated sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids that have more than 100 complementary residues on a tilter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C., for IS minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 300° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described herein or by visual inspection For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman. Adv. Appl. Math. 2:482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J. Mot. Biol. 215: 403-410 (1990), with software that is publicly available through the National Center for r Biotechnology Information, or by visual inspection (see generally, Ausubel et al., infra). For purposes of the present invention, optimal alignment of sequences for comparison is most preferably conducted by the local homology algorithm of Smith & Waterman, Adv. Appt. Math. 2: 482 (1981).

As used herein, a "peptide" refers to an amino acid polymer containing between about 8 and about 12 amino acids linked together via peptide bonds. A peptide according to the present invention can comprise additional atoms beyond those of the 8 to twelve amino acids, so long as the peptide retains the ability to bind an MHC I receptor, e.g., an HLA-A2 receptor, and form a ternary complex with the T-cell receptor, the MHC I receptor, and the peptide.

Conservative substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W).

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range oft from 48 minutes to 72 minutes. Where the term "about" modifies a value that must be an integer, and 10% above or below the value is not also an integer, the modified value should be rounded to the nearest whole number. For example, "about 12 amino acids" means a range of 11 to 13 amino acids.

The term "physiological conditions," as used herein, refers to the salt concentrations normally observed in human serum. One skilled in the art will recognize that physiological conditions need not mirror the exact proportions of all ions found in human serum, rather, considerable adjustment can be made in the exact concentration of sodium, potassium, calcium, chloride, and other ions, while the overall ionic strength of the solution remains constant.

5.2 Antigens Associated with Therapy with Proliferation Incompetent Tumor Cells that Express GM-CSF and a Prostate Tumor-associated Antigen In certain aspects as described below, the invention provides methods that comprise inducing or increasing immune responses against antigens associated with a likelihood of responsiveness to treatment with proliferation-incompetent tumor cells that express cytokines, e.g., GM-CSF. In some embodiments, the therapies are predicted to result in an improved therapeutic outcome for the subject, for example, a reduction in the level of PSA in the patient's serum, a decrease in cancer-associated pain or improvement in the condition of the patient according to any clinically acceptable criteria, including but not limited to a decrease in metastases, an increase in life expectancy or an improvement in quality of life. The antigens may be expressed endogenously by cells native to the subject or may be exogenously provided to the subject by, e.g., the administered genetically modified tumor cells. The discussion below briefly describes examples of such antigens.

HLA class I histocompatibility antigen (alias MHC class I antigen A*24, Aw-24, A-9) is a 40689 Da protein of 365 amino acids (SEQ ID NO: 1) encoded on chromosome 6 (Entrez Gene cytogenetic band 6p21.3). Representative nucleotide sequence HLA-A2402 is shown (SEQ ID NO: 2). HLA-A24 belongs to the HLA class I heavy chain paralogues (N'guyen et al. 1985; Little et al. 1992). This class I molecule is a heterodimer consisting of a heavy chain and a light chain (j3-2 microglobulin). The heavy chain is anchored in the membrane as a single-pass type I membrane protein. HLA-A24 plays a central role in the immune system by presenting peptides derived from the endoplasmic reticulum lumen. The following alleles of A-24 are known: A*2401, A*2402, A*2403, A*2406, A*2408 (A9HH), A*2410 (A*24JV), A*2413 (A*24YM) and A*2414 (A*24SA). Allele A*2402 is represented in all major racial groups. Allele A*2406 and allele A*2413 are found in the Australian Aboriginal population. Allele A*2414 is found in individuals of South American descent. See N'Guyen C, Sodoyer R, Trucy J, Strachan T, Jordan B R. The HLA-AW24 gene: sequence, surroundings and comparison with the HLA-A2 and HLA-A3 genes. Immunogenetics. 1985; 21(5):479-89. PMID: 2987115 and Little A M, Madrigal J A, Parham P. Molecular definition of an elusive third HLA-A9 molecule: HLA-A9.3. Immunogenetics. 1992; 35(1):41-5. PMID: 1729171

FLJ14668 encodes a protein (SEQ ID NO: 3), also designated hypothetical protein LOC84908 (NP_116211), on chromosome 2 (ENSEMBL cytogenetic band: 2p13.3). A representative nucleotide sequence encoding FLJ14667 protein is NM_032822 (SEQ ID NO: 4). The protein sequence for FLJ14668 is most similar to the human Sm G protein, a "common protein" component of the snRNP. The region of greatest homology is within the Sm 1 and 2 motifs that characterize the protein members of the Sm group and it is therefore thought that LOC84908 bears some functional similarity, however, function and role are currently unknown (Lehner and Sanderson 2004: Simpson et al. 2000) See Lehner, B. and Sanderson, C. M. A protein interaction framework for human mRNA degradation, Genome Res. 14 (7), 1315-1323 (2004), PMID: 15231747 and Simpson, J. C., Wellenreuther, R., Poustka, A., Pepperkok, R. and Wiemann, S. Systematic subcellular localization of novel proteins identified by large-scale cDNA sequencing, EMBO Rep. 1 (3), 287-292 (2000)

Cardiolipin (bisphosphadyl glycerol) is an important component of the inner mitochondrial membrane, where it constitutes about 20% of the total lipid. Cardiolipin is a dimeric phospholipid synthesized from two lipid substrates. CDP-diacylglycerol and phosphatidylglycerol. Its synthesis is catalyzed by the enzyme CL synthase, which is encoded by the gene CRD1 (CLS1). It is typically present in metabolically active cells of the heart and skeletal muscle. It has also been observed in certain bacterial membranes. It serves as an insulator and stabilizes the activity of protein complexes important to the electron transport chain Anti-cardiolipin antibodies can also be increased in numerous conditions, including malaria and tuberculosis (McNeil et al., 1990). See McNeil, H. P., Simpson. R. J., Chesterman, C. N., Krilis, S. A. Anti-phospholipid antibodies are directed against a complex antigen that includes a lipid-binding inhibitor of coagulation: beta 2-glycoprotein I (apolipoprotein II). Proc. Natl. Acad. Sci. U.S.A. 87 (11): 4120 (1990).

As Cardiolipin is a phospholipid, and thus not encoded by a nucleic acid sequence, the phrase "genetically modified to express the coding sequence of Cardiolipin" as used herein refers to any genetic modification of a cell or population of cells which results in the increased production of Cardiolipin in the cell. Thus, in some embodiments, a cell genetically modified to express Cardiolipin in accordance with the methods provided herein is genetically modified to express an enzyme which catalyzes the synthesis of Cardiolipin, e.g., CL synthase. In other embodiments, a cell genetically modified to express Cardiolipin in accordance with the methods provided herein is genetically modified to express an enzyme which catalyzes the synthesis of the cardiolipin precursors CDP-diacylglycerol and phosphatidylglycerol. In some embodiments, the enzyme is CDP-diacylglycerol synthase 1 (CDS1). In some embodiments, the enzyme is CDP-diacylglycerol synthase 2 (CDS2).

NNAT (alias Peg5, MGC1439) encodes 2 different isoforms of Neuronatin—alpha (9237 Da, 81 amino acids, SEQ ID NO: 7) and beta (6022 Da, 54 amino acids, SEQ ID NO: 92). The Beta (or #2) variant lacks an alternate in-frame exon compared to alpha (or #1) variant, resulting in an isoform that is shorter compared to isoform alpha. NNAT is encoded on chromosome 20 (Ensembl cytogenetic band: 20q11.23). Representative nucleotide sequence NM_005386 (transcript variant 1: SEQ ID NO: 8) and NM_181689 (transcript variant 2: SEQ ID NO: 94). Neuronatin is a proteolipid that may be involved in the regulation of ion channels during brain development (Duo and Joseph 1996a). The encoded protein may also play a role in forming and maintaining the structure of the nervous system, specifically in the segment identity in the hindbrain and pituitary development, and maturation or maintenance of the overall structure (Usui et al. 1997). This gene is found within an intron of the BLCAP gene, but on the opposite strand. This gene is imprinted and is expressed only from the paternal allele, while BLCAP is not imprinted. Abundant in 18-24 week old fetal brain. Postnatally its expression, declines and only minimal levels are present in adulthood (Duo and Joseph, 1996b). See Usui, H., Morii, K., Tanaka, R., Tamura, T., Washiyamta, K., Ichikawa, T. and Kumanishi, T. cDNA cloning and mRNA expression analysis of the human neuronatin. High level expression in human pituitary gland and pituitary adenomas. J. Mol. Neurosci. 9 (1), 55-6(1997). PMID: 9356927 and Dou, D. and Joseph, R. Cloning of human neuronatin gene and its localization to chromosome-20q 11.2-12: the deduced protein is a novel 'proteolipid' Brain Res. 723 (1-2), 8-22 (1996a). PMID: 8813377 and Dou, D. and Joseph, R. Structure and organization of the human neuronatin gene Genomics 33 (2), 292-297 (1996b). PMID: 8660979

SELS (Alias: VIMP. ADO15, SBB18, SEPS1, AD-015, MGC2553, MGC104346) is a 21116 Da protein (representative amino acid sequence NP_982298.1; SEQ ID NO: 11) of 189 amino acids encoded on chromosome 15q26.3 (Ensembl cytogenetic band). Representative nucleotide sequence NM_203472 (SEQ ID NO: 12). SELS is involved in the degradation process of misfolded endoplasmic reticulum (ER) luminal proteins, participating in the transfer of misfolded proteins from the ER to the cytosol, where they are destroyed by the proteasome in a ubiquitin-dependent manner (Ye et al. 2005). SELS may act by serving as a linker between DERL1, which mediates the retrotranslocation of misfolded proteins into the cytosol, and the ATPase complex VCP, which mediates the translocation and ubiquitination and suggesting that it forms a membrane complex with DERL1 that serves as a receptor for VCP (Lilley et al. 2005). See Ye, Y., Shibuta, Y., Kikkert, M., van Voorden, S., Wiertz, E. And Rapoport, T. A. Inaugural Article: Recruitment of the p97 ATPase and ubiquitin ligases to the site of retrotranslocation at the endoplasmic reticulum membrane. Proc. Natl. Acad. Sci. U.S.A. 102 (40), 14132-14138 (2005); and Lilley, B. N. and Ploegh, H. L. Multiprotein complexes that fink dislocation, ubiquitination, and extraction of misfolded proteins from the endoplasmic reticulum membrane. Proc. Natl. Acad. Sci. U.S.A. 102 (40), 14296-14301 (2005).

HIGD2A (alias MGC2198) encodes a 11529 Da protein (reference NP_620175) of 106 amino acids (SEQ ID NO: 5) encoded on chromosome 5 (Ensembl cytogenetic band: 5q35.2). Representative nucleotide sequence NM_138820 (SEQ ID NO: 6). Current function and role is unknown. Potentially encodes a multi-pass membrane protein (Strausberg et al. 2002). See Strausberg et al. Generation and initial analysis of more than 15,000 full-length human and mouse cDNA sequences. Proc. Natl. Acad. Sci. U.S.A. 99 (26), 16899-16903 (2002). PMID: 12477932

SSR3 (alias TRAPG, SSR gamma) is a 21080 Da protein (representative protein sequence NP_009038.1 (SEQ ID NO: 9)) of 185 amino acids encoded on chromosome 3q25.31 (Ensembl cytogenetic band). Representative nucleotide sequence NM_007107 (SEQ ID NO: 10). The signal sequence receptor (SSR) is a glycosylated endoplasmic reticulum (ER) membrane receptor associated with protein translocation across the ER membrane (Wang et al. 1999). The SSR is comprised of four membrane proteins/subunits: alpha, beta, gamma, and delta (Hartmann et al. 1993). The first two are glycosylated subunits and the latter two are non-glycosylated subunits. The protein encoded by this gene is the gamma subunit and is predicted to span the membrane four times. See Wang, L. and Dobberstein, B. Oligomeric complexes involved in translocation of proteins across the membrane of the endoplasmic reticulum. FEBS Lett. 457 (3), 316-322 (1999); and Hartmann, E., Gorlich, D., Kostka, S., Otto. A., Kraft, R., Knespel, S., Burger, E., Rapoport, T. A. and Prehn, S. A tetrameric complex of membrane proteins in the endoplasmic reticulum. Eur. J. Biochem. 214(2), 375-381 (1993).

Nrp2 (aliases NP2, NPN2, PRO2714, MGC126574, VEGF165R2) encodes the 104831 Da, 931 amino acid protein neuropilin-2 (representative amino acid sequence NP_003863: SEQ ID NO: 13) encoded on chromosome 2q33.3 (Ensembl cytogenetic band). Representative nucleotide sequence NM_003872.2 (SEQ ID NO: 14). This gene encodes a member of the neuropilin family of receptor proteins (Chen et al. 1997). The encoded transmembrane protein binds to SEMA3C protein (sema domain, immunoglobulin domain (Ig), short basic domain, secreted, (semaphorin) 3C) and SEMA3F protein (sema domain, immunoglobulin domain (1 g), short basic domain, secreted, (semaphorin) 3F), and interacts with vascular endothelial growth factor (VEGF). This protein may play a role in cardiovascular development and axon guidance (Giger et al. 1998; Takahashi et al. 1998; (Chen et al. 1998). Multiple transcript variants encoding distinct isoforms have been identified for this gene. See Chen, H., He, Z., Bagri, A. and Tessier-Lavigne, M, Semaphorin-neuropilin interactions underlying sympathetic axon responses to class III semaphorins. Neuron 21 (6), 1283-1290 (1998); Giger, R. J., Urquhart, E. R., Gillespie, S. K., Levengood, D. V., Ginty, D. D. and Kolodkin, A. L., Neuropilin-2 is a receptor for semaphorin IV; insight into the structural basis of receptor function and specificity, Neuron 21 (5), 1079-1092 (1998); Takahashi, T., Nakamura, F., Jin, L., Kalb, R. G. and Strittmatter, S. M, Semaphorins A and E act as antagonists of neuropilin-1 and agonists of neuropilin-2 receptors, Nat. Neurosci. 1 (6), 487-493 (1998); and Chen, H., Chedotal, A., He, Z., Goodman, C. S. and Tessier-Lavigne, M. Neuropilin-2, a novel member of the neuropilin family, is a high affinity receptor for the semaphorins Sema E and Sema IV but not Sema III, Neuron 19 (3), 547-559 (1997).

5.3 Methods of Using Antigens

The present invention provides an methods of inducing or increasing an immune response to prostate cancer in a mammalian, preferably a human, subject, Desirably, the method effects a systemic immune response, i.e., a T-cell response and/or a B-cell response, to the cancer. In some embodiments, the method comprises administering to the patient a cellular immunotherapy composition, wherein the cellular immunotherapy composition comprises cells which are genetically modified to express a cytokine and one or more prostate tumor-associated antigens. The one or more prostate tumor-associated antigens can be one or more of the antigens of the cancer found in the patient under treatment. In some embodiments, the prostate tumor-associated antigen is selected from the group consisting of HLA-A24. FLJ14668, Cardiolipin, Neuronatin (NNAT), Selenoprotein (SELS), HIG1 domain family, member 2A (HIGD2A), Signal sequence receptor, gamma (SSR3) and Neuropilin 2 (NRP2). The cells can be rendered proliferation incompetent, such as e.g., by irradiation. Upon administration of the cytokine-expressing cellular immunotherapy, an immune response to the cancer can be elicited or enhanced.

Thus, in one aspect, the method is effective to stimulate a systemic immune response in a prostate cancer patient, comprising administering to the patient a therapeutically effective amount of a cellular immunotherapy composition comprising one or more populations of proliferation incompetent cells genetically modified to express a cytokine and a prostate-tumor associated antigen. The systemic immune response to the cellular immunotherapy may result in tumor regression or inhibit the growth of the tumor. In some embodiments, the prostate cancer is metastatic prostate cancer. In some embodiments, the prostate cancer is refractory to hormone therapy. In some embodiments, the primary prostate tumor has been treated, e.g., by ablation or rescission and metastases of the primary prostate cancer are treated by immunotherapy as described herein.

In another aspect, the method is effective to increase or enhance a systemic immune response in a prostate cancer patient, comprising administering to the patient a therapeutically effective amount of a cellular immunotherapy composition comprising one or more populations of proliferation incompetent cells genetically modified to express a cytokine and a prostate-tumor associated antigen. The systemic immune response to the cellular immunotherapy may result in tumor regression or inhibit the growth of the tumor. In some embodiments, the prostate cancer is metastatic prostate cancer. In some embodiments, the prostate cancer is refractory to hormone therapy. In some embodiments, the primary prostate tumor has been treated, e.g., by ablation or rescission and metastases of the primary prostate cancer are treated by immunotherapy as described herein.

Typically the genetically modified cells are rendered proliferation incompetent prior to administration. In one embodiment, the mammal is a human who harbors prostate tumor cells of the same type as the genetically modified cells of the cellular immunotherapy. In a preferred embodiment, an improved therapeutic outcome is evident following administration of the genetically modified cells to the subject. Any of the various parameters of an improved therapeutic outcome for a prostate cancer patient known to those of skill in the art may be used to assess the efficacy of the cellular immunotherapy, e.g., decreased serum concentrations of tumor specific markers, increased overall survival time, increased progression-free survival, decreased tumor size, decreased bone metastasis marker response, increased impact on minimal residual disease, increased, induction of antibody response to the cancer cells that have been rendered proliferation-incompetent, increased induction of delayed-type-hypersensitivity (DTH) response to injections of autologous tumor, increased induction of T cell response to autologous tumor or candidate tumor-associated antigens, increased impact on circulating T cell and dendritic cell numbers, phenotype, and function, cytokine response, decreased concentrations of prostate-specific antigen (PSA), reduced slope of PSA doubling time, increased PSA doubling time, reduced metastasis as measured by bone scan, increased time to progression, increased survival time as compared to the Halabi nomogram, decreased serum concentrations of ICTP, or decreased concentrations of serum C-reactive protein. See Halabi et al., 2003. J Clin Oncol 21:1232-7, for a description of the Halabi nomogram.

In one approach, the cellular immunotherapy comprises a single population oft cells that is modified to express a cytokine, e.g. GM-CSF, and a prostate tumor-associated antigen. In another approach, the immunotherapy comprises a combination of two or more populations of cells individually modified to express one component of the immunotherapy, e.g. a cytokine or a prostate tumor-associated antigen.

In general, a cytokine-expressing cellular immunotherapy for use in practicing the methods described herein comprises tumor cells selected from the group consisting of autologous tumor cells, allogeneic tumor cells and tumor cell lines (i.e., bystander cells). In one aspect of the invention, the cells of the cellular immunotherapy are administered to the same individual from whom they were derived (autologous). In another aspect of the invention, the cells of the cellular immunotherapy and the tumor are derived from different individuals (allogeneic or bystander).

By way of example, in one approach, the same population of cells is genetically modified to express the coding sequence for a cytokine and one or more prostate tumor-associated antigens selected from the group consisting of HLA-A24, FLJ14668, Cardiolipin, NNAT, SELS, HIGD2A, SSR3 and NRP2. In some embodiments, the population of genetically modified cells are autologous. In some embodiments, the population of genetically modified cells are allogeneic. In some embodiments, the population of genetically modified cells are bystander cells.

In yet another approach, two different populations of cells are genetically modified to express the coding sequence for a cytokine and one or more prostate tumor-associated antigens selected from the group consisting of HLA-A24, FLJ14668, Cardiolipin, NNAT, SELS, HIGD2A, SSR3 and NRP2. In some embodiments, one of the populations of genetically modified cells are autologous. In some embodiments, one of the populations of genetically modified cells are allogeneic. In some embodiments, one of the population of genetically modified cells are bystander cells. In some embodiments of the compositions described herein, a first population of cells comprise tumor cells genetically modified to express the coding sequence or a cytokine, and a second population of cells comprise bystander cells genetically modified to express the coding sequence for one or more prostate tumor-associated antigens selected from the group consisting of HLA-A24, FLJ14668, Cardiolipin, NNAT, SELS, HIGD2A, SSR3 and NRP2. In some embodiments, the tumor cells are autologous cells. In some the embodiments, the tumor cells are allogeneic cells.

In certain embodiments, the methods of the invention utilize combination immunotherapies that comprise a cellular immunotherapy provided herein and one or more additional cancer therapeutic agents, e.g., agents that enhance anti-tumor immunity. Any cancer therapeutic agent known in the an may be combined with the cellular immunotherapy provided herein to induce or increase an immune response in a subject against one or more prostate tumor-associated antigens.

For example, recent studies suggest that PD-L1/PD-1 interaction plays a pivotal role in the immune evasion of tumors from the host immune system (Blank et al. *Cancer Immunol. Immunother.* 54(4):307-14 (2005)), and that blockade of PD-L1/PD-1 interaction, e.g., with an antibody which specifically binds PD-1, may serve as one possible mechanism for enhancing anti-tumor immunity. Accordingly, in one aspect of the invention, the invention provides a composition for cancer immunotherapy comprising an anti-PD-1 antibody and one or more populations of cells genetically modified to express the coding sequence for a cytokine and the coding sequence of one or more prostate tumor-associated antigens selected from the group consisting of HLA-A24, FLJ14668, Cardiolipin, NNAT, SELS. HIGD2A, SSR3 and NRP2. In some embodiments, the genetically modified cells are further modified to express the anti-PD-1 antibody. In another aspect of the invention, the invention provides a method for inducing or increasing an immune response in a subject against one or more prostate tumor-associated antigens, comprising administering a composition to a subject with prostate cancer, the composition comprising an anti-PD-1 antibody and one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the genetically modified cells are further modified to express the anti-PD-1 antibody. Methods of administering a cytokine-expressing cellular immunotherapy in combination with an anti-PD-1 antibody are described in U.S. patent application Ser. No. 12/178,122, the contents of which are incorporated by reference in their entireties.

In addition, anti-CTLA-4 blockade together with the use of GM-CSF-modified tumor cell vaccines has been shown to be effective in a number of experimental tumor models, such as mammary carcinoma (Hurwitz et al., *Proc Natl Acad Sci USA.* 95(17):10067-71 (1998)), primary prostate cancer (Hurwitz A. et al. (2000) Cancer Research 60 (9): 2444-8) and melanoma (van Elsas, A et al. (1999) J. Exp. Med. 190: 355-66). Accordingly, in one aspect of the invention, the invention provides a composition for cancer immunotherapy comprising an anti-CTLA-4 antibody and one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the genetically modified cells are further modified to express the anti-CTLA-4 antibody. In another aspect of the invention, the invention provides a method for inducing or increasing an immune response in a subject against one or more prostate tumor-associated antigens, comprising administering a composition to a subject with prostate cancer, the composition comprising an anti-CTLA-4 antibody and one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the genetically modified cells are further modified to express the anti-CTLA-4 antibody.

Additional cancer therapeutic agents that find use in combination with the cellular immunotherapies described herein include tyrosine kinase inhibitors. Administration of a cytokine-expressing cancer immunotherapy composition in combination with at least one tyrosine kinase inhibitor results in enhanced immunotherapeutic potency, i.e., an increase in the number and/or proliferation of activated T-cells, relative to administration of either the cytokine-expressing cancer immunotherapy composition or the tyrosine kinase inhibitor alone. See, e.g., U.S. Patent Application Publication No. 2007/0231298, the contents of which are incorporated by reference in their entireties. Accordingly, in one aspect of the invention, the invention provides a composition for cancer immunotherapy comprising a tyrosine kinase inhibitor and one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the tyrosine kinase inhibitor is selected from the group consisting of gefitimib, erolotinib and imatinib. In another aspect of the invention, the invention provides a method for inducing or increasing an immune response in a subject against one or more prostate tumor-associated antigens, comprising administering a composition to a subject with prostate cancer, the composition comprising a tyrosine kinase inhibitor and one or more populations of cells genetically modified to express the coding sequence for a cytokine and the coding sequence of one or more prostate tumor-associated antigens selected from the group consisting of HLA-A24, FLJ14668, Cardiolipin, NNAT, SELS, HIGD2A, SSR3 and NRP2. In some embodiments, the tyrosine kinase inhibitor is selected from the group consisting of gefitimib, erolotinib and imatinib. Methods of administering a cytokine-expressing cellular immunotherapy in combination with a tyrosine kinase inhibitor are described in U.S. Patent Application Publication No. 2007/0231298, the contents of which are incorporated by reference in their entireties.

5.4 Immunogenic Compositions Comprising Cells Expressing a Cytokine and One or More Prostate Tumor-associated Antigens 5.4.1. Introduction of Cytokine and Prostate Tumor-Associated Antigen into Cells In one aspect of the invention, a nucleic acid sequence (i.e., a recombinant DNA construct or vector) encoding a cytokine or a tumor antigen operably linked to a promoter is introduced into a cell or population of cells. In some embodiments, the nucleic acid sequence may encode both a cytokine and a tumor antigen, each operably linked to a promoter yet independently transcribed from the same nucleic acid sequence. In other embodiments, the nucleic acid sequence may encode more than one tumor antigen, each operably linked to a promoter yet independently transcribed from the same nucleic acid sequence. In yet other embodiments, the nucleic acid sequence may encode both a cytokine and a tumor antigen, or more than one tumor antigen, from the same promoter by utilizing an expression vector that is capable of producing polycistronic or mRNA. Within these embodiments, certain internal ribosome entry site (IRES) sequences may be utilized to allow for expression of a polycistronic message comprising the coding sequence for a cytokine and a tumor antigen, or one or more tumor antigens. Preferred IRES elements include, but are not limited to the mammalian BiP IRES and the hepatitis C virus IRES.

Any and all methods of introduction into a cell or population of cells, typically tumor cells, are contemplated according to the invention. The method is not dependent on any particular means of introduction and is not to be so construed.

The "vector" may be a DNA molecule such as a plasmid, virus or other vehicle, which contains one or more heterologous or recombinant DNA sequences, e.g., a nucleic acid sequence encoding a cytokine and/or a tumor antigen under the control of a functional promoter and in some cases further including an enhancer that is capable of functioning as a vector, as understood by those of ordinary skill in the art. An appropriate viral vector includes, but is not limited to, a retrovirus, a lentivirus, an adenovirus (AV), an adeno-associated virus (AAV), a simian virus 40 (SV-40), a bovine papilloma virus, an Epstein-Barr virus, a herpes virus, a vaccinia virus, a Moloney murine leukemia virus, a Harvey murine sarcoma virus, a murine mammary tumor virus, and a Rous sarcoma virus. Non-viral vectors are also included within the scope of the invention.

Any suitable vector can be employed that is appropriate for introduction of nucleic acids into eukaryotic tumor cells, or more particularly animal tumor cells, such as mammalian, e.g., human, tumor cells. Preferably the vector is compatible with the tumor cell, e.g., is capable of imparting expression of the coding sequence for a cytokine and/or tumor antigen and is stably maintained or relatively stably maintained in the tumor cell. Desirably, the vector comprises an origin of replication and the vector may or may not also comprise a "marker" or "selectable marker" function by which the vector can be identified and selected. While any selectable marker can be used, selectable markers for use in such expression vectors are generally known in the art and the choice of the proper selectable marker will depend on the host cell. Examples of selectable marker genes which encode proteins that confer resistance to antibiotics or other toxins include ampicillin, methotrexate, tetracycline, neomycin (Southern and Berg. J., 1982), myco-phenolic acid (Mulligan and Berg, 1980), puromycin, zeo-mycin, hygromycin (Sugden et al., 1985) or G418.

In practicing the methods of the present invention, a vector comprising a nucleic acid sequence encoding a cytokine and/or a tumor antigen may be transferred to a cell in vitro, preferably a tumor cell, using any of a number of methods which include but are not limited to electroporation, membrane fusion with liposomes. Lipofectamine treatment, high velocity bombardment with DNA-coated microprojectiles, incubation with calcium phosphate-DNA precipitate, DEAE-dextran mediated transfection, infection with modified viral nucleic acids, direct microinjection into single cells, etc. Procedures for the cloning and expression of modified forms of a native protein using recombinant DNA technology are generally known in the art, as described in Ausubel, et al., 2007 and Sambrook, et at, 2002, expressly incorporated by reference, herein.

Reference to a vector or other DNA sequence as "recombinant" merely acknowledges the operable linkage of DNA sequences which are not typically operably linked as isolated from or found in nature. A "promoter" is a DNA sequence that directs the binding of RNA polymerase and thereby promotes RNA synthesis. "Enhancers" are cis-acting elements that stimulate or inhibit transcription of adjacent genes. An enhancer that inhibits transcription also is termed a "silencer." Enhancers can function (i.e. be operably linked to a coding sequence) in either orientation, over distances of tip to several kilobase pairs (kb) from the coding sequence and from a position downstream of a transcribed region. Regulatory (expression/control) sequences are operatively linked to a nucleic acid coding sequence when the expression/control sequences regulate the transcription and, as appropriate, translation of the nucleic acid sequence. Thus, expression/control sequences can include promoters, enhancers, transcription terminators, a start codon (i.e., ATG) in front of the coding sequence, a splicing signal for introns, and stop codons.

Recombinant vectors for the production of cellular immunotherapies of the invention provide the proper transcription, translation and processing signals (e.g., splicing and polyadenylation signals) such that the coding sequence for the cytokine and/or tumor antigen is appropriately transcribed and translated in the tumor cells into which the vector is introduced. The manipulation of such signals to ensure appropriate expression in host cells is within the skill of the ordinary skilled artisan. The coding sequence for the cytokine and/or the tumor antigen may be under the control of (i.e., operably linked to) its own native promoter, or a non-native (e.g. heterologous) promoter, including a constitutive promoter, e.g., the cytomegalovirus (CMV) immediate early promoter/enhancer, the Rous sarcoma virus long terminal repeat (RSV-LTR) or the SV-40 promoter.

Alternately, a tissue-specific promoter (a promoter that is preferentially activated in a particular type of tissue and results in expression of a gene product in that tissue) can be used in the vector. Such promoters include but are not limited to a liver specific promoter (Ill C R, et al., Blood Coagul Fibrinolysis 8 Suppl 2:S23-30, 1997) and the EF-1 alpha promoter (Kim D W et al. Gene. 91(2):217-23, 1990, Guo Z S et al. Gene Ther. 3(9):802-10, 1996; U.S. Pat. Nos. 5,266,491 and 5,225,348, each of which expressly incorporated by reference herein). Inducible promoters also find utility in practicing the methods described herein, such as a promoter containing the tet responsive element (TRE) in the tet-on or tet-off system as described (ClonTech and BASF), the metallothienein promoter which can be upregulated by addition of certain metal salts and rapamycin inducible promoters (Rivera et al., 1996, Nature Med. 2(9): 1028-1032: Ye et al. 2000, Science 283: 88-91; Sawyer T K et al., 2002, Mini Rev Med Chem. 2(5):475-88). Large numbers of suitable tissue-specific or regulatable vectors and promoters for use in practicing the current invention are known to those of skill in the art and many are commercially available.

Exemplary vector systems for use in practicing the invention include the retroviral MFG vector, described in U.S. Pat. No. 5,637,483, expressly incorporated by reference herein. Other useful retroviral vectors include pLJ, pEm and [alpha]SGC, described in U.S. Pat. No. 5,637,483 (in particular Example 12), U.S. Pat. Nos. 6,506,604, 5,955,331 and U.S. Ser. No. 09/612,808, each of which is expressly incorporated by reference herein.

Further exemplary vector systems for use in practicing the invention include second, third and fourth generation lentiviral vectors, U.S. Pat. Nos. 6,428,953, 5,665,577 and 5,981,276 and WO 00/72686, each of which is expressly incorporated by reference herein.

Additional exemplary vector systems for use in practicing the present invention include adenoviral vectors, described for example in U.S. Pat. No. 5,872,005 and international Patent Publication No. WO 00/72686, each of which is expressly incorporated by reference herein.

Yet another vector system that is preferred in practicing the methods described herein is a recombinant adeno-associated vector (rAAV) system, described for example in International Patent Publication Nos. WO 98/46728 and WO 00/72686, Samulski et al., Virol. 63:3822-3828 (1989) and U.S. Pat. Nos. 5,436,146, 5,753,500, 6,037,177, 6,040,183 and 6,093,570, each of which is expressly incorporated by reference herein.

In one preferred embodiment, one or more viral or non-viral vectors are utilized to deliver a cytokine, e.g., human GM-CSF transgene (coding sequence), and one or more prostate tumor-associated antigen (coding sequence) to a human tumor cell ex vivo. After transduction, the cells are irradiated to render them proliferation incompetent. The proliferation incompetent cytokine, e.g., GM-CSF and tumor antigen expressing tumor cells are then re-administered to the patient (e.g., by the intradermal or subcutaneous route) and thereby function as a cancer vaccine. The human tumor cell may be a primary tumor cell or derived from a tumor cell line.

In general, the genetically modified tumor cells include one or more of autologous tumor cells, allogeneic tumor cells and tumor cell lines (i.e., bystander cells). The tumor cells may be transduced in vitro, ex vivo or in vivo. Autologous and allogeneic cancer cells that have been genetically modified to express a cytokine. e.g., GM-CSF, followed by readministration to a patient for the treatment of cancer are described in U.S. Pat. Nos. 5,637,483, 5,904,920 and 6,350,445, expressly incorporated by reference herein. A form of GM-CSF-expressing genetically modified tumor cells or a "cytokine-expressing cellular vaccine" ("GVAX"®), for the treatment of pancreatic cancer is described in U.S. Pat. Nos. 6,033,674 and 5,985,290, expressly incorporated by reference herein. A universal immunomodulatory genetically modified bystander cell line is described in U.S. Pat. No. 6,464,973, expressly incorporated by reference herein.

An allogeneic form of GVAX® wherein the cellular vaccine comprises one or more prostate tumor cell lines selected from the group consisting of DU 145, PC-3, and LNCaP is described in WO/0026676, expressly incorporated by reference herein. LNCaP is a PSA-producing prostate tumor cell line, while PC-3 and DU-145 are non-PSA-producing prostate tumor cell lines (Pang S. et al. Hum Gene Ther. 1995 November; 6(1):1417-1426).

Clinical trials employing GM-CSF-expressing cellular vaccines (GVAX®) have been undertaken for treatment of prostate cancer, melanoma, lung cancer, pancreatic cancer, renal cancer, and multiple myeloma. A number of clinical trials using GVAX® cellular vaccines have been described, most notably in melanoma, and prostate, renal and pancreatic carcinoma (Simons J W et al. Cancer Res. 1999; 59:5160-5168; Simons J W et al. Cancer Res 1997; 57:1537-1546; Soiffer R et al. Proc. Natl. Acad. Sci USA 1998; 95:13141-13146; Jaffee, et al. J Clin Oncol 2001; 19:145-156; Salgia et al. J Clin Oncol 2003 21:624-30; Soiffer et al. J Clin Oncol 2003 21:3343-50; Nemunaitis et al. J Natl Cancer Inst. 2004 Feb. 18 96(4):326-31).

By way of example, in one approach, one or more prostate tumor-associated tumor antigens described herein are expressed by an allogeneic or bystander cell line while a cytokine (e.g., GM-CSF) is expressed by autologous or allogeneic cells. The GM-CSF coding sequence is introduced into the tumor cells using a viral or non-viral vector and routine methods commonly employed by those of skill in the art. The preferred coding sequence for GM-CSF is the genomic sequence described in Huebner K. et al., Science 230(4731): 1282-5, 1985, however, in some cases the cDNA form of GM-CSF finds utility in practicing the methods (Cantrell et al., Proc. Natl. Acad. Sci., 82, 6250-6254, 1985).

In one aspect of the invention, the invention provides a method of making a cellular immunotherapy composition, comprising obtaining one or more population of cells and modifying the one or more population of cells by introducing into the cells: (i) a nucleic acid molecule comprising a nucleic acid sequence encoding a cytokine operably linked to a promoter, (ii) one or more nucleic acid molecules comprising a nucleic acid sequence encoding a prostate tumor-associated antigen selected from the group consisting HLA-A24, FLJ14668, Cardiolipin, NNAT, SELS, HIGD2A, SSR3 and NRP2; and (iii) a nucleic acid molecule comprising a nucleic acid sequence encoding a selectable marker operably linked to a promoter. In a particular embodiment, the cytokine is GM-CSF. The nucleic acid molecule comprising a nucleic acid sequence encoding a cytokine operably linked to a promoter, and the one or more nucleic acid molecules comprising a nucleic acid sequence encoding one or more prostate tumor-associated antigens, can be any nucleic acid molecule suitable for gene transfer as described above. While any selectable marker can be used, in particular embodiments, the selectable marker is an antibiotic resistance gene, such as hygromycin resistance. In some embodiments, a genetically modified mammalian, preferably human cell line is cultured in culture medium comprising at least 400 μg hygromycin/ml culture medium.

5.4.2. Administration

The genetically modified tumor cells can be cryopreserved prior to administration. Preferably, the genetically modified tumor cells are irradiated at a dose of from about 50 to about 200 rads/min, even more preferably, from about 120 to about 140 rads/min prior to administration to the patient. Preferably, the cells are irradiated with a total dose sufficient to inhibit substantially 100% of the cells from further proliferation. Thus, desirably the cells are irradiated with a total dose of from about 10,000 to 20,000 rads, optimally, with about 15,000 rads. Typically more than one administration of cytokine (e.g., GM-CSF) and prostate tumor-associated antigen producing cells is delivered to the subject in a course of treatment. Dependent upon the particular course of treatment, multiple injections may be given at a single time point with the treatment repeated at various time intervals. For example, an initial or "priming" treatment may be followed by one or more "booster" treatments. Such "priming" and "booster" treatments are typically delivered by the same route of administration and/or at about the same site. When multiple doses are administered, the first immunization dose may be higher than subsequent immunization doses. For example, a $5 \times 10^6$ prime dose may be followed by several booster doses of $10^6$ to $3 \times 10^6$ GM-CSF and tumor antigen producing cells.

A single injection of cytokine and tumor antigen producing cells is typically between about $10^6$ to $10^8$ cells, e.g., $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $10^7$, $2 \times 10^7$, $5 \times 10^7$, or as many as $10^8$ cells. In one embodiment, there are between $10^6$ and $10^8$ cytokine-producing cells per unit dose. The number of cytokine and tumor antigen producing cells may be adjusted according, for example, to the level of cytokine and/or tumor antigen produced by a given cellular immunotherapy composition.

In some embodiments, cytokine-producing cells of the cellular immunotherapy are administered in a dose that is capable of producing at least 500 ng of GM-CSF per 24 hours per one million cells, in some embodiments, prostate tumor associated-tumor antigen-producing cells of the cellular immunotherapy are administered in a dose that is capable of producing at least 500 ng of the particular tumor antigen per 24 hours per one million cells. Determination of optimal cell dosage and ratios is a matter of routine determination and within the skill of a practitioner of ordinary skill, in light of the disclosure provided herein.

In treating a prostate cancer patient according to the methods described herein, the attending physician may administer lower doses of the cellular immunotherapy composition and observe the patient's response. Larger doses of the cellular immunotherapy may be administered until the an improved therapeutic outcome is evident.

Cytokine and tumor antigen expressing cells of the cellular immunotherapy of the invention are processed to remove most additional components used in preparing the cells. In particular, fetal calf serum, bovine serum components, or other biological supplements in the culture medium are removed. In one embodiment, the cells are washed, such as by repeated gentle centrifugation, into a suitable pharmacologically compatible excipient. Compatible excipients include various cell culture media, isotonic saline, with or without a physiologically compatible buffer, for example, phosphate or hepes, and nutrients such as dextrose, physiologically compatible ions, or amino acids, particularly those devoid of other immunogenic components.

A composition for administration in vivo can comprise appropriate carriers or diluents, which further can be pharmaceutically acceptable. For example, carrying reagents, such as albumin and blood plasma fractions and inactive thickening agents, may be used. The means of making such a composition have been described in the art. See, e.g., Remington's Pharmaceutical Sciences 19th edition, Genarro, A. Ed. (1995).

In pharmaceutical dosage form, the cellular immunotherapy composition described herein can be used alone or in appropriate association, as well as in combination, with other pharmaceutically active compounds as are known in the art.

5.4.3. Autologous Cells

The use of autologous genetically modified cells expressing a cytokine, e.g. GM-CSF and one or more prostate tumor-associated tumor antigens provides advantages since each patient's tumor expresses a unique set of tumor antigens that can differ from those found on histologically-similar, MHC-matched tumor cells from another patient. See. e.g., Kawakami et al., J. Immunol., 148, 638-643 (1992); Darrow et al., J. Immunol., 142, 3329-3335 (1989); and Horm et al. J. Immunother., 10, 153-164 (991). In contrast, MHC-matched tumor cells provide the advantage that the patient need not be taken to surgery to obtain a sample of their tumor for genetically modified tumor cell production.

In one preferred aspect, the method of treating prostate cancer comprises: (a) obtaining tumor cells from a mammalian subject harboring a prostate tumor; (b) genetically modifying the tumor cells to render them capable of producing an increased level of GM-CSF and one or more prostate tumor-associated antigens relative to unmodified tumor cells; (c) rendering the modified tumor cells proliferation incompetent; and (d) readministering the genetically modified tumor cells to the mammalian subject from which the tumor cells were obtained or to a mammal with the same MHC type as the mammal from which the tumor cells were obtained. The administered tumor cells are autologous and MHC-matched to the host. Preferably, the composition is administered intradermally, subcutaneously or intratumorally to the mammalian subject.

In some cases, a single autologous tumor cell may express GM-CSF alone or GM-CSF plus one or more prostate tumor-associated antigens. In other cases, GM-CSF and the one or more prostate tumor-associated antigens may be expressed by different autologous tumor cells. In one aspect of the invention, an autologous tumor cell is modified by introduction of a vector comprising a nucleic acid sequence encoding GM-CSF, operatively linked to a promoter and expression/control sequences necessary for expression thereof. In another aspect, the same autologous tumor cell or a second autologous tumor cell can be modified by introduction of a vector comprising a nucleic acid sequence encoding one or more prostate tumor-associated antigens operatively linked to a promoter and expression/control sequences necessary for expression thereof. The nucleic acid sequence encoding the one or more prostate tumor-associated antigens can be introduced into the same or a different autologous tumor cell using the same or a different vector. The nucleic acid sequence encoding the one or more prostate rumor-associated antigens may or may not further comprise a selectable marker sequence operatively linked to a promoter. Desirably, the autologous tumor cell expresses high levels of GM-CSF and/or the one or more prostate tumor-associated antigens.

5.4.4. Allogeneic Cells

Researchers have sought alternatives to autologous and MHC-matched cells as tumor vaccines, as reviewed by Jaffee et al., Seminars in Oncology, 22, 81-91 (1995). Early tumor vaccine strategies were based on the understanding that the vaccinating cells function as the antigen presenting cells (APCs) that present tumor antigens on their MHC class I and II molecules, and directly activate the T cell arm of the immune system. The results of Huang et al. (Science, 264, 961-965, 1994), indicate that professional APCs of the host rather than the vaccinating cells prime the T cell arm of the immune system by secreting cytokine(s) such as GM-CSF such that bone marrow-derived APCs are recruited to the region of the tumor. The bone marrow-derived APCs take up the whole cellular protein of the tumor for processing, and then present the antigenic peptide(s) on their MHC class I and II molecules, thereby priming both the CD4+ and the CD8+T cell arms of the immune system, resulting in a systemic tumor-specific anti-tumor immune response. Without being bound by theory, these results suggest that it may not be necessary or optimal to use autologous or MHC-matched cells in order to elicit an anti-cancer immune response and that the transfer of allogeneic MHC genes (from a genetically dissimilar individual of the same species) can enhance tumor immunogenicity. More specifically, in certain cases, the rejection of tumors expressing allogeneic MHC class I molecules has resulted in enhanced systemic immune responses against subsequent challenge with the unmodified parental tumor. See, e.g., Jaffee et al., supra, and Huang et al., supra.

As used herein, a "tumor cell line" comprises cells that were initially derived from a tumor. Such cells typically exhibit indefinite growth in culture. In one aspect, the method for treating prostate cancer comprises: (a) obtaining a tumor cell line; (b) genetically modifying the tumor cell line to render the cells capable of producing an increased level of a cytokine, e.g., GM-CSF, and one or more prostate tumor-associated antigens relative to the unmodified tumor cell line: (c) rendering the modified tumor cell line proliferation incompetent; and (d) administering the tumor cell line to a mammalian subject (host) having at least one tumor that is of the same type of tumor as that from which the tumor cell line was obtained. In some embodiments, the administered tumor cell line is allogeneic and is not MHC-matched to the host. Such allogeneic lines provide the advantage that they can be prepared in advance, characterized, aliquoted in vials containing known numbers of transgene (e.g., GM-CSF) expressing cells and stored (i.e. frozen) such that well characterized cells are available for administration to the patient. Methods for the production of genetically modified allogeneic cells are described for example in WO 00/72686, expressly incorporated by reference herein.

In one approach to preparing genetically modified allogeneic cells, a nucleic acid sequence (transgene) encoding GM-CSF alone or in combination with the nucleic acid coding sequence for one or more prostate tumor-associated antigens is introduced into a cell line that is an allogeneic tumor cell line (i.e., derived from an individual other than the individual being treated). In another approach, a nucleic acid sequence (transgene) encoding GM-CSF alone or in combination with the nucleic acid coding sequence for one or more prostate tumor-associated antigens is introduced into separate allogeneic tumor cell lines. In yet another approach two or more different genetically modified allogeneic cell lines (e.g. LNCAP and PC-3) expressing GM-CSF and one or more prostate tumor-associated antigens are administered in combination, typically at a ratio of 1:1. In general, the cell or population of cells is from a tumor cell line of the same type as the tumor or cancer being treated, e.g. prostate cancer. The nucleic acid sequence encoding the prostate tumor-associated antigens may be introduced into the same or a different allogeneic tumor cell using the same or a different vector. The nucleic acid sequence encoding the prostate tumor-associated antigens (s) may or may not further comprise a selectable marker sequence operatively linked to a promoter. Desirably, the allogeneic cell line expresses high levels of GM-CSF and/or the one or more prostate tumor-associated antigens.

In another aspect, one or more genetically modified GM-CSF expressing allogeneic cell lines can be exposed to an antigen, e.g. a prostate tumor-associated antigen, such that the patient's immune response to the antigen is increased in the presence of GM-CSF, e.g., an allogeneic or bystander cell that has been genetically modified to express GM-CSF. Such exposure may take place ex vivo or in vivo. In one preferred embodiment, the antigen is a peptide comprising an amino acid sequence obtained from HLA-A24, FLJ14668, Cardiolipin, NNAT, SELS. HIGD2A, SSR3 or NRP2, as described extensively above. In such cases, the composition can be rendered proliferation-incompetent, typically by irradiation, wherein the allogeneic cells are plated in a tissue culture plate and irradiated at room temperature using a Cs source, as further described herein. An allogeneic cellular vaccine composition of the invention may comprise allogeneic cells plus other cells, i.e. a different type of allogeneic cell, an autologous cell, or a bystander cell that may or may not be genetically modified. If genetically modified, the different type of allogeneic cell, autologous cell, or bystander cell may express GM-CSF and/or one or more prostate tumor-associated antigens. The ratio of allogeneic cells to other cells in a given administration will vary dependent upon the combination.

Any suitable route of administration can be used to introduce an allogeneic cell line composition into the patient, preferably, the composition is administered intradermally, subcutaneously or intratumorally.

5.4.5. Bystander Cells

In one further aspect, a universal immunomodulatory genetically modified transgene-expressing bystander cell that expresses at least one transgene, e.g. a nucleic acid sequence encoding a cytokine, e.g. GM-CSF, or a prostate tumor-associated antigen, can be used in the immunotherapies described herein. The same universal bystander cell line may express more than one transgene or individual transgenes may be expressed by different universal bystander cell lines. The universal bystander cell line comprises cells which either naturally lack major histocompatibility class I (MHC-I) antigens and major histocompatibility class II (MHC-II) antigens or have been modified so that they lack MHC-I antigens and MHC-II antigens. In one aspect, a universal bystander cell line can be modified by introduction of a vector wherein the vector comprises a nucleic acid sequence encoding a transgene, e.g., a cytokine such as GM-CSF, and/or one or more prostate tumor-associated antigens, operably linked to a promoter and expression control sequences necessary for expression thereof. In another aspect, the same universal bystander cell line or a second a universal bystander cell line is modified by introduction of a vector comprising a nucleic acid sequence encoding at least one additional transgene, e.g., a cytokine such as GM-CSF, and/or one or more prostate tumor-associated antigens, operatively linked to a promoter and expression control sequences necessary for expression thereof. The nucleic acid sequence encoding the transgene(s) may be introduced into the same or a different universal bystander cell line using the same or a different vector. The nucleic acid sequence encoding the transgene(s) may or may not further comprise a selectable marker sequence operatively linked to a promoter. Any combination of transgene(s) that stimulate an anti-tumor immune response can be used. The universal bystander cell line preferably grows in defined, i.e., serum-free medium, preferably as a suspension.

An example of a preferred universal bystander cell line is K562 (ATCC CCL-243; Lozzio et al., Blood 45(3): 321-334 (1975); Klein er al., Int. J. Cancer 18: 421-431 (1976)). A detailed description of the generation of human bystander cell lines is described for example in U.S. Pat. No. 6,464, 973, expressly incorporated by reference herein.

Desirably, the universal bystander cell line expresses high levels of the transgene, e.g. a cytokine such as GM-CSF and/or one or more prostate tumor-associated antigens.

In the methods provided herein, the one or more universal bystander cell lines can be incubated with an autologous cancer antigen, e.g., provided by an autologous tumor cell (which together comprise a universal bystander cell line composition), then the universal bystander cell line composition can be administered to the patient. Any suitable route of administration can be used to introduce a universal bystander cell line composition into the patient. Preferably, the composition is administered intradermally, subcutaneously or intratumorally.

Typically, the autologous cancer antigen can be provided by a cell of the cancer to be treated, i.e., an autologous cancer cell. In such cases, the composition is rendered proliferation-incompetent by irradiation, wherein the bystander cells and cancer cells are plated in a tissue culture plate and irradiated at room temperature using a Cs source, as detailed above.

The ratio of bystander cells to autologous cancer cells in a given administration will vary dependent upon the combination. With respect to GM-CSF-producing bystander cells, the ratio of bystander cells to autologous cancer cells in a given administration should be such that a therapeutically effective level of GM-CSF is produced. In addition to the GM-CSF threshold, the ratio of bystander cells to autologous cancer cells should not be greater than 1:1. Appropriate ratios of bystander cells to tumor cells or tumor antigens can be determined using routine methods known in the art.

Typically a minimum dose of about 3500 rads is sufficient to inactivate a cell and render it proliferation-incompetent, although doses up to about 30,000 rads are acceptable. In some embodiments, the cells are irradiated at a dose of from about 50 to about 200 rads/min or from about 120 to about 140 rads/min prior to administration to the mammal. Typically, when using irradiation, the levels required are 2,500 rads, 5,000 rads, 10,000 rads, 15,000 rads or 20,000 rads. In one embodiment, a dose of about 10,000 rads is used to inactivate a cell and render it proliferation-incompetent. It is understood that irradiation is but one way to render cells proliferation-incompetent, and that other methods of inactivation which result in cells incapable of multiple rounds of cell division but that retain the ability to express transgenes (e.g. cytokines and/or tumor antigens) are included in the present invention (e.g., treatment with mitomycin C, cycloheximide, and conceptually analogous agents, or incorporation of a suicide gene by the cell).

5.4.6. Cytokines

A "cytokine" or grammatical equivalent, includes, without limitation, those hormones that act locally and do not circulate in the blood, and which, when used in accordance with the present invention, will result in an alteration of an individual's immune response. Also included in the definition of cytokine are adhesion or accessory molecules which result in an alteration of an individual's immune response. Thus, examples of cytokines include, but are not limited to, interferon alpha (IFN-α), interferon beta (IFN-β), interferon gamma (IFN-γ), interleukin-1 (IL-1), IL-2, IL-3, IL-4, IL-5, IL-6, IL-7, IL-8, IL-9, IL-10, IL-11, IL-12, tumor necrosis factor alpha (TNF-α), tumor necrosis factor beta (TNF-β), erythropoietin (EPO), MIP3A, intracellular adhesion molecule (ICAM), macrophage colony stimulating factor (M-CSF), granulocyte colony stimulating factor (GCSF), granulocyte-macrophage colony stimulating factor (GM-CSF), LIF, LT, TGF-P, a-EFN, P-IFN, BCGF, and CD2. Descriptions of the aforementioned cytokines as well as other applicable immunomodulatory agents may be found in "Cytokines and Cytokine Receptors," A. S. Hamblin, D. Male (ed.), Oxford University Press, New York, N.Y. (1993)), or the "Guidebook to Cytokines and Their Receptors," N. A. Nicola (ed.), Oxford University Press, New York, N.Y. (1995)). Where therapeutic use in humans is contemplated, the cytokines will preferably be substantially similar to the human form of the protein or will have been derived from human sequences (i.e., of human origin). In one preferred embodiment, the cytokine of the cellular immunotherapy described herein is GM-CSF.

Additionally, cytokines of other mammals with substantial structural homology and/or amino acid sequence identity to the human forms of a given cytokine, will be useful when demonstrated to exhibit similar activity on the human immune system. Similarly, proteins that are substantially analogous to any particular cytokine, but have conservative changes of protein sequence, can also be used. Thus, conservative substitutions in protein sequence may be possible without disturbing the functional abilities of the protein molecule, and thus proteins can be made that function as cytokines in the present invention but have amino acid sequences that differ slightly from currently known sequences. Such conservative substitutions typically include substitutions within the following groups: glycine, alanine; valine, isoleucine, leucine; aspartic acid, glutamic acid, asparagine, glutamine; serine, threonine: lysine, arginine; and phenylalanine, tyrosine.

Granulocyte-macrophage colony stimulating factor (GM-CSF) is a cytokine produced by fibroblasts, endothelial cells, T cells and macrophages. This cytokine has been shown to induce the growth of hematopoetic cells of granulocyte and macrophage lineages. In addition, it also activates the antigen processing and presenting function of dendritic cells, which are the major antigen presenting cells (APC) of the immune system. Results from animal model experiments have convincingly shown that GM-CSF producing cells are able to induce an immune response against parental, non-transduced cells.

GM-CSF augments the antigen presentation capability of the subclass of dendritic cells (DC) capable of stimulating robust anti-tumor responses (Gasson et al. Blood 1991 Mar. 15; 77(6):1131-45; Mach et al. Cancer Res. 2000 Jun. 15; 60(12):3239-46; reviewed in Mach and Dranuff, Curr Opin Immunol, 2000) October; 12(5):571-5). See. e.g., Boon and Old, Curr Opin Immunol. 1997 Oct. 1; 9(5):681-3). Presentation of tumor antigen epitopes to T cells in the draining lymph nodes is expected to result in systemic immune responses to tumor metastases. Also, irradiated tumor cells expressing GM-CSF have been shown to function as potent vaccines against tumor challenge. Localized high concentrations of certain cytokines, delivered by genetically modified cells, have been found to lead to tumor regression (Abe et al. J. Cane. Res. Clin. Oncol. 121: 587-592 (1995); Gansacher et al., Cancer Res. 50: 7820-7825 (1990); Formi et al., Cancer and Met. Reviews 7: 289-309 (1988), PCT publication WO200072686 describes tumor cells expressing various cytokines.

In one embodiment, the cellular immunogenic composition comprises a GM-CSF coding sequence operatively linked to regulatory elements for expression in the cells of the vaccine. The GM-CSF coding sequence may code for a murine or human GM-C(SF and may be in the form of genomic DNA (SEQ ID NO: 15; disclosed as SEQ ID NO: NO.: 1 in US Patent Publication NO. 2006/0057127, which is hereby incorporated by reference in its entirety) or cDNA (SEQ ID NO: 16; disclosed as SEQ ID NO: NO.: 2 in US Patent Publication NO. 2006/0057127, which is hereby incorporated by reference in its entirety). In the case of cDNA, the coding sequence for GM-CSF does not contain intronic sequences to be spliced out prior to translation. In contrast, for genomic GM-CSF, the coding sequence contains at least one native GM-CSF intron that is spliced out prior to translation. In one embodiment, the GM-CSF coding sequence encodes the amino acid sequence presented as SEQ ID NO.: 17 (disclosed as SEQ ID NO.:3 in US Patent Publication NO. 2006/0057127, which is hereby incorporated by reference in its entirety). Other examples of GM-CSF coding sequences are found in Genbank accession numbers: AF373868, AC034228, AC034216, M 10663 and NM000758.

A GM-CSF coding sequence can be a full-length complement that hybridizes to the sequence shown in SEQ ID NO: 15 or SEQ ID NO: 16 under stringent conditions. The phrase "hybridizing to" refers to the binding, duplexing, or hybridizing of a molecule to a particular nucleotide sequence under stringent conditions when that sequence is present in a complex mixture (e.g., total cellular) DNA or RNA. "Bind (s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

It therefore follows that the coding sequence for a cytokine such as GM-CSF. CSF, can have at least 80, 85, 87, 89, 90, 90, 91, 92, 93, 94, 95, 96, 97, 98, 99% or more % identity over its entire length to a native GM-CSF coding sequence. For example, a GM-CSF coding sequence can have at least 80, 85, 87, 89, 90, 91, 92, 93, 94, 95, 96, 97, 98, 99% or more sequence identity to a sequence presented as SEQ ID NO: NO: 15 or SEQ ID NO: NO: 16, when compared and aligned for maximum correspondence, as measured a sequence comparison algorithm (as described above) or by visual inspection. In one embodiment, the given % sequence identity exists over a region of the sequences that is at least about 50 nucleotides in length. In another embodiment, the given % sequence identity exists over a region of at least about 100 nucleotides in length. In another embodiment, the given % sequence identity exists over a region of at least about 200 nucleotides in length. In another embodiment, the given % sequence identity exists over the entire length of the sequence. Preferably, the GM-CSF has authentic GM-CSF activity, e.g., can bind the GM-CSF receptor.

In some embodiments, the amino acid sequence for a cytokine such as M-CSF has at least 80, 85, 87, 89, 90, 91, 92, 93, 94, 95, 96, 97, 98, 99% or more sequence identity to the sequence presented as SEQ ID NO: NO: 17, when compared and aligned for maximum correspondence.

5.4.7. Kits

The cellular immunotherapy compositions provided herein can be included in a kit, container, pack, or dispenser together with instructions for administration. When the composition is supplied as a kit, the different components of the composition may be packaged in separate containers so as to permit long-term storage without losing the active components' functions. The reagents included in the kits can be supplied in containers of any sort such that the life of the different components are preserved, and are not adsorbed or altered by the materials of the container. For example, cytokine-expressing and/or prostate tumor-associated antigen expressing cells may be housed in containers such as test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

Thus, in one aspect, the present invention provides a kit comprising a composition comprising a population of cells genetically modified to express the coding sequence for a cytokine and the coding sequence of one or more prostate tumor-associated antigens selected from the group consisting HLA-A24, FLJ14668, Cardiolipin, NNAT, SELS, HIGD2A, SSR3 and NRP2. In some embodiments, the genetically modified cells are autologous. In some embodiments, the genetically modified cells are allogeneic. In some embodiments, the genetically modified cells are bystander cells.

In another embodiment, the kit comprises a first composition comprising a population of cells genetically modified to express the coding sequence for a cytokine; and a second composition comprising a population of cells genetically modified to express the coding sequence of one or more prostate tumor-associated antigens selected from the group consisting of HLA-A24, FLJ14668, Cardiolipin, NNAT, SELS, HIGD2A, SSR3 and NRP2. In some embodiments, the first composition comprises a population of tumor cells and the second population comprises a population of bystander cells. In some embodiments, the tumor cells are autologous. In some embodiments, the tumor cells are allogeneic.

6. EXAMPLES

The present invention is described by reference to the following Examples, which are offered by way of illustration and are not intended to limit the invention in any manner. Standard techniques well known in the art or the techniques specifically described below are utilized. It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

Exemplary methods for producing recombinant viral vectors useful for making genetically altered tumor cells that express GM-CSF, methods for using the genetically altered tumor cells that express GM-CSF in cancer therapies, particularly prostate cancer therapies, are extensively described in U.S. Patent Application Publication No. 2006/0057127, incorporated by reference in its entirety, and will not be reproduced below. One such therapy that has been and is being evaluated in clinical trials for treatment of prostate cancer is GVAX® therapy.

6.1 Example 1: Identification of Protein Targets of Host Antibody Responses Following Cell-Based Prostate Cancer Immunotherapy This example describes identification of protein targets of host antibody responses following allogeneic cancer immunotherapy cells genetically modified to express GM-CSF.

Patients [n=19] treated with high-dose cell-based cancer immunotherapy (e.g., 500 million cells followed by 300 million cells every two weeks) demonstrate an increase in median survival time (MST). The median survival has not yet been reached for this high dose group, and the final median survival will be no less than 29.1 months based on the current median follow-up time for these patients. In addition, there was also a statistically significant increased antibody response to the cell-based cancer immunotherapy in the high dose group with detectable antibodies directed against antigens derived from the immunotherapy as determined by western blot analysis using patient sera harvested post-immunization.

Humoral patient immune responses to a cell-based prostate cancer immunotherapy have been evaluated to specifically identify which antigens may be specifically recognized by the patients' immune system following the therapy. Two differing methods have been used to characterize this response using patients' sera: i) serological analysis of gene expression libraries (SEREX) and ii) defined prostate cancer antigen screening. From these two techniques, multiple antibody responses to proteins derived from the immunotherapy have been identified that are specifically induced or augmented following immunization.

6.1.1. Serological Analysis of Gene Expression Libraries (SEREX)

SEREX allows the systematic cloning of tumor antigens recognized by the autoantibody repertoire of cancer patients (Sahin et al. 1995; McNeel et al. 2000; Wang et al. 2005; Dunphy et al. 2005; Qin et al. 2006). cDNA expression libraries were constructed from the tumor cell lines used to comprise the GVAX® immunotherapy (PC-3 and LNCaP prostate cancer cell lines modified to secrete GM-CSF), packaged into lambda-phage vectors, and expressed recombinantly in E. coli. Recombinant proteins expressed during the lytic infection of bacteria were then blotted onto nitrocellulose membranes and probed with diluted patient serum for identification of clones reactive with high-titered IgG antibodies.

This procedure was carried out for 8 patients treated with cell-based prostate cancer immunotherapy. These patients were prioritized for SEREX analysis based upon survival advantage. Survival advantage was determined by comparing individual patient survival time to a patient's predicted survival. Predicted survival was calculated using a published, validated nomogram based on seven prognostic variables including PSA, ECOG performance status, Gleason score sum, alkaline phosphatase, hemoglobin, LDH and presence/absence of visceral metastatic disease (Halabi, et al. 2003). From the SEREX analysis of these 8 patients, multiple LNCaP/PC-3 derived cell protein clones reactive to the patient sera post-immunotherapy were identified. Positive hits for the SEREX screen were then screened against pre-immunotherapy serum to determine if the antibody response to these proteins was augmented or induced following the immunotherapy.

For example, from patient 1, 24 proteins from an original list of 92 individual proteins (26%) have antibody responses that were induced upon GVAX® immunotherapy. The remainder of the responses (68 proteins) did not demonstrate an increase in titer. For patient 2, 18 individual proteins from a total of 47 (38%) had induced antibody titers following immunotherapy. For patient 3, 14/38 (37%) of antibody responses were induced following immunotherapy. Table 1, below, provides a compiled list of induced antibody hits (143 proteins total) for all 8 patients screened by SEREX.

TABLE 1

| Hit pulled out using what post serum? | X# | Plugs Came From Which Lib? | Gene |
|---|---|---|---|
| Patient 1 | X1 | L, L, L | ACAT2 (acetyl-Coenzyme A acetyltransferase 2) |
|  | X2 | P, P | ACAA1 |
|  | X3 | P | cDNA FLJ41756 fis |
|  | X4 | gP | cDNA: FLJ22465 fis |
|  | X5 | P, P | chromosome 20 open reading frame 43 |
|  | X6 | P | exosome component 5 (EXOSC5) |
|  | X7 | P, gP, gP | Huntingtin interacting protein K (HYPK) |
|  | X8 | P | keratin 10 (KRT10) |
|  | X9 | gP, gP | Methylenetetrahydrofolate dehydrogenase (MTHFD1) |
|  | X10 | gP | mitochondrial ribosomal protein L32 |
|  | X11 | L, L | M-phase phosphoprotein 10 (MPHOSPH10) |
|  | X12 | gP, P | RAP1 interacting factor homolog (yeast) (RIF1) |
|  | X13 | gP | Restin (RSN) |
|  | X14 | P | RNA binding motif protein 4 (RBM4) |
|  | X15 | gP, P, P | S100 calcium binding protein A2 (S100A2) |
|  | X16 | L | selenium binding protein 1 (SELENBP1) |
|  | X17 | gP, gP | SVH protein (SVH) |
|  | X18 | gP, L | translocated promoter region (to activated MET oncogene) |
|  | X19 | gP | BRCC1 (BRCC1) |
|  | X20 | gP | nucleophosmin (NPM1) |
|  | X21 | gP | COP9 constitutive photomorphogenic homolog subunit 3 |
|  | X22 | P, P | kinesin family member 15 (KIF15) |
|  | X23 | L | zinc finger protein 24 (KOX 17) (ZNF24) |
|  | X24 | P, L | golgi autoantigen macrogolgin (with transmembrane signal) (GOLGB1) |
| Patient 2 | X25 | P, P, P | HLA |
|  | X26 | P | 18S rRNA gene |
|  | X27 | P, P, P | Bcl-XL-binding protein v68 (MGC5352) |
|  | X28 | P, P | Cullin-associated and neddylation-dissociated 1 (CAND1) |
|  | X29 | P | heat shock 60 kDa protein 1 (chaperonin) (HSPD1) |
|  | X30 | L, P, P | hypothetical protein FLJ10534 |
|  | X31 | P | MAX gene associated (MGA) (PREDICTED) |
|  | X32 | P, P, P | Molybdenum cofactor sulfurase (MOCOS) |
|  | X33 | P | peroxisomal D3, D2-enoyl-CoA isomerase (PECI) |
|  | X34 | L, P, P | ribonuclease III, nuclear (RNASEN) |
|  | X35 | P, P, P | RNA binding motif protein 25 (RBM25) |
|  | X36 | P, P, P | Sjogren's syndrome/scleroderma autoantigen 1 |
|  | X37 | P, P | SVH protein (SVH) |
|  | X38 | P | TSR1, 20S rRNA accumulation, homolog (yeast) (TSR1) |
|  | X39 | gP, P, P | RNA binding motif protein 25 (RBM25) |
|  | X40 | P | Deltex 3-like (Drosophila) (DTX3L) |
|  | X41 | P, L, P | recombining binding protein suppressor of hairless |
|  | X42 | P | Coiled-coil domain containing 18 (CCDC18) |

TABLE 1-continued

| Hit pulled out using what post serum? | X# | Plugs Came From Which Lib? | Gene |
|---|---|---|---|
| Patient 3 | X43 | P | centromere protein F, 350/400ka (mitosin) (CENPF) |
| | X44 | L | chromosome 1 open reading frame 80 (C1orf80) |
| | X45 | L, L, L | cleavage and polyadenylation specific factor 2 (CPSF2) |
| | X46 | L | Enoyl Coenzyme A hydratase 1, peroxisomal (ECH1) |
| | X47 | | filamin B, beta (actin binding protein 278) (FLNB) |
| | X48 | L, P, P | G elongation factor, mitochondrial 2 (GFM2) |
| | X49 | L, P, P | heat shock 60 kDa protein 1 (chaperonin) (HSPD1) |
| | X50 | L | heat shock 70 kDa protein 8 (HSPA8), transcript variant 2 |
| | X51 | L, P | heat shock 70 kDa protein 9B (mortalin-2) (HSPA9B) |
| | X52 | P, L, L | InaD-like (*Drosophila*) (INADL) |
| | X53 | L | Jumonji |
| | X54 | L | mRNA for mitotic kinesin-like protein-1 (MKLP-1 gene) |
| | X55 | L, P, P | Restin (RSN) |
| | X56 | L | Ubiquinol-cytochrome c reductase hinge protein (UQCRH) |
| Patient 4 | X58 | L | PNPO |
| Patient 5 | X60 | gP, gL, P | chaperonin containing TCP1, subunit 5 (epsilon) (CCT5) |
| | X61 | L, gL, gP | chromosome 10 open reading frame 118 (C10orf118) |
| | X62 | gL, gP | Enoyl Coenzyme A hydratase 1, peroxisomal (ECH1) |
| | X63 | P | Eukaryotic translation initiation factor 3, subunit 9 eta, 116 kDa (EIF3S9) |
| | X64 | gL, P | Filamin B, beta (actin binding protein 278) (FLNB) |
| | X65 | gL, gL, L | heterogeneous nuclear ribonucleoprotein K (HNRPK), var 1 |
| | X66 | gL, gP, P | Huntingtin interacting protein K (HYPK) |
| | X67 | P | hypothetical protein FLJ14668 (FLJ14668) |
| | X68 | L, gP, L | hypothetical protein FLJ21908 (FLJ21908) |
| | X69 | L | interleukin enhancer binding factor 3, 90 kDa (ILF3), var 1 |
| | X70 | P | KIAA0310 |
| | X71 | gP | membrane-associated ring ringer (C3HC4) 6 (MARCH6) |
| | X72 | P, gL, gP | methylmalonyl Coenzyme A mutase (MUT) |
| | X73 | gL, gP, P | M-phase phosphoprotein 10 (MPHOSPH10) |
| | X74 | gL, L | myosin, heavy polypeptide 10, non-muscle (MYH10) |
| | X75 | gP | neuroblastoma breakpoint family, member 9, variant 13 (NBPF9)-predicted |
| | X76 | L | non-metastatic cells 1, protein (NM23A) expressed in (NME1), var 1 |
| | X77 | P, P | NSFL1 (p97) cofactor (p47) (NSFL1C), var 1 |
| | X78 | P | Rho-associated, coiled-coil containing protein kinase 2 (ROCK2) |
| | X79 | L | ribosomal protein S15a (RPS15A), var 1 |
| | X80 | gP, gP, P | translocase of outer mitochondrial membrane 70 homolog A (TOMM70A) |
| | X81 | gP | upstream binding transcription factor, RNA polymerase I (UBTF) |
| | X82 | L, L | YTH domain containing 2 (YTHDC2) |
| Patient 6 | X83 | gP | Coiled-coil domain containing 46 (CCDC46), var 1 |
| | X84 | gP | KIAA0196 |
| | X85 | gP | ribosomal protein L21 (RPL21) |
| | X86 | gP, gL, L | SWI/SNF related, matrix assoc., actin dependent reg of chromatin (SMARCA3) |
| | X87 | P | thyroid hormone receptor interactor 12 (TRIP12) |
| Patient 7 | X92 | | disrupter of silencing 10 (SAS10) |
| | X94 | | heat shock 60 kDa protein 1 (chaperonin) (HSPD1) |
| | X96 | | high-mobility group box 2 (HMGB2) |
| | X97 | | interphase cyctoplasmic foci protein 45 (ICF45) |
| | X100 | | LSM3 homolog, U6 small nuclear RNA associated (LSM3) |
| | X101 | | methylmalonyl Coenzyme A mutase (MUT) |
| | X102 | | NSFL1 (p97) cofactor (p47) (NSFL1C) |
| | X103 | | par-3 partitioning defective 3 homolog (*C. elegans*) (PARD3) |
| | X105 | | proteasome (prosome, macropain) 26S subunit, non-ATPase, 2 (PSMD2) |
| | X107 | | SVH protein (SVH) |
| | X108 | | TAO kinase 3 (TAOK3) |
| | X110 | | golgi autoantigen, macrogolgin (with transmembrane signal), 1 (GOLGB1) |
| | X111 | | heat shock 70 kDa protein 8 (HSPA8) |
| Patient 8 | X113 | L | kinetochore associated 2 (KNTC2) |
| | X118 | PIT | opioid growth factor receptor (OGFR) |
| | X120 | P, P | nexilin (F actin binding protein) (NEXN) |
| | X125 | L | NSFL1 (p97) cofactor (p47) (NSFL1C) |
| | X126 | L, L | hypothetical protein FLJ21908 (FLJ21908) |
| | X128 | L, P | NADH dehydrogenase (ubiquinone) flavoprotein 2, 24 kDa (NDUFV2) |
| | X130 | P | chromosome 14 DNA sequence BAC C-2555O16 (see note for rest) |

TABLE 1-continued

| Hit pulled out using what post serum? | X# | Plugs Came From Which Lib? | Gene |
|---|---|---|---|
| | X131 | L, P | ankyrin repeat and KH domain containing 1 (ANKHD1)/ (MASK-BP3) |
| | X132 | L, L | heterogeneous nuclear ribonucleoprotein K (HNRPK) |
| | X133 | L, P | kinesin family member 15 (KIF15) |
| | X134 | L | translocated promoter region (to activated MET oncogene) (TPR) |
| | X135 | L, L | acetyl-Coenzyme A acetyltransferase 2(ACAT2) |
| | X136 | L, P | Huntingtin interacting protein K (HYPK) |
| | X137 | L | InaD-like (*Drosophila*) (INADL) |
| Patient 4 | X138 | L, P | ring finger protein 8 (RNF8) |
| cont. | X139 | L, P | colony stimulating factor 2 (granulocyte-macrophage) (CSF2) |
| | X141 | L | A kinase (PRKA) anchor protein (yotiao) 9 (AKAP9) |

6.1.2. Expanded Analysis of Induced Autoantibody Responses

Employing the compiled list of 143 proteins to which autoantibody responses were observed from the 8 patients, samples from a larger cohort of patients (up to 14 in total) were screened to determine the frequency and selectivity of antibody responses. Representative phage clones of each of the 143 proteins were screened against patient sera pre and post-immunotherapy. Results for all 8 patients from which the clones were originally isolated, are presented in Tables 2 and 3, below.

Results from this expanded screen of patients sera indicate that for a number of proteins, auto-antibodies are induced at a relatively high frequency following immunotherapy. For interpretation, these antigens have been grouped into 2 classes as shown in Tables 2 and 3, below. Although grouped separately for presentation purposes, both groups of genes (de novo and induced) may serve as an important marker of clinical benefit in patients.

De novo antigens (Table 2), were antibody responses that are not detectable pre-therapy in any patient screened so far, but are present in at least 2 (of the 14 patients screened) following immunotherapy. Response is absolute (on/off).

"Induced" antigens (Table 3), were antibody responses that are detectable pre-therapy in a proportion of patients and titer is increased in at least 2 patients post-therapy (enhancement of pre-existing antibody response).

TABLE 2

De novo antibody responses

| Gene | Genbank accession number | Frequency of autoantibody induction Following GVAX ® |
|---|---|---|
| HLA-A gene, HLA-A24 allele | NM_002116 | 8/13 (62%) |
| Filamin B, beta (FLNB) | NM_001457 | 7/12 (58%) |
| NSFL1 (p97) cofactor (p47) (NSFL1C) | NM_016143 | 3/6 (50%) |
| Pyridoxine 5'phosphate oxidase (PNPO) | NM_018129 | 6/13 (46%) |
| SVH protein (SVH) | NM_031905 | 4/9 (44%) |
| Heat shock 60 kDa (HSPD1) | NM_002156 | 4/9 (44%) |
| YTH domain containing 2 (YTHDC2) | NM_022828 | 3/10 (30%) |
| Chaperonin containing TCP1, subunit 5 (CCT5) | NM_012073 | 3/10 (30%) |
| KIAA0196 | NM_014846 | 2/7 (29%) |

TABLE 2-continued

De novo antibody responses

| Gene | Genbank accession number | Frequency of autoantibody induction Following GVAX ® |
|---|---|---|
| InaD-like (*Drosophila*) (INADL) | NM_176878 | 3/12 (25%) |
| Translocated promoter region (to activated MET oncogene) (TPR) | NM_003292 | 2/8 (25%) |
| Disrupter of silencing 10 (SAS10) | NM_020368 | 2/8 (25%) |
| Enoyl Coenzyme A hydratase 1, peroxisomal (ECH1) | NM_001398 | 3/13 (23%) |
| Heat shock 70 kDa protein 8 (HSPA8) | NM_006597/ 153201 | 2/9 (22%) |
| Methylmalonyl Coenzyme A mutase (MUT) | NM_000255 | 2/9 (22%) |
| LSM3 homolog, U6 small nuclear RNA associated (LSM3) | NM_014463 | 2/9 (22%) |
| Dihydrolipoamide S-acetyltransferase (DLAT) | NM_001931 | 2/9 (22%) |
| Huntingtin interacting protein K (HYPK) | NM_016400 | 3/14 (21%) |
| Non-metastatic cells 1, protein (NM23A) expressed in (NME1) | NM_000269/ 198175 | 2/10 (20%) |
| KIAA0310 | XM_946064 | 2/10 (20%) |
| Eukaryotic translation initiation factor 3, subunit 9 eta, 116 kDa (EIF3S9) | NM_001037283/ 003751 | 2/10 (20%) |
| Acetyl-Coenzyme A acetyltransferase 2 (ACAT2) | NM_005891 | 2/14 (18%) |
| Proteasome (prosome, macropain) 26S subunit, non-ATPase, 2 (PSMD2) | NM_002808 | 2/11 (18%) |
| Kinetochore associated 2 (KNTC2) | NM_006101 | 2/11 (18%) |
| Interphase cytoplasmic protein 45 (ICF45) | NM_017872 | 2/13 (15%) |
| Translocated promoter region (to activated MET oncogene) | NM_003292 | 2/13 (15%) |
| RAP1 interacting factor homolog (yeast) (RIF1) | NM_018151 | 2/13 (15%) |

TABLE 3

Induced antibody responses

| Gene | Genbank accession number | Frequency of pre-existing, un-augmented autoantibody response |
| --- | --- | --- |
| M-phase phosphoprotein 10 (MPHOSPH10) | NM_005791 | 5/14 |
| TAO Kinase 3 (TAOK3) | NM_016281 | 4/9 |
| Upstream binding transcription factor, RNA polymerase 1 (UBTF) | NM_014233 | 5/10 |
| Jumonji, AT rich interactive domain 1A (RBBP2-like) (JARID1A) | NM_005056 | 6/12 |
| Rho-associated, coiled-coil containing protein kinase 2 (ROCK2) | NM_004850 | 6/9 |
| Golgi autoantigen, macrogolgin (with transmembrane signal), 1 (GOLGB1) | NM_004487 | 6/9 |
| Bcl-XL-binding protein v68 (MGC5352) | NM_138575 | 3/13 |
| Mitochondrial ribosomal protein L32 (MRPL32) | NM_031903 | 10/14 |
| Kinesin family member 15 (KIF15) | NM_020242 | 1/14 |
| Centromere protein F, 350/400ka (mitosin) (CENPF) | NM_016343 | 2/12 |
| Membrane-associated ring finger (C3HC4) 6 (MARCH6) | NM_005885 | 3/8 |
| Coiled-coil domain containing 46 (CCDC46), var 1 | NM_001037325 NM_1455036 | 2/9 |
| Restin (Reed-Steinberg cell-expressed intermediate filament-associated protein) (RSN) | NM_198240 | 2/11 (18%) |
| Coiled-coil domain containing 18 (CCDC18) | NM_206886 | 4/11 |
| Acetyl-Coenzyme A acyltransferase 1 (ACAA1) | NM_001607 | 1/14 |

Therefore in patients treated with cell-based pro state cancer immunotherapy, a number of autoantibody responses are induced at a relatively high frequency (FLNB, SVH, HSPD1, MPHOSPH10, etc.).

6.1.3. Cloning and Characterization of Antigens

The following list identifies to top 20 most frequent antibody responses (from both the de novo and induced gene lists):

TABLE 4

1. HLA-A gene, HLA-A24 allele
2. Filamin B, beta (FLNB)
3. M-phase phosphoprotein 10 (MPHOSPH10)
4. TAO Kinase 3 (TAOK3)
5. NSFL1 (p97) cofactor (p47) (NSFL1C)
6. Upstream binding transcription factor, RNA polymerase 1 (UBTF)
7. Pyridoxine 5'phosphate oxidase (PNPO)
8. SVH protein (SVH)
9. Heat shock 60 kDa (HSPD1)
10. Jumonji, AT rich interactive domain 1A (RBBP2-like) (JARID1A)
11. Bcl-XL-binding protein v68 (MGC5352)
12. YTH domain containing 2 (YTHDC2)
13. Chaperonin containing TCP1, subunit 5 (CCT5)
14. Kinesin family member 15 (KIF15)
15. InaD-like (*Drosophila*) (INADL)
16. Enoyl Coenzyme A hydratase 1, peroxisomal (ECH1)

TABLE 4-continued

17. Huntingtin interacting protein K (HYPK)
18. Non-metastatic cells 1, protein (NM23A) expressed in (NME1)
19. Acetyl-Coenzyme A acetyltransferase 2 (ACAT2)
20. Methylmalonyl Coenzyme A mutase (MUT)

Full length genes are cloned into a mammalian based expression system (e.g., a lentiviral expression plasmid) and a FLAG-tag is added at the C-terminal end to aid with detection and purification. Antibody responses to these high frequency hits of 20 proteins are determined from all trials available (G98-03, G0010, VITAL-1/2) and the induction of antibody response is examined in correlation to survival. These responses either alone, or grouped with the defined antigen responses discussed below, are used for a number of applications including a surrogate marker of immunotherapy treatment, correlation with patient survival data to provide an efficacy signature, clinical trial monitoring (biomarkers) and assay development of cell characterization marker for lot release (product characterization, comparability markers).

Certain of the above-identified antigens were cloned and characterized as set forth below.

6.1.3.1 Cloning, Protein Production and Antibody Response to FLNB in Patients Administered a Cell-Based Prostate Cancer Immunotherapy FLNB was cloned with a C-terminus Flag tag into a lentivirus plasmid vector for protein production. To generate the plasmid a FLNB intermediate was first cloned which contained the 3'end of FLNB attached to C-terminal Flag tag sequence (in frame). To generate this clone, a PCR fragment was generated using the forward primer (5'-actacctgatcagt-gtcaaa-3') (SEQ ID NO.: 18) and the reverse primer (5'-gtaatctccggaaggcactgtgacatgaaaag-3') (SEQ ID NO.: 19) using a FLNB template obtained from Invitrogen (clone CS0DK001 YE14) and High Fidelity Expand PCR kit (Roche). The resulting PCR product was cleaned by Qiagen PCR Purification kit, digested with BspE1 and then ligated into a parental lentivirus plasmid vector pKCCMVp53flag which was previously digested with Sma1 and BspE1. To generate the full length FLNB Flag tag vector, the following fragments were ligated together: the Age1 to Sal1 fragment from pKCCMVGFP, the BspE1 to Bcl1 fragment from the Invitrogen FLNB clone CS0DK001YE14, and the Bcl1 to Sal1 fragment from the FLNB intermediate described above. The vector construct called pKCCMVFLNBflag was fully sequenced.

To express FLNB, Flag-tagged FLNB was produced in mammalian cells and purified using affinity purification. In brief, twenty-four hours before transfection, 10 75 cm$^2$ plates were seeded with 5×10$^6$ cells/plate HEK293 cells. Twenty-four hours later, cells were transfected with 10 µg/plate of pKCCMVFLNBflag using a calcium phosphate transfection kit (Clontech). Three days post-transfection cells were lysed with cell lysis buffer (+protease inhibitors) and FLNB protein purified using Anti-Flag M2 affinity columns (Sigma) according to manufacturing instructions.

For western blot analysis of patients antibodies to filamin B, 150 ng of purified filamin B was separated on a Tris-Glycine gel (Invitrogen) under reducing conditions and transferred to a nitrocellulose membrane. Blots were then blocked overnight with 3% nonfat dry milk in TBS and incubated with a 1:500 dilution of patients serum post-therapy for 3 hours. Blots were then washed in TBST and incubated with an IgG/IgM specific donkey anti-human secondary antibody conjugated to horseradish peroxidase for an hour and a half. Following TBST washes immunoreactive bands were visualized by exposure of photographic film (Kodak) after the blots were treated with the ECL enhanced chemiluminescence system (Pierce). Patients 1, 3, 4, and 5 an immunoreactive band at 280 kDa running at the predicted molecular weight could be observed in the post-therapy serum samples, while immunoreactivity was absent in pre-therapy samples.

Patient antibodies to FLNB were also monitored in an ELISA. To do so, 96 well plates were coated with 250 ng/well of purified FLNB overnight in bicarbonate buffer (coating buffer). Next day, wells were washed with PBST and then blocked using 1% BSA in PBST for 3 hours at room temperature. Following blocking, wells were washed in PBST and serum added at a range of concentrations (1:100-10,000) diluted in PBST+1% BSA. One and half hours post-serum addition, plates were washed and then incubated with a Donkey-anti Human IgG IgM HRP-conjugated secondary antibody (Jackson) diluted at 1:10,000 in PBST for 1 hour at room temperature. Plates were then washed and bound secondary antibody detected using TBM (KPL). Plates were then read at 450 nm. To determine induction of an FLNB antibody response, the post-therapy O.D. value was divided by the pre-therapy O.D to determine a fold induction. Fold induction levels >2 were considered significant. In patients 1, 3, 4, and 5, a significant fold increase in O.D. could be observed by the post/pre ratio. In comparison IgG/IgM antibodies to tetanus toxoid, a protein to which the majority of the population has been actively vaccinated to, was unchanged (pre/post ration <2) following treatment indicating the increase in titer is FLNB specific. Results indicating patient antibody generation to FLNB following therapy agree for western blot and ELISA analysis (i.e. patients 1, 3, 4, and 5 were positive).

6.1.3.2 Cloning, Protein Production and Antibody Response to PNPO Following Immunotherapy PNPO was cloned with a C-terminus Flag tag into a lentivirus plasmid vector, using a PNPO clone identified from SEREX analysis to generate pKCCMVPNPOflag. PNPO-flag was cloned by PCR attaching the Flag tag to the 3'end of the gene using the forward primers (5'-gcctacccacaggagattcc) (SEQ ID NO.: 20) and the reverse primer (5'-gtaatctccggaaggtgcaagtctcataga (SEQ ID NO.: 21) using a SEREX identified PNPO clone as s DNA PCR template. The PCR product was cleaned by Qiagen PCR purification kit, digested with Apa1 and BspE1, and ligated into identical sites in the parental vector pKCCMVp53flagdR1. The vector construct called pKCCMVPNPOflag was then sequence verified.

Flag-tagged PNPO was produced in mammalian cells and purified using affinity purification. In brief, twenty-four hours before transfection, 10 75 cm$^2$ plates were seeded with 5×10e6 cells/plate HEFK293 cells. Twenty-four hours later, cells were transfected with 10 μg/plate of pKCCMVPNPO-flag using a calcium phosphate transfection kit (Clontech). Three days post-transfection cells were lysed with cell lysis buffer (+protease inhibitors) and PNPO protein purified using Anti-Flag M2 affinity columns (Sigma) according to manufacturing instructions.

For western analysis of patients antibodies to PNPO, 150 ng of purified PNPO was separated on a Tris-Glycine gel (Invitrogen) under reducing conditions and transferred to a nitrocellulose membrane. Blots were then blocked overnight with 3% nonfat dry milk in TBS and incubated with a 1:500 dilution of patients serum post-therapy for 3 hours. Blots were then washed in TBST and incubated with an IgG/IgM specific donkey anti-human secondary antibody conjugated to horseradish peroxidase for an hour and a half. Following TBST washes immunoreactive bands were visualized by exposure of photographic film (Kodak) after the blots were treated with the ECL enhanced chemiluminescence system (Pierce). In samples from Patients 1, 2, 3, and 5, an immunoreactive band at 30 kDa running at the predicted molecular weight of PNPO could be observed in the post-therapy serum samples. Immunoreactivity was absent in pre-therapy samples.

96 well plates were coated with 250 ng/well of purified PNPO overnight in bicarbonate buffer (coating buffer). The next day, wells were washed with PBST and then blocked using 1% BSA in PBST for 3 hours at room temperature. Following blocking, wells were washed in PBST and serum added at a range of concentrations (1:100-10,000) diluted in PBST+1% BSA. One and half hours post-serum addition, plates were washed and then incubated with a Donkey-anti Human IgG IgM HRP-conjugated secondary antibody (Jackson) diluted at 1:10,000 in PBST for 1 hour at room temperature. Plates were then washed and bound secondary antibody detected using TBM (KPL). Plates were then read at 450 nm. To determine induction of an PNPO antibody response, the post-therapy O.D. value was divided by the pre-therapy O.D. to determine a told induction. Fold induction levels >2 were considered significant. In patients 1, 2, 3 and 5, a significant fold increase in O.D. could be observed by the post/pre ratio. In comparison, IgG/IgM antibodies to tetanus toxoid, a protein against which the majority of the population has been actively vaccinated, were unchanged (pre/post ration <2) following treatment. This indicates that the increase in titer was PNPO specific. Results indicating patient antibody generation to PNPO following therapy agreed for western blot and ELISA analysis (i.e., patients 1, 2, 3 and 5 were positive for both assays).

6.1.3.3 Cloning, Protein Production and Antibody Response to NSFLIC

NSFLIC was cloned with a C-terminus Flag tag into a lentivirus vector. using a NSFLIC clone identified from SEREX analysis to generate pKCCMVNSFLICflag. pKCCMVNSFLICflag was cloned by PCR attaching the Flag tag to the 3'end of the NSFLIC gene and an ATG start codon to the 5'end of the gene. To generate this PCR product, the forward primer (5'-gggcccgaattcatggcggcggagcgacaggaggcgctg) (SEQ ID NO.: 22) and the reverse primer (5'-gtaatctccggatgttaaccgctgcacgatga) (SEQ ID NO.: 23) were used with the SEREX identified clone of NSFLIC as the DNA PCR template and High Fidelity Expand PCR kit. The PCR product was cleaned by Qiagen PCR Purification Kit, digested with EcoR1 and BspE1, and ligated into identical sites in the parental vector pKCCMVp53flagdR1. The resulting vector construct pKCCMVNSFLICflag was sequenced verified.

Flag-tagged NSFLIC was produced in mammalian cells and purified using affinity purification. In brief, twenty-four hours before transfection, 10 75 cm$^2$ plates were seeded with 5×10e6 cells/plate 1HEK293 cells. Twenty-four hours later, cells were transfected with 10 μg/plate of pKCCMVNSFLICflag using a calcium phosphate transfection kit (Clontech). Three days post-transfection cells were lysed with cell lysis buffer (+protease inhibitors) and NSFLIC protein purified using Anti-Flag M2 affinity columns (Sigma) according to manufacturing instructions.

For western analysis of patients antibodies to NSFLIC, 150 ng of purified NSFLIC was separated on a Tris-Glycine gel (Invitrogen) under reducing conditions and transferred to a nitrocellulose membrane. Blots were then blocked overnight with 3% nonfat dry milk in TBS and incubated with a 1:500 dilution of patients serum post-therapy for 3 hours. Blots were then washed in TBST and incubated with an IgG/IgM specific donkey anti-human secondary antibody conjugated to horseradish peroxidase for an hour and a half. Following TBST washes immunoreactive bands were visualized by exposure of photographic film (Kodak) after the blots were treated with the ECL enhanced chemiluminescence system (Pierce). In serum from patients 1, 3 and 4, an immunoreactive band at 40 kDa correlating with the expected size of NSFLIC could be observed in the post-therapy serum samples. Immunoreactivity was absent in pre-therapy samples.

ELISAs were also performed to assess immune response against NSFLIC. To do so, 96 well plates were coated with 250 ng/well of purified NSFLIC overnight in bicarbonate buffer (coating buffer). Next day, wells were washed with PBST and then blocked using 1% BSA in PBST for 3 hours at room temperature. Following blocking, wells were washed in PBST and serum added at a range of concentrations (1:100-10,000) diluted in PEST+1% BSA. One and half hours post-serum addition, plates were washed and then incubated with a Donkey-anti Human IgG IgM HRP-conjugated secondary antibody (Jackson) diluted at 1:10.000 in PBST for 1 hour at room temperature. Plates were then washed and bound secondary antibody detected using TBM (KPL). Plates were then read at 450 nm. To determine induction of a NSFLIC antibody response, the post-therapy O.D. value was divided by the pre-therapy O.D. to determine a fold induction. Fold induction levels >2 were considered significant. In patients 1, 3 and 4, a significant fold increase in O.D. to NSFLIC could be observed by the post/pre ratio. In comparison IgG/IgM antibodies to tetanus toxoid, a protein to which the majority of the population has been actively vaccinated to, was unchanged (pre/post ration <2) following treatment indicating the increase in titer is NSFLIC specific. Results indicating patient antibody generation to NSFLIC following treatment agree for western blot and ELISA analysis (i.e., patients 1, 3 and 4 were positive for both ELISA and western analysis).

6.1.4. Expression Levels of Genes

The role of some of the high-frequency hits in prostate cancer progression through examining RNA expression levels has been preliminarily examined. For example, FIGS. 1 and 2 present the expression patterns of PNPO and FLNB, respectively, with increasing prostate cancer disease grade derived from the Oncomine database (www.oncomine.com). Expression of both PNPO and FLNB are induced upon prostate cancer disease progression, lying in with their potential roles as tumor associated antigens. Expression of the closely related family member filamin A (ABP280), is selectively down-regulated with disease progression for comparison (Varambally et al. 2005).

6.2 Example 2: Defined Prostate Cancer Antigen Screening

This example describes the results of experiments designed to assess humoral immune responses against prostate cancer antigens. In these experiments, a selection of 20 genes that are associated with prostate cancer and have previously demonstrated an interaction with the immune response were selected for evaluation. The genes are set forth in Table 5, below. This list includes:

TABLE 5

Prostate specific antigen (PSA)
Prostate-specific membrane antigen (PSMA)
Prostatic acid phosphatase (PAP)
Prostate stem cell antigen (PSCA)
NY-ESO-1
LAGE
Telomerase (hTERT)
p53
Carcinoembryonic antigen (CEA)
Her2/neu
α-methylacyl-CoA racemase (AMACR)
Glucose-regulated protein-78 kDa (GRP78)
P62
P90
Cyclin-B1
TARP (T-cell receptor gamma alternate reading frame protein)
Filamin B (CGi identified)
Prostein
Survivin
Prostase/Kallikrein 4

All of these candidates were cloned into a plasmid expression system and recombinant proteins expressed using FLAG-tag based immunoaffinity purification. Following protein production, patient serum was assessed in both a western blot and/or in an ELISA format to immunoscreen candidates for antibody reactivity. Screening the patients from a monotherapy trial, 5 antigens associated with an autoantibody response were identified as set forth in Table 6, below.

TABLE 6

| Gene | Genbank accession number | Frequency of pre-existing, un-\ augmented autoantibody response | Frequency of autoantibody induction |
| --- | --- | --- | --- |
| Filamin B, beta (FLNB) | NM_001457 | 0/7 | 4/7 |
| Prostate-specific membrane antigen (PSMA) | NM_004476 | 1/7 | 1/7 |
| Her2/neu | NM_004448 | 1/7 | 0/7 |
| NY-ESO-1 | HSU87459 | 0/7 | 1/6 |
| LAGE-1a | HSA223041 | 0/7 | 1/6 |

6.2.1. Cloning and Characterization of Antigens

Following identification of proteins correlated with an antibody response in serum, antigen targets are further characterized for cellular immune response (T-cells) using peripheral blood mononuclear cells (PBMCs) harvested from patients administered cell-based prostate cancer immunotherapy.

6.2.1.1 Detecting Activation of Cytotoxic T Lymphocytes in IFN-γ Assays

This example provides an exemplary method for detecting activation of cytotoxic T lymphocytes (CTLs) by monitoring IFN-γ expression by the CTLs in response to exposure to an appropriate antigen, e.g., a filamin-B peptide presented on an MHC I receptor.

First, peripheral blood monocytic cells (PBMCs) are isolated from a subject to be assessed for cellular immune response against a filamin-B peptide and CD8+ cells are isolated by fluorescence activated cell sorting (FACS). The CD8+ cells are then incubated with, e.g., T2 cells loaded with the filamin-B peptide to be assessed, produced as described above, and in the presence of suitable cytokines for expanding the CTL population.

IFN-γ release by the CTLs is measured using an IFN-γ ELISA kit (PBL-Biomedical Laboratory, Piscataway, N.J.). Briefly, purified IFN-γ as standards or culture supernates from the CTL-T2 co-culture are transferred into wells of a 96-well plate pre-coated with a monoclonal anti-human IFN-γ capture antibody and incubated for 1 h in a closed chamber at 24° C. After washing the plate with PBS/0.05% Tween 20, biotin anti-human IFN-γ antibody is added to the wells and incubated for 1 h at 24° C. The wells are washed and then developed by incubation with streptavidin horseradish peroxidase conjugate and TMB substrate solution. Stop solution is added to each well and the absorbance is determined at 450 nm with a SpectraMAX Plus plate reader (Stratagene, La Jolla, Calif.). The amount of cytokine present in the CTL culture supernatants is calculated based on the IFN-γ standard curve.

6.2.1.2 Detecting Activation of Cytotoxic T Lymphocytes in Proliferation Assays

This example provides an exemplary method for detecting activation of cytotoxic T lymphocytes (CTLs) by CTL proliferation in response to exposure to an appropriate antigen, e.g., a filamin-B peptide presented on an MHC I receptor.

First, peripheral blood monocytic cells (PBMCs) are isolated from a subject to be assessed for cellular immune response against a filamin-B peptide and CD8+ cells are isolated by fluorescence activated cell sorting (FACS). The CD8+ cells are then incubated with, e.g., T2 cells loaded with the filamin-B peptide to be assessed, produced as described above.

Next, the samples are incubated for 12 hours, then 20 µl of 3H-thymidine is added to each well and the sample incubated for an additional 12 hours. Cells are harvested and the plate is read in a beta counter to determine the amount of unincorporated 3H-thymidine.

6.2.1.3 Detecting Activation of Cytotoxic T Lymphocytes in Effector Assays

This example provides an exemplary method for detecting activation of cytotoxic T lymphocytes (CTLs) by monitoring lysis of cells displaying an appropriate antigen, e.g., a filamin-B peptide presented on an MHC I receptor.

The cytotoxic activity of the CTLs is measured in a standard $^{51}$Cr-release assay. Effector cells (CTLs) are seeded with $^{51}$Cr-labeled target cells ($5\times10^3$ cells/well) at various effector:target cell ratios in 96-well U-bottom microtiter plates. Plates are incubated for 4 h at 37° C., 5% $CO_2$. The $^{51}$Cr-release is measured in 100 µl supernatant using a Beckman LS6500 liquid scintillation counter (Beckman Coulter, Brea, Calif.). The percent specific cell lysis is calculated as [(experimental release−spontaneous release)/(maximum release−spontaneous release)]. Maximum release is obtained from detergent-released target cell counts and spontaneous release from target cell counts in the absence of effector cells.

6.3 Autoantibody Detection Following Therapy Using Protein Microarrays

In addition to SEREX and defined prostate tumor associated antigen screening, a third technique, autoantibody detection using protein microarrays, was employed to determine therapy-related increases in patient antibody titer following immunotherapy. Protein microarrays are new tools that provide investigators with defined protein content for profiling serum samples to identify autoantigen biomarkers (Casiano et al. 2006; Bradford et al. 2006: Qin et al. 2006). Invitrogen's ProtoArrayg® Human Protein Microarrays (version 4) contain over 8,000 purified human proteins immobilized on glass slides. Probing protein microarrays with serum from pre-therapy and post-therapy patient serum samples allows the identification of immunogenic proteins that are potential antigens.

6.3.1. Immune Response Biomarkers Identified by ProtoArray Analysis: Set 1

Immune Response Biomarker Profiling was performed by Invitrogen for seven serum samples: Pre-therapy and Post-therapy serum samples for 3 patients and 1 normal serum donor for comparison. The reactivity of serum antibodies against proteins on ProtoArray® Human Protein Microarrays was investigated. Comparisons were made across sera from three individual prostate cancer patients prior to and following treatment. For each patient, a number of proteins were identified exhibiting elevated signals (pixel intensity) in the post-treatment sample relative to the prostate cancer samples prior to therapy. While a number of markers were unique to the individual patients, several candidate autoantigens were identified that were shared between multiple patients included in the study. These included the proteins listed below:

TABLE 7

OTUB2
FLJ14668
HIGD2A
LOC51240
Neuronatin
CD52
ORM1-like3
Mitogen-activated protein kinase kinase kinase 11
UBX domain containing 8

Protein array analysis indicated 2 of the 3 patients were positive for the protein OTUB2 (Swiss-prot Q6DC9). Patients displayed a 14.1 and 7.7-fold increase in titer, compared to a low signal background in normal serum samples.

Protein array analysis indicated 3 out of the 3 patients were positive for the protein product derived from FLJ14668 (NP_116211). Patients displayed a 36.2, 5.2 and 7.7-fold increase in titer, compared to a low signal background in the normal serum samples.

Protein array analysis indicated 3 out of the 3 patients were positive for the protein product of gene HIGD2A (NP_620175). Patients displayed a 3.5, 2.2 and 2.1-fold increase in antibody titer, compared to a low signal background in the normal serum samples.

Protein array analysis indicated 3 out of the 3 patients were positive for the protein product of gene LOC51240 (NP_054901). Patients displayed a 5.2, 4.7 and 6.4-fold increase in antibody titer, compared to a low signal background in the normal serum samples.

Protein array analysis indicated 3 out of the 3 patients were positive for the protein product of gene Neuronatin (NP_005377 (isoform A/NP_859017 (isoform B)). Patients displayed a 8.0, 2.3 and 2.6-fold increase in antibody titer, compared to a low signal background in the normal serum samples Protein array analysis indicated 3 out of the 3 patients were, positive for the protein product of gene CD52 (NP_001794). Patients displayed a 4.1, 2.4 and 3.1-fold increase in antibody titer, compared to a low signal background in the normal serum samples.

Protein array analysis indicated 3 out of the 3 patients were positive for the protein product ORM1-like 3 (NP_644809) of gene ORMDL3. Patients displayed a 5.6, 1.7 and 2.5-fold increase in antibody titer, compared to a low signal background in the normal serum samples.

Protein array analysis indicated 3 out of the 3 patients were positive for the protein product Mitogen-activated protein kinase kinase kinase 11 (NP_002410) of gene MAP3K11. Patients displayed a 7.7, 1.7 and 3.0-fold increase in antibody titer, compared to a low signal background in the normal serum samples.

Protein array analysis indicated 3 out of the 3 patients were positive for the protein product UBX domain containing 8 (NP_0955428) of gene UBXD8. Patients displayed a 5.9, 2.5 and 2.3-fold increase in antibody titer for 1 clone and 3.0, 1.8 and 1.6-fold increase for another clone, compared to a low signal background in the normal serum samples.

6.3.2. Immune Response Biomarkers Identified by ProtoArray Analysis: Set 2

Immune Response Biomarker Profiling was performed by Invitrogen for Pre-GVAX and Post-GVAX serum samples for 10 patients (8 patients from G-0010 and 2 from G-9803, described below). Patients were selected for ProtoArray analysis based upon their improved clinical outcome when comparing predicted survival (Halabi nomogram) to actual (Table 8).

TABLE 8

| GVAX Study | Patient # | Halabi score | Actual survival | Survival increase (Actual − Halabi) |
|---|---|---|---|---|
| G-0010 | 451 | 14 | 47.9 | 33.9 |
| G-0010 | 57 | 15 | 44.9 | 29.9+ |
| G-0010 | 202 | 21 | 52.2+ | 31.2+ |
| G-0010 | 101 | 25 | 43.9+ | 18.9+ |
| G-0010 | 355 | 24 | 35.5+ | 11.5+ |
| G-0010 | 306 | 18 | 36.2+ | 18.2+ |
| G-0010 | 205 | 24 | 48.3+ | 24.3+ |
| G-0010 | 268 | 21 | 41.5+ | 20.5+ |
| G-9803 | 804 | 22 | 38.5 | 16.5 |
| G-9803 | 304 | 19 | 42 | 23 |

+indicates that actual survival has not yet been reached

Comparisons were made across sera from 10 individual GVAX patients, and results were compared using M-Statistics to determine the differential signals between pine and post-GVAX populations that result in a significant P-value. Proteins that exhibited a significant increase in antibody titer ($p=<0.05$), as determined by ProtoArray, are displayed in Table 9.

TABLE 9

| Protein Description | Database ID | Pre-GVAX Count | Post-GVAX Count | Pre-GVAX Prevalence | Post-GVAX Prevalence | P-Value |
|---|---|---|---|---|---|---|
| lectin, galactoside-binding, soluble, 8 (galectin 8) (LGALS8) | BC015818.1 | 0 | 9 | 8.3% | 83.3% | 5.95E−05 |
| Cardiolipin - known Autoantigen | CARDIOLIPIN | 1 | 9 | 16.7% | 83.3% | 5.47E−04 |
| UBX domain containing 8 (UBXD8) | BC014001.1 | 0 | 7 | 8.3% | 66.7% | 1.55E−03 |
| CD52 molecule | NM_001803.1 | 0 | 7 | 8.3% | 66.7% | 1.55E−03 |
| ORM1-like 1 (S. cerevisiae) (ORMDL1) | NM_016467.1 | 1 | 10 | 16.7% | 91.7% | 1.55E−03 |
| neuronatin (NNAT) | NM_181689.1 | 2 | 9 | 25% | 83.3% | 2.74E−03 |
| TCR gamma alternate reading frame protein (TARP), nuclear gene encoding mitochondrial protein | NM_001003799.1 | 3 | 10 | 33.3% | 91.7% | 5.42E−03 |
| HIG1 domain family, member 2A (HIGD2A) | NM_138820.1 | 3 | 10 | 33.3% | 91.7% | 5.42E−03 |
| serine incorporator 2 (SERINC2) | BC017085.1 | 0 | 6 | 8.3% | 58.3% | 5.42E−03 |
| signal sequence receptor, gamma (translocon-associated protein gamma) (SSR3) | NM_007107.2 | 0 | 6 | 8.3% | 58.3% | 5.42E−03 |
| UBX domain containing 8 (UBXD8) | NM_014613.1 | 0 | 6 | 8.3% | 58.3% | 5.42E−03 |
| ORM1-like 3 (S. cerevisiae) (ORMDL3) | NM_139280.1 | 1 | 7 | 16.7% | 66.7% | 9.88E−03 |
| ribosomal protein S6 kinase, 90 kDa, polypeptide 2 (RPS6KA2) | PV3846 | 1 | 7 | 16.7% | 66.7% | 9.88E−03 |
| lectin, galactoside-binding, soluble, 3 (LGALS3) | BC001120.1 | 4 | 10 | 41.7% | 91.7% | 1.63E−02 |
| selenoprotein S (SELS) | BC005840.2 | 0 | 5 | 8.3% | 50% | 1.63E−02 |
| lectin, galactoside-binding, soluble, 8 (galectin 8) (LGALS8) | BC016486.1 | 0 | 5 | 8.3% | 50% | 1.63E−02 |
| chromosome 14 open reading frame 147 | BC021701.1 | 0 | 5 | 8.3% | 50% | 1.63E−02 |
| similar to CG10671-like (LOC161247) | BC042179.1 | 0 | 5 | 8.3% | 50% | 1.63E−02 |
| lectin, galactoside-binding, soluble, 3 (LGALS3) | BC053667.1 | 4 | 10 | 41.7% | 91.7% | 1.63E−02 |

TABLE 9-continued

| Protein Description | Database ID | Pre-GVAX Count | Post-GVAX Count | Pre-GVAX Prevalence | Post-GVAX Prevalence | P-Value |
|---|---|---|---|---|---|---|
| caveolin 3 (CAV3) | NM_001234.3 | 0 | 5 | 8.3% | 50% | 1.63E−02 |
| cytochrome b-561 domain containing 2 (CYB561D2) | NM_007022.1 | 0 | 5 | 8.3% | 50% | 1.63E−02 |
| ORM1-like 2 (S. cerevisiae) (ORMDL2) | NM_014182.2 | 0 | 5 | 8.3% | 50% | 1.63E−02 |
| signal peptidase complex subunit 1 homolog (S. cerevisiae) (SPCS1) | BC000884.1 | 1 | 6 | 16.7% | 58.3% | 2.86E−02 |
| hypothetical protein FLJ14668 | BC014975.1 | 1 | 6 | 16.7% | 58.3% | 2.86E−02 |
| chromosome 21 open reading frame 51 (C21orf51) | BC015596.1 | 1 | 6 | 16.7% | 58.3% | 2.86E−02 |
| kelch domain containing 7B (KLHDC7B) | NM_138433.2 | 0 | 6 | 8.3% | 58.3% | 2.86E−02 |
| presenilin enhancer 2 homolog (C. elegans) (PSENEN) | NM_172341.1 | 1 | 6 | 16.7% | 58.3% | 2.86E−02 |
| stearoyl-CoA desaturase (delta-9-desaturase) (SCD) | BC005807.2 | 3 | 8 | 33.3% | 75% | 3.49E−02 |
| interferon regulatory factor 2 (IRF2) | BC015803.1 | 0 | 4 | 8.3% | 41.7% | 4.33E−02 |
| TNF receptor-associated protein 1 (TRAP1) | BC018950.2 | 0 | 4 | 8.3% | 41.7% | 4.33E−02 |
| N-glycanase 1 (NGLY1) | NM_018297.2 | 0 | 4 | 8.3% | 41.7% | 4.33E−02 |
| Der1-like domain family, member 1 (DERL1) | NM_024295.1 | 0 | 4 | 8.3% | 41.7% | 4.33E−02 |
| hippocampus abundant gene transcript-like 2 (HIATL2) | NM_032318.1 | 0 | 4 | 8.3% | 41.7% | 4.33E−02 |
| bridging integrator 1 (BIN1) | NM_139348.1 | 0 | 4 | 8.3% | 41.7% | 4.33E−02 |
| similar to RIKEN cDNA 1700029115 (LOC143678) | XM_096472.2 | 0 | 4 | 8.3% | 41.7% | 4.33E−02 |

6.4 Association of SEREX and Protoarray Antigen Responses with Clinical Response in G-9803 and G-0010 GVAX Immunotherapy Trials for Prostate Cancer G-9803 (n=55 patients) and G-0010 (n=80 patients) are Phase II GVAX immunotherapy trials in chemotherapy-naïve patients with hormone-refractory prostate cancer (HRPC: FIGS. 3A and 3B).

The G-9803 study (FIG. 3A) included 2 different HRPC patient populations and 2 dose levels. In relation to HRPC patient populations, G-9803 enrolled PSA-rising and metastatic patients. Patients in the PSA-only group had increasing PSA levels but negative bone scan. Patients in the metastatic group had overt metastatic disease (positive bone scan, bidimensionally measurable disease, or both). All patients received a priming dose of $500 \times 10^6$ ($250 \times 10^6$ cells from each of PC3 and LNCaP cell lines). Patients in the PSA-only group and the first 24 patients in the metastatic group received the low dose (LD) boost of 100 million cells (50 million of each cell line). Since no dose limiting toxicities were seen at this dose level, a high dose (HD) of $300 \times 10^6$ cells ($150 \times 10^6$ of each cell line) was given to 10 additional patients in the metastatic group. Each cell type was injected intradermally in opposite limbs every 2 weeks for 6 months.

The G-0010 study enrolled metastatic HRPC patients only (FIG. 3B). The G-0010 study included 4 dose levels:

Dose Level 1: Each vaccination consisted of 2 intradermal injections of PC-3 cells to deliver a total of $50 \times 10^6$ cells, and 2 intradermal injections of LNCaP cells to deliver $50 \times 10^6$ cells, for a total of $100 \times 10^6$ cells per dose.

Dose Level 2: Each vaccination consisted of 3 intradermal injections of PC-3 cells to deliver a total of $100 \times 10^6$ cells, and 3 intradermal injections of LNCaP cells to deliver $100 \times 10^6$ cells, for a total of $200 \times 10^6$ cells per dose.

Dose Level 3: Each vaccination consisted of up to 6 intradermal injections of PC-3 cells to deliver $150 \times 10^6$ cells, and up to 6 intradermal injections of LNCaP cells to deliver $150 \times 10^6$ cells, for a total of $300 \times 10^6$ cells per dose.

Dose Level 4: The prime vaccination consisted of up to 10 intradermal injections of PC-3 cells to deliver $250 \times 10^6$ cells, and up to 10 intradermal injections of LNCaP cells to deliver $250 \times 10^6$ cells, for a total of $500 \times 10^6$ cells per dose. The boost vaccinations consisted of up to 6 intradermal injections of PC-3 cells to deliver $150 \times 10^6$ cells, and up to 6 intradermal injections of LNCaP cells to deliver $150 \times 10^6$ cells, for a total of $300 \times 10^6$ cells per dose.

The association between the induction of SEREX and ProtoArray identified antibodies with G98-03 and G-0010 patient survival using Kaplan-Meyer endpoint analysis was determined. As means of example, results for HLA-A24, OTUB2, FLJ14668, NNAT and Cardiolipin are presented.

6.4.1. Association of HLA-A24 A Response to Survival in GVAX-Treated Prostate Patients from the G-0010 Trial 6.4.1.1 Cloning Strategy for HLA-A24

HLA-A24 was cloned with a C-terminus Flag tag into a lentivirus plasmid vector, using a purchased HLA-A2402 plasmid clone (International Histocompatibility Working Group) to generate pKCCMVHLA-A24Flag (FIG. 4A). Briefly, HLA-A2402Flag was cloned by PCR attaching the Flag tag to the 3'end of the gene using the forward primers (5'-atatggatccatggccgtcatggcgccccg) (SEQ ID NO.: 24) and the reverse primer (5'-aatctccggacactttacaagtgtgagag) (SEQ ID NO.: 25) using the HLA-A2402 plasmid clone as s DNA PCR template. The PCR product was cleaned by Roche gel extraction kit, digested with BamH1 and BspE1, and ligated into identical sites in the parental vector pKCCMVNYESO1flag. The vector construct called pKC-CMVHLA-A2402Flag has been sequenced verified. SEQ ID NOS. 26 and 27 represent the HLA-A2402Flag amino acid and nucleotide sequence, respectively.

6.4.1.2 HLA-A2402Flag Protein Production

Flag-tagged HLA-A24 was produced in mammalian cells and purified using affinity purification. In brief, twenty-four hours before transfection, 10 75 cm$^2$ plates were seeded with 5×10$^6$ cells/plate HEK293 cells. Twenty-four hours later, cells were transfected with 10 μg/plate of pKCCMVHLA-A2402Flag using a calcium phosphate transfection kit (Clontech). Three days post-transfection cells were lysed with cell lysis buffer (+protease inhibitors) and HLA-A2402Flag protein purified using Anti-Flag M2 affinity columns (Sigma) according to manufacturing instructions.

6.4.1.3 Analysis of GVAX-Treated Patient Antibodies to HLA-A24 Using Western Blot For western analysis of patients antibodies to HLA-A24, 200 ng of purified HLA-A24 was separated on a Tris-Glycine gel (Invitrogen) under reducing conditions and transferred to a nitrocellulose membrane. Blots were then blocked overnight with 3% nonfat dry milk in TBS and incubated with a 1:500 dilution of G-0010 patients (n=65) serum post-GVAX therapy for 3 hours. Blots were then washed in TBST and incubated with an IgG/IgM specific donkey anti-human secondary antibody conjugated to horseradish peroxidase for an hour and a half. Following TBST washes immunoreactive bands were visualized by exposure of photographic film (Kodak) after the blots were treated with the ECL enhanced chemiluminescence system (Pierce). As shown in FIG. 4B, in patients 104, 302, 307 and 437 an immunoreactive band at 45 kDa running at the predicted molecular weight of HLA-A24Flag could be observed in the post-GVAX serum samples. Immunoreactivity to additional HLA-A alleles (produced as for HLA-A24) present in the GVAX immunotherapy for prostate cancer (HLA-A1 and A2) was only observed in 1 patient of 65 tested, patient 437. Immunostaining with an HRP-linked anti-FLAG monoclonal antibody demonstrates equal loading of all HLA-A proteins. Immunoreactivity was absent in pre-GVAX therapy samples (data not shown). Twenty-five HRPC patients who received a full course (9 cycles) of Docetaxel (taxotere) chemotherapy were also evaluated for HLA-A24 immunoreactivity over the course of treatment (pre- and post-taxotere) by western blot analysis. No patient induced a response over the course of therapy indicating the specificity of HLA-A24 antibody induction to GVAX immunotherapy for prostate cancer treated patients.

6.4.1.4 Association of HLA-A24 Immune Response and Survival

The association of HLA-A24 Ab response with survival was examined in the patients from the phase 2 G-0010 GVAX immunotherapy for prostate cancer trial, Patients were scored HLA-A24 antibody positive or negative dependent on western blot immunoreactivity and the potential association with survival analyzed using the Cox regression model, adjusted for prognostic factors and dose group (FIG. 4C). Data from all evaluable G-0010 pts demonstrate that induction of Ab to the PC-3-derived HLA-A24 is associated with survival. Among HLA-A24 haplotype negative pts, the HLA-A24 Ab-positive pts (n=30) had a median survival of 43 m vs. 18 m in Ab-negative pts (n=28), HR=0.53, p=0.04. Indicating a 47% reduction in hazard rate (HR) in those patients with HLA-A24 antibodies compared to those without antibodies, after controlling for the Halabi predicted survival.

6.4.2. Association of OTUB2 Ab Response to Survival in HRPC Patients Treated with GVAX Immunotherapy for Prostate Cancer Employing an ELISA based-assay for determining antibody titers, patients from G-9803 and G-0010 were evaluated for OTUB2 antibody titer induction post-GVAX immunotherapy. Purified OTUB2 protein (200 ng) was coated onto an ELISA plate and blocked with Superblock buffer for 2 hours. Patient serum both pre and post-GVAX immunotherapy was then added to the plates for 3 hours at room temperature. Following incubation, bound antibody was detected using a monkey anti-human IgG-HRP conjugate secondary antibody at 1:10,000 dilution. Induced antibody titers to OTUB2 were determined by dividing the well O.D. of the post-GVAX sample with the pre-GVAX O.D. to provide a fold-induction. Patients with a fold induction ≥2 fold, were considered positive for the survival analysis. An example of OTUB2 antibody induction in G-0010 patients is shown in FIG. 5A. Survival of those patients with induced Ab responses to OTUB2 were then compared to OTUB2 negative patients in G-0010 and G-9803. A survival advantage was observed in both trials. A representative survival analysis is shown in G-9803 PSA-rising HRPC patients. As shown in FIG. 5B, induction of antibodies to OTUB2 is associated with a 26.7 months longer survival in G-9803 patients. The correlation with survival in the PSA-rising population of G-9803 is also statistically significant (p=0.0266).

6.4.3. Association of FLJ14668 Ab Response to Survival in GVAX-Treated Prostate Patients from the G-0010 Trial 6.4.3.1 Cloning Strategy for FLJ14668

FLJ14668 was cloned with a C-terminus Flag tag into a lentivirus plasmid vector, using a purchased synthetically constructed FLJ14468Flag plasmid clone (GeneArt) to generate pKCCMV-FLJ14668Flag (FIG. 6A). Briefly, the FLJ14668Flag transgene was excised from the parental plasmid using EcoR1 and Sal1 restriction enzymes and ligated into identical sites in the parental vector pKCCMVp53flagdR1. The resulting vector construct, pKC-CMV-FLJ14668Flag, was sequenced verified. SEQ ID NOS. 28 and 29 represent the FLJ14668Flag amino acid and nucleotide sequence, respectively.

6.4.3.2 FLJ14668Flag Protein Production

Flag-tagged FLJ14668 was produced in mammalian cells and purified using affinity purification. In brief, twenty-four hours before transfection, 10 75 cm$^2$ plates were seeded with 5×10e6 cells/plate HEK293 cells. Twenty-four hours later, cells were transfected with 10 μg/plate of pKCCMV-FLJ14668Flag using a calcium phosphate transfection kit (Clontech). Three days post-transfection cells were lysed with cell lysis buffer (+protease inhibitors) and FLJ14668Flag protein purified using Anti-Flag M2 affinity columns (Sigma) according to manufacturing instructions.

6.4.3.3 Analysis of GVAX-Treated Patient Antibodies to FLJ14668 Using ELISA 96 well plates were coated with 250 ng well of purified FLJ14668 overnight in bicarbonate buffer (coating buffer). Next day, wells were washed with PBST and then blocked using 1% BSA in PBST for 3 hours at room temperature.

Following blocking, wells were washed in PBST and serum added at a 1:100 dilution in PBST+1% BSA. One and half hours post-serum addition, plates were washed and then incubated with a Donkey-anti Human IgG IgM HRP-conjugated secondary antibody (Jackson) diluted at 1:10,000 in POST for 1 hour at room temperature. Plates were then washed and bound secondary antibody detected using TBM (KPL). Plates were then read at 450 nm. To determine induction of an FLJ14668 antibody response, the post-GVAX O.D value was divided by the pre-GVAX O.D to determine a fold induction (FIG. 6B). Fold induction levels >2 were considered significant (as determined by normal controls). In comparison IgG/IgM antibodies to tetanus toxoid, a protein to which the majority of the population has been actively vaccinated to, was unchanged (pre/post ration <2) following GVAX-treatment indicating the increase in titer specific to FLJ14668 (FIG. 6C). Twenty-five HRPC patients who received a full course (9 cycles) of Docetaxel (taxotere) chemotherapy were also evaluated for FLJ14668 immunoreactivity over the course of treatment (pre- and post-taxotere) by ELISA. No patient induced a response over the course of therapy indicating the specificity of FLJ14668 antibody induction to GVAX immunotherapy for prostate cancer treated patients.

6.4.3.4 Association of FLJ14668Flag Immune Response and Survival in G-0010

The association of FLJ14668 Ab response with survival was examined in the patients from the phase 2 G-0010 GVAX immunotherapy for prostate cancer trial. Patients were scored FLJ14668 antibody positive or negative dependent on a fold induction of antibody titer >2 fold and the potential association with survival analyzed using the Cox regression model, adjusted for prognostic factors and dose group (FIG. 6D). Data from all evaluable G-0010 pts demonstrate that induction of Ab to the FLJ14668 is significantly associated with survival. Patients with an induction of antibody response to FLJ14668 protein (n=34) had a median survival of 43 m vs. 21 m in antibody negative pts (n=31), p=0.002.

The patients with FLJ14668 antibody had 66% V reduction in hazard rate (HR), compared to those patients antibody negative. Patient survival in FLJ14668 antibody positive and negative arms was also compared to predicted survival (as determined by the Halabi nomogram) in G-0010 by dose level (FIG. 6E). Results indicate that in all 3 G-0010 dose groups that survival was significantly increased over predicted in FLJ14668 seroconverters compared to those patients were an increase in FLJ14668 titer was not observed. Furthermore, the proportion of patients FLJ14668 antibody positive was dose-responsive comparing low, mid and high G-0010 dose groups (FIG. 6F).

6.4.4. Association of Neuronatin (NNAT) Ab Response to Survival in GVAX-Treated Prostate Patients from the G-0010 Trial 6.4.4.1 Cloning Strategy for NNAT NNAT was cloned with a C-terminus Flag tag into a lentivirus plasmid vector, using a purchased synthetically constructed NNATFlag plasmid clone (GeneArt) to generate pKCCMV-NNATFlag (FIG. 7A). Briefly, the NNATFlag transgene was excised from the parental plasmid using EcoR1 and Sal1 restriction enzymes and ligated into identical sites in the parental vector pKCCMVp53flagdR1. The resulting vector construct, pKCCMV-NNATFlag, was sequenced verified. SEQ ID NOS. 30 and 31 represent the NNATFlag amino acid and nucleotide sequence, respectively.

6.4.4.2 NNATFlag Protein Production

Flag-tagged NNAT was produced in mammalian cells and purified using affinity purification. In brief, twenty-four hours before transfection, 10 75 $cm^2$ plates were seeded with 5×10e6 cells/plate HEK293 cells. Twenty-four hours later, cells were transfected with 10 μg/plate of pKCCMV-NNAT-Flag using a calcium phosphate transfection kit (Clontech). Three days post-transfection cells were lysed with cell lysis buffer (+protease inhibitors) and NNATFlag protein purified using Anti-Flag M2 affinity columns (Sigma) according to manufacturing instructions.

6.4.4.3 Analysis of GVAX-Treated Patient Antibodies to NNAT Using ELSA 96 well plates were coated with 400 ng/well of purified NNAT overnight in bicarbonate buffer (coating buffer). Next day, wells were washed with PBST and then blocked using 1% BSA in PBST for 3 hours at room temperature. Following blocking, wells were washed in PBST and serum added at a 1:100 dilution in PBST+1% BSA. One and half hours post-serum addition, plates were washed and then incubated with a Donkey-anti Human IgG IgM HRP-conjugated secondary antibody (Jackson) diluted at 1:10,000 in PBS for 1 hour at room temperature. Plates were then washed and bound secondary antibody detected using TBM (KPL). Plates were then read at 450 nm. To determine induction of an NNAT antibody response, the post-GVAX O.D value was divided by the pre-GVAX O.D to determine a fold induction (FIG. 7B). Fold induction levels >2 were considered significant (as determined by normal controls). Twenty-five HRPC patients who received a full course (9 cycles) of Docetaxel (taxotere) chemotherapy were also evaluated for NNAT immunoreactivity, over the course of treatment (pre- and post-taxotere) by ELISA. No patient induced a response over the course of therapy indicating the specificity of NNAT antibody induction to GVAX immunotherapy for prostate cancer treated patients.

6.4.4.4 Association of NNATFlag Immune Response and Survival in G-0010

The association of NNAT Ab response with survival was examined in the patients from the phase 2 G-0010 GVAX immunotherapy for prostate cancer trial. Patients were scored NNAT antibody positive or negative dependent on a fold induction of antibody titer >2 fold and the potential association with survival analyzed using the Cox regression model, adjusted for prognostic factors and dose group (FIG. 7C). Data from all evaluable G-0010 pts demonstrate that induction of Ab to the NNAT is significantly associated with survival. Patients with an induction of antibody response to NNAT protein (n=48) had a median survival of 34 m vs. 10 m in antibody negative pts (n=17), p=<0.001.

The patients with NNAT antibody had 69% reduction in hazard rate (HR), compared to those patients antibody negative.

6.4.5. Antibody Response to Cardiolipin in GVAX-Treated Prostate Patients from the G-0010 Trial 6.4.5.1 Analysis of GVAX-Treated Patient Antibodies to Cardiolipin Using ELISA The induction of antibodies to cardiolipin were evaluated using a commercial kit (BioQuant). Briefly, patients serum diluted at 1:100 in PBST was added to wells coated with purified cardiolipin antigen. One and half hours post-serum addition, plates were washed 3×PBST and then incubated with enzyme-conjugated secondary antibody for 1 hour at room temperature. Plates were then washed and bound secondary antibody detected using TBM. Plates were then read at 450 nm. To determine induction of an cardiolipin antibody response, the post-GVAX O.D value was divided by the pre-GVAX O.D to determine a fold induction (FIG.

8A). Fold induction levels >2 were considered significant (as determined by normal controls). Twenty-five HRPC patients who received a full course (9 cycles) of Docetaxel (taxotere) chemotherapy were also evaluated for an increase in Cardiolipin antibody titer over the course of treatment (pre- and post-taxotere) by ELISA. No patient induced a response over the course of therapy indicating the specificity of Cardiolipin antibody induction to (VAX immunotherapy for prostate cancer treated patients.

6.4.5.2 Association of NNATFlag Immune Response and Survival in G-0010

The association of Cardiolipin Ab response with survival was examined in the patients from the phase 2 G-0010 GVAX immunotherapy for prostate cancer trial. Patients were scored Cardiolipin antibody positive or negative dependent on a fold induction of antibody titer >2 fold and the potential association with survival analyzed using the Cox regression model, adjusted for prognostic factors and dose group (FIG. 8B). Data from all evaluable G-0010 pts demonstrate that induction of Ab to the Cardiolipin is significantly associated with survival. Patients with an induction of antibody response to Cardiolipin protein (n=40) had a median survival of 38 m vs. 15 m in antibody negative pts (n=24), p=0.03. The patients with an increase in Cardiolipin antibody titer had 53% reduction in hazard rate (HR), compared to those no increase.

6.4.6. Antibody Response to SELS in GVAX-Treated Prostate Patients from the G-0010 Trial 6.4.6.1 Association of SELS Immune Response and Survival in G-0010

The association of SELS Ab response with survival was examined in the patients from the phase 2 G-0010 GVAX immunotherapy for prostate cancer trial. Patients were scored SELS antibody positive or negative dependent on a fold induction of antibody titer >2 fold and the potential association with survival analyzed using the Cox regression model, adjusted for prognostic factors and dose group (FIG. 14). Data from all evaluable G-0010 pts demonstrate that induction of Ab to the SELS is significantly associated with survival. Patients with an induction of antibody response to SELS protein (n=14) had a median survival of 51.9 m vs. 26.1 m in antibody negative pts (n=55), p=0.0273.

6.4.7. Antibody Response to HIGD2A in GVAX-Treated Prostate Patients from the G-0010 Trial 6.4.7.1 Association of HIGD2A Immune Response and Survival in G-0010

The association of HIGD2A Ab response with survival was examined in the patients from the phase 2 G-0010 GVAX immunotherapy for prostate cancer trial. Patients were scored HIGD2A antibody positive or negative dependent on a fold induction of antibody titer >2 fold and the potential association with survival analyzed using the Cox regression model, adjusted for prognostic factors and dose group (FIG. 15). Data from all evaluable G-0010 pts demonstrate that induction of Ab to the HIGD2A is significantly associated with survival. Patients with an induction of antibody response to HIGD2A protein (n=39) had a median survival of 32 m vs. 14.05 m in antibody negative pts (n=20), p=0.0179.

6.4.8. Antibody Response to SSR3 in GVAX-Treated Prostate Patients from the G-0010 Trial 6.4.8.1 Association of SSR3 Immune Response and Survival G-0010

The association of SSR3 Ab response with survival was examined in the patients from the phase 2 G-0010 GVAX immunotherapy for prostate cancer trial. Patients were scored SSR3 antibody positive or negative dependent on a fold induction of antibody titer >2 fold and the potential association with survival analyzed using the Cox regression model, adjusted for prognostic factors and dose group (FIG. 16). Data from all evaluable G-0010 pts demonstrate that induction of Ab to the SSR3 is significantly associated with survival. Patients with an induction of antibody response to SSR3 protein (n=34) had a median survival of 43.5 m vs. 19.4 m in antibody negative pts (n=28), p=0.0043.

6.4.9. Antibody Response to NRP2 in GVAX-Treated Prostate Patients from the G-0010 Trial 6.4.9.1 Association of NRP2 Immune Response and Survival in G-0010

The association of NRP2 Ab response with survival was examined in the patients from the phase 2 G-0010 GVAX immunotherapy for prostate cancer trial. Patients were scored NRP2 antibody positive or negative dependent on a fold induction of antibody titer >2 fold and the potential association with survival analyzed using the Cox regression model, adjusted for prognostic factors and dose group (FIG. 19). Data from all evaluable G-0010 pts demonstrate that induction of Ab to the NRP2 is significantly associated with survival. Patients with an induction of antibody response to NRP2 protein (n=36) had a median survival of 34 m vs. 21 m in antibody negative pts (n=33), p=0.0503.

6.4.10. Antibody Response to HLA-A24 and/or FLJ14668 in GVAX-Treated Prostate Patients from the G-0010 Trial In addition to single antigen/antibody analysis with survival, it is also possible to group antigens together to further define the association of immune response with clinical response. FIG. 9 demonstrates the association of being HLA-A24 and/or FLJ4668 antibody positive with survival in G-0010 patients. Patients with an induction of antibody response to HLA-A24 and/or FLJ14668 (n=41) had a median survival of 43.5 m vs. 14.2 m in patients negative for antibodies to both antigens (n=24), p=<0.001. The patients with antibodies to either antigen had a 55% reduction in hazard rate (HR), compared to those patients antibody negative for both antigens.

6.4.11. Antibody Response to NNAT and/or Cardiolipin in GVAX-Treated Prostate Patients from the G-0010 Trial FIG. 10 demonstrates the association of being NNAT and/or Cardiolipin antibody positive with survival in G-0010 patients. Patients with an induction of antibody response to NNAT and/or Cardiolipin (n=50) had a median survival of 32 m vs. 9.8 m in patients negative for antibodies to both antigens (n=14), p=<0.001.

6.4.12. Antibody Response to FLJ14668 and/or HLA-A24 and/or Cardiolipin in GVAX-Treated Prostate Patients from the G-0010 Trial In addition to single and double antibody analysis with survival, it is also possible to group three antigens together to further define the association of immune response with clinical response. FIG. 11 demonstrates the association of being FLJ14668 and/or HLA-A24 and/or Cardiolipin antibody positive with survival in G-0010 patients. Patients with an induction of antibody response to FLJ14668 and/or HLA-A24 and/or Cardiolipin (n=47) had a median survival of 34.8 m vs. 11.4 m in patients negative for antibodies to all three antigens (n=19), p=<0.0001. The patients with antibodies to either antigen had a 68% reduction in hazard rate (HR), compared to those patients antibody negative for all three antigens.

6.4.13. A Combination of HLA-A24 and OTUB2 Antibody Responses Provide a Correlation with Patient Survival Across Multiple GVAX Immunotherapy for Prostate Cancer Trials (G-0010 and G-9803)

Antibody responses to HLA-A24 and OTUB2 were then grouped together, given their correlation with survival as single antigens, to observe their ability to predict clinical outcome in G-0010 and G-9803 as a combination. The survival of patients who were OTUB2 and/or HLA-A24 antibody induction positive was compared to those patients negative for both responses. As shown in FIGS. 12A-12C, induction of antibodies to HLA-A24 and/or OUTB2 is associated with a statistically longer survival time in G-9803 metastatic HRPC patients (18 months increase in MST, p=0.0107, FIG. 12A), G-9803 PSA-rising HRPC patients (27.3 months increase in MST, p=0.0103, FIG. 12B) and G-0010 metastatic HRPC patients (20.1 months increase in MST, p<0.0001, FIG. 12C).

6.4.14. The Induction of HLA-A24, OTUB2 or FLJ14668 Immunoreactivity is Dose and Treatment Number Dependent in G-9803 and G-0010

We examined the impact of GVAX immunotherapy dose level in the G-0010 trial with the frequency of antibody responses to HLA-A24, OTUB2 and FLJ14668 (FIG. 13A). For all antigens examined, there was a step wise increase in the percentage of responding patients with increasing dose-level. The average number of treatments received in the antibody positive versus antibody negative arms of the G-0010 study were also compared for HLA-A24, OTUB2 and FLU 14668 FIG. 13B-13d). On average antibody-negative patients received 5.93, 5.6, 5.16 treatments for HLA-A24, OTUB2 and FLJ14668, respectively. In comparison, patients with an induced antibody response received 9.23, 9.62 and 9.44 treatments for HLA-A24, OTUB2 and FLJ14668, respectively (p<0.01 for all antigens).

6.5 Induction of Anti-Trp-2 and Gp100) Immune Responses in a Marine Melanoma Model Using Lentivirus Modified Lewis Lung Carcinoma Cells To evaluate whether a cell line can be genetically modified to induce an immune response to specific tumor-related antigens, preclinical studies were performed in the marine B16 melanoma model. In this model, treatment with irradiated whole melanoma tumor cells genetically modified to secrete GM-CSF was initially shown to generate specific and long lasting anti-tumor responses against a B16 tumor challenge. In these experiments the unrelated cell line, Lewis Lung Carcinoma (LLC), was modified to secrete GM-CSF and over-express either of the two antigens Trp2 (LLC.GMKd.Trp2) or gp100 (LLC.GMKd.gp100) or both (LLC.GMKd.Trp2/gp100). Trp2 and gp100 each serve as melanoma target antigens that were previously identified to be involved in the immune-mediated rejection of B16 murine tumors. Lentiviral vectors encoding Trp2 or gp100 under the control of the CMV promoter were constructed according to standard molecular techniques. LLC cells were then transduced with lenti-Trp2 and/or gp100 and cell populations analyzed for antigen expression (FIG. 20). Analysis of the modified LLC cell lines by FAC and PCR indicate Trp2 and gp100 protein (FIG. 20A) and RNA expression FIG. 20B).

The B16 murine model was then used to evaluate the capability of the LLC.GMKd.gp100, and LLC.GMKd.Trp2 cells to induce an antigen: specific immune response. C57BL/6 animals were challenged with a lethal dose of 2×10E5 B16F10 cells. Three days post-challenge animals were immunized with 3×10E6 allogeneic GM-CSF-secreting B16F10 cells (B16F10.GMKd) as a multivalent antigen immunotherapy or with GM-CSF-secreting LLC cells modified to over-express either of the two B16-associated antigens Trp2 (LLC.GMKd.Trp2) or gp100 (LLC.GMKd.gp100) as single B16 antigen-specific immunotherapies. Seven days after immunotherapy, spleens (n=5/group) were removed and an ELISPOT assay was performed to evaluate the number of activated, IFN-γ secreting T-cells per 1×10E6 splenocytes when stimulated for 24 hours with peptides derived from the B16-associated antigens Trp2 or gp100, (FIG. 21). Results demonstrated that in comparison to the control treated mice, the genetically modified LLC cell lines LLC.GMKd.Trp2 and LLC.GMkd.gp100 induced Trp-7 and gp100 specific immune responses, respectively.

The ability of modified LLC cells LLC.GMKd.Trp2 and LLC.GMKd.Trp2/gp100 to extend survival was then examined in the C57BL/6 B16F10 melanoma model. Animals were immunized on day 0 with 3×10E6 immunotherapy cells and challenged 7 day's later with a lethal dose of live B16F10 cells. Compared to HBSS injected control mice, unmodified LLC.GMKd cells provided modest protection in the B16 tumor model (FIG. 22). Anti-tumor protection was increased further by the use of LLC.GMKd.Trp2 and more significantly with the double antigen expressing LLC.GM-Kd.Trp2/gp100 immunotherapy (p=<0.01) with 90% of animals surviving long-term (70) day post-challenge).

6.6 Evaluation of Anti-Tumor Efficacy of Immunotherapy with Proliferation Incompetent Tumor Cells that Express GM-CSF and a Prostate Tumor-Associated Antigen The following provides exemplary methods for demonstrating that immunotherapy with cells genetically modified to express GM-CSF and one or more prostate tumor-associated antigens, e.g., HLA-A24, FLJ14668, Cardiolipin, NNAT, SELS, HIGD2A, SSR3, NRP2, etc. leads to enhanced anti-tumor efficacy relative to immunotherapy with cells genetically modified to express GM-CSF or the one or more prostate tumor-associated antigens alone, as described herein.

An autologous, allogeneic or bystander cell line is modified to express a cytokine, e.g., GM-CSF, and one or more prostate tumor-associated antigens, e.g., HLA-A24, FLJ14668, Cardiolipin, NNAT, SELS, HIGD2A, SSR3, NRP2, etc., or a murine homolog thereof. The antigens are cloned into a mammalian based expression vector (e.g., a lentiviral expression plasmid) according to standard molecular techniques. The cell line is transduced with expression vectors for the one or more antigens and cytokine, if not already transduced with a cytokine expression vector, and analyzed for cytokine and antigen expression using standard techniques in the art, e.g. FACS, western blot, qRT-PCR, etc.

A murine mouse model, e.g., B16F10, is used to evaluate the antigen specific tumor response. Animals are challenged with a lethal dose of tumor cells. e.g., 2×10E5 B116F10 cells. Three days post-challenge, the animals are immunized with cells genetically modified to express cytokine, e.g., GM-CSF, alone, or cytokine and one or more prostate tumor associated antigens (or a murine homolog thereof). Seven days after immunotherapy, animals are evaluated for antigen specific immune responses, e.g. IFN-γ secreting T-cells, pro-inflammatory cytokine secretion, effector CD8 T-cell infiltration into tumors, and the like.

A murine mouse model, e.g., B16F10, is also used to evaluate anti-tumor efficacy in response to immunotherapy with cells genetically modified to express a cytokine, e.g., GM-CSF and one or more prostate tumor-associated antigens (or a murine homolog thereof). Animals are immunized on day 0 with immunotherapy with cells genetically modified to express a cytokine, e.g., GM-CSF, one or more prostate tumor-associated antigens alone, or a cytokine and one or more prostate tumor-associated antigens. 7 days after immunotherapy, animals are given a lethal dose of live tumor cells. Animals are monitored twice weekly for the development of subcutaneous tumors and euthanize when tumors become necrotic or exceed 1500 mm3 in volume.

REFERENCES

Casiano C A, Mediavilla-Varela M, Tan E M. Tumor-associated antigen arrays for the serological diagnosis of cancer. Mol Cell Proteomics. 2006 October; 5(10):174559, Epub 2006 May 29, Review. PMID: 16733262.

Bradford T S, Wang X, Chinnaiyan A M. Cancer immunomics: using autoantibody signatures in the early detection of prostate cancer. Urol Oncol. 2006 May-June; 24(3):237-42. PMID: 16678056, Qin S, Qiu W, Ehrlich J R, Ferdinand A S, Richie J P, O'leary M P, Lee M L, Liu B C. Development of a "reverse capture" autoantibody microarray for studies of antigen-autoantibody profiling. Proteomics. 2006 Apr. 5.

Wang X, Yu J, Sreekumar A, Varambally S, Shen R, Giacherio D, Mebra R, Montie J E, Pienta K J, Sanda M G, Kantoff P W, Rubin M A, Wei J T, Ghosh D, Chinnaiyan A M. Autoantibody signatures in prostate cancer, N Engl J Med. 2005 Sep. 22; 353(12): 1224-35.

Dunphy E J, McNeel D W. Antigen-specific IgG elicited in subjects with prostate cancer treated with flt3 ligand. J Immunother. 2005 May-June; 28(3):268-75.

McNeel D G, Nguyen L D, Storer B E, Vessella R, Lange P H, Disis M L. Antibody immunity to prostate cancer associated antigens can be detected in the serum of patients with prostate cancer. J Urol. 2000 November; 164(5):1825-9.

Sahin U. Tureci O, Schmitt H. Cochlovius B, Johannes T, Schmits R, Stenner F, Lao G, Schobert I, Pfreundschuh M. Human neoplasms elicit multiple specific immune responses in the autologous host. Proc Natl Acad Sci USA. 1995 Dec. 5; 92(25):11810-3.

Varambally S, Yu J, Laxman B, Rhodes D R, Mehra R, Tomlins S A, Shah R B, Chandran U, Montzon F A, Becich M J, Wei J T, Pienta K J, Ghosh D, Rubin M A, Chinnaiyan A M. Integrative genomic and proteomic analysis of prostate cancer reveals signatures of metastatic progression. Cancer Cell. 2005 November; 8(5):393-406.

Halabi, et al. Prognostic model for predicting survival in men with HRPC: Journal of Clinical Oncology, 2003; 21(7): 1232-7

While many specific examples have been provided, the above description is intended to illustrate rather than limit the invention. Many variations of the invention will become apparent to those skilled in the art upon review of this specification. The scope of the invention should, therefore, be determined not with reference to the above description, but instead should be determined with reference to the appended claims along with their full scope of equivalents.

All sequences referenced by accession number, publications, and patent documents cited in this application are incorporated by reference in their entirety for all purposes to the same extent as if each individual publication or patent document were so individually denoted. Citation of these documents is not an admission that any particular reference is "prior art" to this invention.

What is claimed is:

1. An in vitro composition comprising one or more populations of cells genetically modified to express the coding sequence of granulocyte-macrophage colony stimulating factor ("GM-CSF") and the coding sequence of one or more prostate tumor-associated antigens selected from the group consisting of HLA-A24, FLJ14668 (SEQ ID NO: 3), NNAT, SELS, HIGD2A, SSR3 and NRP2, wherein the genetically modified cells comprise prostate tumor cells, bystander cells, or both prostate tumor cells and bystander cells.

2. The composition of claim 1, wherein the prostate tumor-associated antigen is FLJ14668 (SEQ ID NO.: 3).

3. The composition of claim 1, wherein the one or more populations of cells genetically modified to express the coding sequence for GM-CSF and one or more prostate tumor-associated antigens selected from the group consisting of HLA-A24, FLJ14668 (SEQ ID NO.: 3), NNAT, SELS, HIGD2A, SSR3 and NRP2 is a single cell population.

4. The composition of claim 1, wherein the one or more populations of cells genetically modified to express the coding sequence for GM-CSF and one or more prostate tumor-associated antigens selected from the group consisting of HLA-A24, FLJ14668 (SEQ ID NO.: 3), NNAT, SELS, HIGD2A, SSR3 and NRP2 comprises at least two distinct cell populations.

5. The composition of claim 1, wherein the genetically modified cells are prostate tumor cells.

6. The composition of claim 1, wherein the genetically modified cells are bystander cells.

* * * * *

SEQUENCE LISTING

```
<160> NUMBER OF SEQ ID NOS: 33

<210> SEQ ID NO 1
<211> LENGTH: 365
<212> TYPE: PRT
<213> ORGANISM: Homo sapiens

<400> SEQUENCE: 1

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Ser Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Tyr Asn Gln Ser
            100                 105                 110

Glu Ala Gly Ser His Thr Leu Gln Met Met Phe Gly Cys Asp Val Gly
        115                 120                 125

Ser Asp Gly Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
```

```
                145                 150                 155                 160
Asp Met Ala Ala Gln Ile Thr Lys Arg Lys Trp Glu Ala Ala His Val
                    165                 170                 175
Ala Glu Gln Gln Arg Ala Tyr Leu Glu Gly Thr Cys Val Asp Gly Leu
                    180                 185                 190
Arg Arg Tyr Leu Glu Asn Gly Lys Glu Thr Leu Gln Arg Thr Asp Pro
                195                 200                 205
Pro Lys Thr His Met Thr His His Pro Ile Ser Asp His Glu Ala Thr
        210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                    245                 250                 255
Thr Arg Pro Ala Gly Asp Gly Thr Phe Gln Lys Trp Ala Ala Val Val
                260                 265                 270
Val Pro Ser Gly Glu Glu Gln Arg Tyr Thr Cys His Val Gln His Glu
            275                 280                 285
Gly Leu Pro Lys Pro Leu Thr Leu Arg Trp Glu Pro Ser Ser Gln Pro
        290                 295                 300
Thr Val Pro Ile Val Gly Ile Ile Ala Gly Leu Val Leu Leu Gly Ala
305                 310                 315                 320
Val Ile Thr Gly Ala Val Val Ala Val Met Trp Arg Arg Asn Ser
                325                 330                 335
Ser Asp Arg Lys Gly Gly Ser Tyr Ser Gln Ala Ala Ser Ser Asp Ser
                340                 345                 350
Ala Gln Gly Ser Asp Val Ser Leu Thr Ala Cys Lys Val
                355                 360                 365

<210> SEQ ID NO 2
<211> LENGTH: 1095
<212> TYPE: DNA
<213> ORGANISM: Homo sapiens

<400> SEQUENCE: 2
atggccgtca tggcgcccccg aaccctcgtc ctgctactct cgggggccct ggccctgacc      60
cagacctggg caggctccca ctccatgagg tatttctcca catccgtgtc ccggcccggc     120
cgcggggagc cccgcttcat cgccgtgggc tacgtggacg acacgcagtt cgtgcggttc     180
gacagcgacg ccgcgagcca gaggatggag ccgcgggcgc cgtggataga gcaggagggg     240
ccggagtatt gggacgagga cagggaaa gtgaaggccc actcacagac tgaccgagag     300
aacctgcgga tcgcgctccg ctactacaac cagagcgagg ccggttctca caccctccag     360
atgatgtttg gctgcgacgt ggggtcggac ggcgcttcc tccgcgggta ccaccagtac     420
gcctacgacg gcaaggatta tatcgccctg aaagaggacc tgcgctcttg gaccgcggcg     480
gacatggcgg ctcagatcac caagcgcaag tgggaggcgg cccatgtggc ggagcagcag     540
agagcctacc tggagggcac gtgcgtggac gggctccgca gatacctgga gaacgggaag     600
gagacgctgc agcgcacgga ccccccccaag acacatatga cccaccaccc catctctgac     660
catgaggcca ctctgagatg ctgggccctg ggcttctacc ctgcggagat cacactgacc     720
tggcagcggg atggggagga ccagacccag gacacggagc ttgtggagac caggcctgca     780
ggggatggaa ccttccagaa gtgggcagct gtggtggtac cttctggaga ggagcagaga     840
tacacctgcc atgtgcagca tgagggtctg cccaagcccc tcaccctgag atgggagcca     900
```

```
tcttcccagc ccaccgtccc catcgtgggc atcattgctg gcctggttct ccttggagct    960
gtgatcactg gagctgtggt cgctgctgtg atgtggagga ggaacagctc agatagaaaa   1020
ggagggagct actctcaggc tgcaagcagt gacagtgccc agggctctga tgtgtctctc   1080
acagcttgta aagtg                                                    1095
```

<210> SEQ ID NO 3
<211> LENGTH: 138
<212> TYPE: PRT
<213> ORGANISM: Homo sapiens

<400> SEQUENCE: 3

```
Met Ala Glu Leu Gln Gln Leu Arg Val Gln Glu Ala Met Glu Ser Met
1               5                   10                  15

Val Lys Ser Leu Glu Arg Glu Asn Ile Arg Lys Met Gln Gly Leu Met
            20                  25                  30

Phe Arg Cys Ser Ala Ser Cys Cys Glu Asp Ser Gln Ala Ser Met Lys
        35                  40                  45

Gln Val His Gln Cys Ile Glu Arg Cys His Val Pro Leu Ala Gln Ala
    50                  55                  60

Gln Ala Leu Val Thr Ser Glu Leu Glu Lys Phe Gln Asp Arg Leu Ala
65                  70                  75                  80

Arg Cys Thr Met His Cys Asn Asp Lys Ala Lys Asp Ser Ile Asp Ala
                85                  90                  95

Gly Ser Lys Glu Leu Gln Val Lys Gln Gln Leu Asp Ser Cys Val Thr
            100                 105                 110

Lys Cys Val Asp Asp His Met His Leu Ile Pro Thr Met Thr Lys Lys
        115                 120                 125

Met Lys Glu Ala Leu Leu Ser Ile Gly Lys
    130                 135
```

<210> SEQ ID NO 4
<211> LENGTH: 1786
<212> TYPE: DNA
<213> ORGANISM: Homo sapiens

<400> SEQUENCE: 4

```
gtacgccgat tccatatggg cgccggcgcg gagcgccgcg gggcagcgcg gggtcgccat     60
ggctgagctg cagcagctcc gggtgcagga ggcgatggag tccatggtga agagtctgga    120
aagagagaac atccggaaga tgcagggtct catgttccgg tgcagcgcca gctgttgtga    180
ggacagccag gcctccatga agcaggtgca ccagtgcatc gagcgctgcc atgtgcctct    240
ggctcaagcc caggctttgg tcaccagtga gctggagaag ttccaggacc gcctggcccg    300
gtgcaccatg cattgcaatg acaaagccaa agattcaata gatgctggga gtaaggagct    360
tcaggtgaag cagcagctgg acagttgtgt gaccaagtgt gtggatgacc acatgcacct    420
catcccaact atgaccaaga agatgaagga ggctctctta tcaattggaa aataaaagta    480
tttgccagtg gccatcaggc tgagggcaag aatatatttt ttataaggaa ttgggaattt    540
tagtctttta agcaaagttt acgaatgaag aaatgaagga tggccacaag cgtaaggcat    600
atgtcacttg cctctggaca ctggttattt tatgtttcag tccctaaaaa atgaaatgga    660
aaaaagtggt gctaaatcga gtcagagata ttacaggaga gttttagagc ttattatttc    720
ctgtggccag tgcttgtcct ggcagtaagg ctctcccctg taacaagcca gagccctcca    780
aggtaccaga ctcttcttac tacacaggta ctaacaggct ggcaggttag agttggtgga    840
```

```
gtctgaggag agatattttc tctttgttgc caacatcctg tttaccaaaa gtgtcacccc      900
accatcttcc ataagctgtg aaacaaaatc aatgaggtca ctaacttaga agggaaagaa      960
agttttctgg gtctttgttt tcttgatttg gggtaattta tacaagggca tacaagttga     1020
ttttaagatg tggaactggg aggtagacta gtttggataa gaactttgaa atgttccttg     1080
tggatcccca tttctggtca tcaagatgtg gatgtacatt tcttaaaatt attacatgct     1140
gcatctttca gcctggagac tgtgcagaaa catgagaggt gatgacacac taattatggg     1200
aagcagaatt actggctgat ggcccctgag gctgtgtgta acaaaatgac aggacaatct     1260
tgcagtaaca ctttcccctt gaagagaagg gggttttgat tgtgatatat actagtatct     1320
aggaatgaac agtaaaagag gagcagttgg ctacttgatt acaacagagt aaatgaagta     1380
ctggatttgg gaaaacctgg ttttattaga acatatggaa tgaaagccta cacctagcat     1440
tgcctactta gcccctgaa ttaacagagc ccaattgaga caaacccctg caacaggaa      1500 attcaaggga gaaaagtaa gcaacttggg ctaggatgag ctgactccct tagagcaaag     1560
gagagacagc ccccattacc aaataccatt tttgcctggg gcttgtgcag ctggcagtgt     1620 tcctgccca gcatggcacc ttattgtttt gatagcaact tcgttgaatt ttcaccaact     1680
tattacttga aattataata tagcctgtcc gtttgctgtt tccaggctgt gatatatttt     1740
cctagtggtt tgactttaaa aataaataag gtttaatttt ctcccc                   1786

<210> SEQ ID NO 5
<211> LENGTH: 106
<212> TYPE: PRT
<213> ORGANISM: Homo sapiens

<400> SEQUENCE: 5

Met Ala Thr Pro Gly Pro Val Ile Pro Glu Val Pro Phe Glu Pro Ser
1               5                   10                  15

Lys Pro Pro Val Ile Glu Gly Leu Ser Pro Thr Val Tyr Arg Asn Pro
            20                  25                  30

Glu Ser Phe Lys Glu Lys Phe Val Arg Lys Thr Arg Glu Asn Pro Val
        35                  40                  45

Val Pro Ile Gly Cys Leu Ala Thr Ala Ala Leu Thr Tyr Gly Leu
    50                  55                  60

Tyr Ser Phe His Arg Gly Asn Ser Gln Arg Ser Gln Leu Met Met Arg
65                  70                  75                  80

Thr Arg Ile Ala Ala Gln Gly Phe Thr Val Ala Ala Ile Leu Leu Gly
                85                  90                  95

Leu Ala Val Thr Ala Met Lys Ser Arg Pro
            100                 105

<210> SEQ ID NO 6
<211> LENGTH: 628
<212> TYPE: DNA
<213> ORGANISM: Homo sapiens

<400> SEQUENCE: 6
cggagtcccg attttctcct gctgctgtgg cccggacatg gcgactcccg gccctgtgat        60
tccggaggtc ccctttgaac catcgaagcc tccagtcatt gagggctga gccccactgt       120 ttacaggaat ccagagagtt tcaaggaaaa gttcgttcgc aagacccgcg agaacccggt       180
ggtacccata ggttgcctgg ccacggcggc cgccctcacc tacggcctct actccttcca       240
ccggggcaac agccagcgct ctcagctcat gatgcgcacc cggatcgccg cccagggttt       300
```

```
cacggtcgca gccatcttgc tgggtctggc tgtcactgct atgaagtctc gaccctaagc    360
ccagggtctg gccttgaaag ctccgcagaa atgattccaa aacccaggga gcaaccactg    420
gccctaccgt gggacttact ccctcctctc ctttgagagg cccatgtgtc gctggggagg    480
aagtgacccc ttgtgtaact gtaaccgaaa gttttttcaa aaatcctaga tgctgttgtt    540
tgaatgttac atacttctat ttgtgccaca tctcccctcc actccctgc ttaataaact     600 ctaaaaatcc aaaaaaaaaa aaaaaaa                                        628
```

<210> SEQ ID NO 7
<211> LENGTH: 81
<212> TYPE: PRT
<213> ORGANISM: Homo sapiens

<400> SEQUENCE: 7

```
Met Ala Ala Val Ala Ala Ala Ser Ala Glu Leu Leu Ile Ile Gly Trp
1               5                   10                  15

Tyr Ile Phe Arg Val Leu Leu Gln Val Phe Leu Glu Cys Cys Ile Tyr
            20                  25                  30

Trp Val Gly Phe Ala Phe Arg Asn Pro Pro Gly Thr Gln Pro Ile Ala
        35                  40                  45

Arg Ser Glu Val Phe Arg Tyr Ser Leu Gln Lys Leu Ala Tyr Thr Val
    50                  55                  60

Ser Arg Thr Gly Arg Gln Val Leu Gly Glu Arg Arg Gln Arg Ala Pro
65                  70                  75                  80

Asn
```

<210> SEQ ID NO 8
<211> LENGTH: 1338
<212> TYPE: DNA
<213> ORGANISM: Homo sapiens

<400> SEQUENCE: 8

```
taggtggcgg gcgggtactt aaggcgcggc caccgcggct gcggcagtgc gcccaacagc     60
ggactccgag accagcggat ctcggcaaac cctctttctc gaccacccac ctaccattct    120
tggaaccatg gcggcagtgg cggcggcctc ggctgaactg ctcatcatcg gctggtacat    180
cttccgcgtg ctgctgcagg tgttcctgga atgctgcatt tactgggtag gattcgcttt    240
tcgaaatcct ccagggacac agcccattgc gagaagtgag gtgttcaggt actccctgca    300
gaagctggca tacacggtgt cgcggaccgg gcggcaggtg ttgggggagc gcaggcagcg    360
agcccccaac tgaggcccca gctcccagcc ctgggcggcc gtatcatcag gtgctcctgt    420
gcatctcggc cagcacggga gccagtgccg cgcaggaatg tggggtcccc tgtgttccct    480
cgccagagga gcacttggca aggtcagtga ggggccagta gaccccggga gaagcagtac    540
cgacaatgac gaagatacca gatcccttcc caaccccttt gcaccggtcc cactaagggg    600
cagggtcgag agaggagggg ggatagggg agcagacccc tgagatctgg gcataggcac    660
cgcattctga tctggacaaa gtcgggacag caccatccca gccccgaagc cagggccatg    720
ccagcaggcc ccaccatgga aatcaaaaca ccgcaccagc cagcagaatg gacattctga    780
catcgccagc cgacgccctg aatcttggtg cagcaccaac cgcgtgcctg tgtgcgggga    840
ctggagggca cagttgagga aggagggtgg ttaagaaata cagtggggcc ctctcgctgt    900
cccttgccca gggcacttgc attccagcct cgctgcattt gctctctcga ttccccttc    960 ctcctcactg cctcccaagc ccacccctact ccaaaataat gtgtcacttg atttggaact   1020
```

| attcaagcag taaaagtaaa tgaatcccac ctttactaaa acactttctc tgaacccccc | 1080 |
| ttgcccctca ctgatcttgc ttttccctgg tctcatgcag ttgtggtcaa tattgtggta | 1140 |
| atcgctaatt gtactgattg tttaagtgtg cattagttgt gtctcccag ctagattgta | 1200 |
| agctcctgga ggacagggac cacctctaca aaaataaaa aaagtacctc ccctgtctcg | 1260 |
| cacagtgtcc caggaccctg cggtgcagta gaggcgcacc aaaaaaaaaa aaaaaaaaaa | 1320 |
| aaaaaaaaaa aaaaaaaa | 1338 |

<210> SEQ ID NO 9
<211> LENGTH: 185
<212> TYPE: PRT
<213> ORGANISM: Homo sapiens

<400> SEQUENCE: 9

Met Ala Pro Lys Gly Ser Ser Lys Gln Gln Ser Glu Glu Asp Leu Leu
1               5                   10                  15

Leu Gln Asp Phe Ser Arg Asn Leu Ser Ala Lys Ser Ser Ala Leu Phe
            20                  25                  30

Phe Gly Asn Ala Phe Ile Val Ser Ala Ile Pro Ile Trp Leu Tyr Trp
        35                  40                  45

Arg Ile Trp His Met Asp Leu Ile Gln Ser Ala Val Leu Tyr Ser Val
    50                  55                  60

Met Thr Leu Val Ser Thr Tyr Leu Val Ala Phe Ala Tyr Lys Asn Val
65                  70                  75                  80

Lys Phe Val Leu Lys His Lys Val Ala Gln Lys Arg Glu Asp Ala Val
                85                  90                  95

Ser Lys Glu Val Thr Arg Lys Leu Ser Glu Ala Asp Asn Arg Lys Met
            100                 105                 110

Ser Arg Lys Glu Lys Asp Glu Arg Ile Leu Trp Lys Lys Asn Glu Val
        115                 120                 125

Ala Asp Tyr Glu Ala Thr Thr Phe Ser Ile Phe Tyr Asn Asn Thr Leu
    130                 135                 140

Phe Leu Val Val Val Ile Val Ala Ser Phe Phe Ile Leu Lys Asn Phe
145                 150                 155                 160

Asn Pro Thr Val Asn Tyr Ile Leu Ser Ile Ser Ala Ser Ser Gly Leu
                165                 170                 175

Ile Ala Leu Leu Ser Thr Gly Ser Lys
            180                 185

<210> SEQ ID NO 10
<211> LENGTH: 555
<212> TYPE: DNA
<213> ORGANISM: Homo sapiens

<400> SEQUENCE: 10

| atggctccta aaggcagctc caaacagcag tctgaggagg acctgctcct gcaggatttc | 60 |
| agccgcaatc tctcggccaa gtcctccgcg ctcttcttcg gaaacgcgtt catcgtgtct | 120 |
| gccatcccca tctggttata ctggcgaata tggcatatgg atcttattca gtctgctgtt | 180 |
| ttgtatagtg tgatgaccct agtaagcaca tatttggtag cctttgcata caagaatgtg | 240 |
| aaatttgttc tcaagcacaa agtagcacag aagagggagg atgctgtttc caagaagtg | 300 |
| actcgaaaac tttctgaagc tgataataga aagatgtctc ggaaggagaa agatgaaaga | 360 |
| atcttgtgga gaagaatga agttgctgat tatgaagcta aacattttc catcttctat | 420 |
| aacaacactc tgttcctggt cgtggtcatt gttgcttcct tcttcatatt gaagaacttc | 480 |

```
aaccccacag tgaactacat attgtccata agtgcttcat caggactcat cgccctcctg    540
tctactggct ccaaa                                                     555

<210> SEQ ID NO 11
<211> LENGTH: 187
<212> TYPE: PRT
<213> ORGANISM: Homo sapiens

<400> SEQUENCE: 11

Met Glu Arg Gln Glu Ser Leu Ser Ala Arg Pro Ala Leu Glu Thr
1               5                   10                  15

Glu Gly Leu Arg Phe Leu His Thr Thr Val Gly Ser Leu Leu Ala Thr
            20                  25                  30

Tyr Gly Trp Tyr Ile Val Phe Ser Cys Ile Leu Leu Tyr Val Val Phe
        35                  40                  45

Gln Lys Leu Ser Ala Arg Leu Arg Ala Leu Arg Gln Arg Gln Leu Asp
    50                  55                  60

Arg Ala Ala Ala Val Glu Pro Asp Val Val Lys Arg Gln Glu
65                  70                  75                  80

Ala Leu Ala Ala Ala Arg Leu Lys Met Gln Glu Glu Leu Asn Ala Gln
                85                  90                  95

Val Glu Lys His Lys Glu Lys Leu Lys Gln Leu Glu Glu Lys Arg
            100                 105                 110

Arg Gln Lys Ile Glu Met Trp Asp Ser Met Gln Glu Gly Lys Ser Tyr
        115                 120                 125

Lys Gly Asn Ala Lys Lys Pro Gln Glu Glu Asp Ser Pro Gly Pro Ser
    130                 135                 140

Thr Ser Ser Val Leu Lys Arg Lys Ser Asp Arg Lys Pro Leu Arg Gly
145                 150                 155                 160

Gly Gly Tyr Asn Pro Leu Ser Gly Glu Gly Gly Ala Cys Ser Trp
                165                 170                 175

Arg Pro Gly Arg Arg Gly Pro Ser Ser Gly Gly
            180                 185

<210> SEQ ID NO 12
<211> LENGTH: 561
<212> TYPE: DNA
<213> ORGANISM: Homo sapiens

<400> SEQUENCE: 12
atggaacgcc aagaggagtc tctgtccgcg cggccggccc tggagaccga ggggctgcgc    60
ttcctgcaca ccacggtggg ctccctgctg ccacctatg gctggtacat cgtcttcagc    120
tgcatccttc tctacgtggt ctttcagaag ctttccgccc ggctaagagc cttgaggcag    180
aggcagctgg accgagctgc ggctgctgtg gaacctgatg ttgttgttaa cgacaagaa    240 gctttagcag ctgctcgact gaaaatgcaa gaagaactaa atgcgcaagt tgaaaagcat    300
aaggaaaaac tgaaacaact tgaagaagaa aaaggagac agaagattga atgtgggac    360 agcatgcaag aaggaaaaag ttacaaagga aatgcaaaga agccccagga ggaagacagt    420
cctgggcctt ccacttcatc tgtcctgaaa cggaaatcgg acagaaagcc tttgcgggga    480
ggaggttata acccgttgtc tggtgaagga ggcggagctt gctcctggag acctggacgc    540
agaggcccgt catctggcgg a                                              561

<210> SEQ ID NO 13
```

<211> LENGTH: 926
<212> TYPE: PRT
<213> ORGANISM: Homo sapiens

<400> SEQUENCE: 13

```
Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Val Val Leu Asn Lys Leu His Ala
```

-continued

```
           385                 390                 395                 400
Pro Leu Thr Arg Phe Val Arg Ile Arg Pro Gln Thr Trp His Ser
                405                 410                 415
Gly Ile Ala Leu Arg Leu Glu Leu Phe Gly Cys Arg Val Thr Asp Ala
                420                 425                 430
Pro Cys Ser Asn Met Leu Gly Met Leu Ser Gly Leu Ile Ala Asp Ser
                435                 440                 445
Gln Ile Ser Ala Ser Ser Thr Gln Glu Tyr Leu Trp Ser Pro Ser Ala
    450                 455                 460
Ala Arg Leu Val Ser Ser Arg Ser Gly Trp Phe Pro Arg Ile Pro Gln
465                 470                 475                 480
Ala Gln Pro Gly Glu Glu Trp Leu Gln Val Asp Leu Gly Thr Pro Lys
                485                 490                 495
Thr Val Lys Gly Val Ile Ile Gln Gly Ala Arg Gly Gly Asp Ser Ile
                500                 505                 510
Thr Ala Val Glu Ala Arg Ala Phe Val Arg Lys Phe Lys Val Ser Tyr
                515                 520                 525
Ser Leu Asn Gly Lys Asp Trp Glu Tyr Ile Gln Asp Pro Arg Thr Gln
    530                 535                 540
Gln Pro Lys Leu Phe Glu Gly Asn Met His Tyr Asp Thr Pro Asp Ile
545                 550                 555                 560
Arg Arg Phe Asp Pro Ile Pro Ala Gln Tyr Val Arg Val Tyr Pro Glu
                565                 570                 575
Arg Trp Ser Pro Ala Gly Ile Gly Met Arg Leu Glu Val Leu Gly Cys
                580                 585                 590
Asp Trp Thr Asp Ser Lys Pro Thr Val Glu Thr Leu Gly Pro Thr Val
                595                 600                 605
Lys Ser Glu Glu Thr Thr Thr Pro Tyr Pro Thr Glu Glu Ala Thr
    610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Leu Glu Glu Pro Cys Gly
                645                 650                 655
Trp Met Tyr Asp His Ala Lys Trp Leu Arg Thr Thr Trp Ala Ser Ser
                660                 665                 670
Ser Ser Pro Asn Asp Arg Thr Phe Pro Asp Asp Arg Asn Phe Leu Arg
                675                 680                 685
Leu Gln Ser Asp Ser Gln Arg Glu Gly Gln Tyr Ala Arg Leu Ile Ser
    690                 695                 700
Pro Pro Val His Leu Pro Arg Ser Pro Val Cys Met Glu Phe Gln Tyr
705                 710                 715                 720
Gln Ala Thr Gly Gly Arg Gly Val Ala Leu Gln Val Val Arg Glu Ala
                725                 730                 735
Ser Gln Glu Ser Lys Leu Leu Trp Val Ile Arg Glu Asp Gln Gly Gly
                740                 745                 750
Glu Trp Lys His Gly Arg Ile Ile Leu Pro Ser Tyr Asp Met Glu Tyr
                755                 760                 765
Gln Ile Val Phe Glu Gly Val Ile Gly Lys Gly Arg Ser Gly Glu Ile
                770                 775                 780
Ala Ile Asp Asp Ile Arg Ile Ser Thr Asp Val Pro Leu Glu Asn Cys
785                 790                 795                 800
Met Glu Pro Ile Ser Ala Phe Ala Val Asp Ile Pro Glu Ile His Glu
                805                 810                 815
```

```
Arg Glu Gly Tyr Glu Asp Glu Ile Asp Asp Glu Tyr Glu Val Asp Trp
                820                 825                 830

Ser Asn Ser Ser Ser Ala Thr Ser Gly Ser Gly Ala Pro Ser Thr Asp
            835                 840                 845

Lys Glu Lys Ser Trp Leu Tyr Thr Leu Asp Pro Ile Leu Ile Thr Ile
    850                 855                 860

Ile Ala Met Ser Ser Leu Gly Val Leu Leu Gly Ala Thr Cys Ala Gly
865                 870                 875                 880

Leu Leu Leu Tyr Cys Thr Cys Ser Tyr Ser Gly Leu Ser Ser Arg Ser
                885                 890                 895

Cys Thr Thr Leu Glu Asn Tyr Asn Phe Glu Leu Tyr Asp Gly Leu Lys
                900                 905                 910

His Lys Val Lys Met Asn His Gln Lys Cys Cys Ser Glu Ala
                915                 920                 925

<210> SEQ ID NO 14
<211> LENGTH: 2781
<212> TYPE: DNA
<213> ORGANISM: Homo sapiens

<400> SEQUENCE: 14
```

| | | | | | |
|---|---|---|---|---|---|
| atggatatgt | ttcctctcac | ctgggttttc | ttagccctct | acttttcaag | acaccaagtg | 60 |
| agaggccaac | cagacccacc | gtgcggaggt | cgtttgaatt | ccaaagatgc | tggctatatc | 120 |
| acctctcccg | gttaccccca | ggactacccc | tcccaccaga | actgcgagtg | gattgtttac | 180 |
| gccccccgaac | ccaaccagaa | gattgtcctc | aacttcaacc | ctcactttga | aatcgagaag | 240 |
| cacgactgca | agtatgactt | tatcgagatt | cgggatgggg | acagtgaatc | cgcagacctc | 300 |
| ctgggcaaac | actgtgggaa | catcgccccg | cccaccatca | tctcctcggg | ctccatgctc | 360 |
| tacatcaagt | tcacctccga | ctacgcccgg | caggggcag | gcttctctct | cgctacgag | 420 |
| atcttcaaga | caggctctga | agattgctca | aaaaacttca | aagcccccaa | cgggaccatc | 480 |
| gaatctcctg | gtttcctga | aagtatcca | cacaacttgg | actgcacctt | taccatcctg | 540 |
| gccaaaccca | agatggagat | catcctgcag | ttcctgatct | ttgacctgga | gcatgaccct | 600 |
| ttgcaggtgg | agaggggga | ctgcaagtac | gattggctgg | acatctggga | tggcattcca | 660 |
| catgttggcc | ccctgattgg | caagtactgt | gggaccaaaa | caccctctga | acttcgttca | 720 |
| tcgacgggga | tcctctcct | gacctttcac | acggacatgg | cggtggccaa | ggatggcttc | 780 |
| tctgcgcgtt | actacctggt | ccaccaagag | ccactagaga | actttcagtg | caatgttcct | 840 |
| ctgggcatgg | agtctggccg | gattgctaat | gaacagatca | gtgcctcatc | tacctactct | 900 |
| gatgggaggt | ggaccccctca | acaaagccgg | ctccatggtg | atgacaatgg | ctggaccccc | 960 |
| aacttggatt | ccaacaagga | gtatctccag | gtggacctgc | gcttttaac | catgctcacg | 1020 |
| gccatcgcaa | cacagggagc | gatttccagg | gaaacacaga | atggctacta | tgtcaaatcc | 1080 |
| tacaagctgg | aagtcagcac | taatggagag | gactggatgg | tgtaccggca | tggcaaaaac | 1140 |
| cacaaggtat | ttcaagccaa | caacgatgca | actgaggtgg | ttctgaacaa | gctccacgct | 1200 |
| ccactgctga | caaggtttgt | tagaatccgc | cctcagacct | ggcactcagg | tatcgccctc | 1260 |
| cggctggagc | tcttcggctg | ccgggtcaca | gatgctccct | gctccaacat | gctgggatg | 1320 |
| ctctcaggcc | tcattgcaga | ctcccagatc | tccgcctctt | ccaccaggga | ataccctctgg | 1380 |
| agccccagtg | cagcccgcct | ggtcagcagc | cgctcgggct | ggttccctcg | aatccctcag | 1440 |
| gcccagcccg | gtgaggagtg | gcttcaggta | gatctgggaa | cacccaagac | agtgaaaggt | 1500 |

```
gtcatcatcc agggagcccg cggaggagac agtatcactg ctgtggaagc cagagcattt    1560
gtgcgcaagt tcaaagtctc ctacagccta acggcaagg actgggaata cattcaggac    1620
cccaggaccc agcagccaaa gctgttcgaa gggaacatgc actatgacac ccctgacatc    1680
cgaaggtttg accccattcc ggcacagtat gtgcgggtat acccgagag gtggtcgccg    1740 gcggggattg ggatgcggct ggaggtgctg ggctgtgact ggacagactc caagcccacg    1800
gtagagacgc tgggacccac tgtgaagagc aagagacaa ccacccccta ccccaccgaa    1860
gaggaggcca cagagtgtgg ggagaactgc agctttgagg atgacaaaga tttgcagctc    1920
ccttcgggat tcaattgcaa cttcgatttc ctcgaggagc cctgtggttg gatgtatgac    1980
catgccaagt ggctccggac cacctgggcc agcagctcca gcccaaacga ccggacgttt    2040
ccagatgaca ggaatttctt gcggctgcag agtgacagcc agagagaggg ccagtatgcc    2100
cggctcatca gccccctgt ccacctgccc cgaagcccgg tgtgcatgga gttccagtac    2160
caggccacgg gcggccgcgg ggtggcgctg caggtggtgc gggaagccag ccaggagagc    2220
aagttgctgt gggtcatccg tgaggaccag ggcggcgagt ggaagcacgg gcggatcatc    2280
ctgcccagct acgacatgga gtaccagatt gtgttcgagg gagtgatagg gaaaggacgt    2340
tccggagaga ttgccattga tgacattcgg ataagcactg atgtcccact ggagaactgc    2400
atggaaccca tctcggcttt tgcagtggac atcccagaaa tacatgagag gaaggatat    2460 gaagatgaaa ttgatgatga atacgaggtg gactggagca attcttcttc tgcaacctca    2520
gggtctggcg cccctcgac cgacaaagaa aagagctggc tgtacaccct ggatcccatc    2580
ctcatcacca tcatcgccat gagctcactg ggcgtcctcc tgggggccac ctgtgcaggc    2640
ctcctgctct actgcacctg ttcctactcg ggcctgagct cccgaagctg caccacactg    2700
gagaactaca acttcgagct ctacgatggc cttaagcaca aggtcaagat gaaccaccaa    2760
aagtgctgct ccgaggcatg a                                              2781
```

<210> SEQ ID NO 15
<211> LENGTH: 2027
<212> TYPE: DNA
<213> ORGANISM: Homo sapiens

<400> SEQUENCE: 15

```
tgtggctgca gagcctgctg ctcttgggca ctgtggcctg cagcatctct gcacccgccc      60
gctcgcccag ccccagcacg cagccctggg agcatgtgaa tgccatccag gaggcccggc     120
gtctcctgaa cctgagtaga gacactgctg ctgagatggt aagtgagaga atgtgggcct     180
gtgcctaggc cacccagctg gcccctgact ggccacgcct gtcagcttga taacatgaca     240
ttttcctttt ctacagaatg aaacagtaga agtcatctca gaaatgtttg acctccaggt     300
aagatgcttc tctctgacat agctttccag aagcccctgc cctggggtgg aggtggggac     360 tccatttag atggcaccac acagggttgt ccactttctc tccagtcagc tggctgcagg     420 aggaggggt agcaactggg tgctcaagag gctgctggcc gtgccctat ggcagtcaca     480 tgagctcctt tatcagctga gcggccatgg gcagacctag cattcaatgg ccaggagtca     540
ccaggggaca ggtggtaaag tggggtcac ttcatgagac aggagctgtg gtttggggc     600 gctcactgtg ccccgagacc aagtcctgtt gagacagtgc tgactacaga gaggcacaga     660 gggggtttcag gaacaaccct tgcccaccca gcaggtccag gtgaggcccc accccctct     720 ccctgaatga tggggtgaga gtcacctcct tccctaaggc tgggctcctc tccaggtgcc     780
```

```
gctgagggtg gcctgggcgg ggcagtgaga agggcaggtt cgtgcctgcc atggacaggg      840
cagggtctat gactggaccc agcctgtgcc cctcccaagc cctactcctg ggggctgggg      900
gcagcagcaa aaggagtgg tggagagttc ttgtaccact gtgggcactt ggccactgct      960
caccgacgaa cgacattttc cacaggagcc gacctgccta cagacccgcc tggagctgta     1020
caagcagggc ctgcggggca gcctcaccaa gctcaagggc cccttgacca tgatggccag     1080
ccactacaag cagcactgcc ctccaacccc ggtgagtgcc tacggcaggg cctccagcag     1140
gaatgtctta atctagggg tggggtcgac atggggagag atctatggct gtggctgttc     1200
aggaccccag ggggtttctg tgccaacagt tatgtaatga ttagccctcc agagaggagg     1260
cagacagccc atttcatccc aaggagtcag agccacagag cgctgaagcc cacagtgctc     1320
cccagcagga gctgctccta tcctggtcat tattgtcatt atggttaatg aggtcagagg     1380
tgagggcaaa cccaaggaaa cttggggcct gcccaaggcc cagaggaagt gcccaggccc     1440
aagtgccacc ttctggcagg actttcctct ggccccacat ggggtgcttg aattgcagag     1500
gatcaaggaa gggggctac ttggaatgga caaggacctc aggcactcct tcctgcggga     1560
agggagcaaa gtttgtggcc ttgactccac tccttctggg tgcccagaga cgacctcagc     1620
ccagctgccc tgctctgccc tgggaccaaa aaggcaggcg tttgactgcc agaaggcca      1680 acctcaggct ggcacttaag tcaggccctt gactctggct gccactggca gagctatgca     1740
ctccttgggg aacacgtggg tggcagcagc gtcacctgac ccaggtcagt gggtgtgtcc     1800
tggagtgggc ctcctggcct ctgagttcta agaggcagta gagaaacatg ctggtgcttc     1860
cttcccccac gttacccact tgcctggact caagtgtttt ttattttttct ttttttaaag     1920 gaaacttcct gtgcaaccca gattatcacc tttgaaagtt tcaaagagaa cctgaaggac     1980
tttctgcttg tcatcccctt tgactgctgg gagccagtcc aggagtg                   2027

<210> SEQ ID NO 16
<211> LENGTH: 435
<212> TYPE: DNA
<213> ORGANISM: Homo sapiens

<400> SEQUENCE: 16
atgtggctgc agagcctgct gctcttgggc actgtggcct gcagcatctc tgcacccgcc       60
cgctcgccca gccccagcac gcagccctgg gagcatgtga atgccatcca ggaggcccgg      120
cgtctcctga acctgagtag agacactgct gctgagatga atgaaacagt agaagtcatc      180
tcagaaatgt ttgacctcca ggagccgacc tgcctacaga cccgcctgga gctgtacaag      240
cagggcctgc ggggcagcct caccaagctc aagggcccct tgaccatgat ggccagccac      300
tacaagcagc actgccctcc aaccccggaa acttcctgtg caaccagac tatcaccttt      360 gaaagtttca agagaacct gaaggacttt ctgcttgtca tcccctttga ctgctgggag      420
ccagtccagg agtaa                                                       435

<210> SEQ ID NO 17
<211> LENGTH: 144
<212> TYPE: PRT
<213> ORGANISM: Homo sapiens

<400> SEQUENCE: 17

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30
```

-continued

Val Asn Ala Ile Gln Glu Ala Arg Arg Leu Leu Asn Leu Ser Arg Asp
     35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
                100                 105                 110

Cys Ala Thr Gln Thr Ile Thr Phe Glu Ser Phe Lys Glu Asn Leu Lys
                115                 120                 125

Asp Phe Leu Leu Val Ile Pro Phe Asp Cys Trp Glu Pro Val Gln Glu
130                 135                 140

```
<210> SEQ ID NO 18
<211> LENGTH: 20
<212> TYPE: DNA
<213> ORGANISM: Homo sapiens

<400> SEQUENCE: 18
actacctgat cagtgtcaaa                                              20

<210> SEQ ID NO 19
<211> LENGTH: 32
<212> TYPE: DNA
<213> ORGANISM: Homo sapiens

<400> SEQUENCE: 19
gtaatctccg gaaggcactg tgacatgaaa ag                                32

<210> SEQ ID NO 20
<211> LENGTH: 20
<212> TYPE: DNA
<213> ORGANISM: Homo sapiens

<400> SEQUENCE: 20
gcctacccac aggagattcc                                              20

<210> SEQ ID NO 21
<211> LENGTH: 32
<212> TYPE: DNA
<213> ORGANISM: Homo sapiens

<400> SEQUENCE: 21
gtaatctccg gaaggtgcaa gtctctcata ga                                32

<210> SEQ ID NO 22
<211> LENGTH: 39
<212> TYPE: DNA
<213> ORGANISM: Homo sapiens

<400> SEQUENCE: 22
gggcccgaat tcatggcggc ggagcgacag gaggcgctg                         39

<210> SEQ ID NO 23
<211> LENGTH: 32
<212> TYPE: DNA
<213> ORGANISM: Homo sapiens

<400> SEQUENCE: 23
```

-continued

```
gtaatctccg gatgttaacc gctgcacgat ga                                    32
```

<210> SEQ ID NO 24
<211> LENGTH: 30
<212> TYPE: DNA
<213> ORGANISM: Homo sapiens

<400> SEQUENCE: 24

```
atatggatcc atggccgtca tggcgccccg                                       30
```

<210> SEQ ID NO 25
<211> LENGTH: 30
<212> TYPE: DNA
<213> ORGANISM: Homo sapiens

<400> SEQUENCE: 25

```
aatctccgga cactttacaa gctgtgagag                                       30
```

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32
<211> LENGTH: 54
<212> TYPE: PRT
<213> ORGANISM: Homo sapiens

<400> SEQUENCE: 32

```
Met Ala Ala Val Ala Ala Ala Ser Ala Glu Leu Leu Ile Ile Gly Trp
1               5                   10                  15

Tyr Ile Phe Arg Val Leu Leu Gln Val Phe Arg Tyr Ser Leu Gln Lys
            20                  25                  30
```

Leu Ala Tyr Thr Val Ser Arg Thr Gly Arg Gln Val Leu Gly Glu Arg
    35                  40                  45

Arg Gln Arg Ala Pro Asn
    50

<210> SEQ ID NO 33
<211> LENGTH: 1257
<212> TYPE: DNA
<213> ORGANISM: Homo sapiens

<400> SEQUENCE: 33

| | | | | | |
|---|---|---|---|---|---|
| taggtggcgg | gcgggtactt | aaggcgcggc | caccgcggct | gcggcagtgc | gcccaacagc | 60 |
| ggactccgag | accagcggat | ctcggcaaac | cctctttctc | gaccacccac | ctaccattct | 120 |
| tggaaccatg | gcggcagtgg | cggcggcctc | ggctgaactg | ctcatcatcg | gctggtacat | 180 |
| cttccgcgtg | ctgctgcagg | tgttcaggta | ctccctgcag | aagctggcat | acacggtgtc | 240 |
| gcggaccggg | cggcaggtgt | tggggggagcg | caggcagcga | gcccccaact | gaggccccag | 300 |
| ctcccagccc | tgggcggccg | tatcatcagg | tgctcctgtg | catctcggcc | agcacggagg | 360 |
| ccagtgccgc | gcaggaatgt | ggggtcccct | gtgttccctc | gccagaggag | cacttggcaa | 420 |
| ggtcagtgag | gggccagtag | acccccggag | aagcagtacc | gacaatgacg | aagataccag | 480 |
| atcccttccc | aacccctttg | caccggtccc | actaaggggc | agggtcgaga | gaggaggggg | 540 |
| gatagggggga | gcagacccct | gagatctggg | cataggcacc | gcattctgat | ctggacaaag | 600 |
| tcgggacagc | accatcccag | ccccgaagcc | agggccatgc | cagcaggccc | caccatggaa | 660 |
| atcaaaacac | cgcaccagcc | agcagaatgg | acattctgac | atcgccagcc | gacgccctga | 720 |
| atcttggtgc | agcaccaacc | gcgtgcctgt | gtggcgggac | tggagggcac | agttgaggaa | 780 |
| ggagggtggt | taagaaatac | agtggggccc | tctcgctgtc | ccttgcccag | ggcacttgca | 840 |
| ttccagcctc | gctgcatttg | ctctctcgat | tccccttttcc | tcctcactgc | ctcccaagcc | 900 |
| caccctactc | caaaataatg | tgtcacttga | tttggaacta | ttcaagcagt | aaaagtaaat | 960 |
| gaatcccacc | tttactaaaa | cactttctct | gaaccccccct | tgcccctcac | tgatcttgct | 1020 |
| tttccctggt | ctcatgcagt | tgtggtcaat | attgtggtaa | tcgctaattg | tactgattgt | 1080 |
| ttaagtgtgc | attagttgtg | tctccccagc | tagattgtaa | gctcctggag | gacagggacc | 1140 |
| acctctacaa | aaaataaaaa | aagtacctcc | cctgtctcgc | acagtgtccc | aggaccctgc | 1200 |
| ggtgcagtag | aggcgcacca | aaaaaaaaaa | aaaaaaaaaa | aaaaaaaaaa | aaaaaaa | 1257 |